US009677977B2

(12) United States Patent
Lapen et al.

(10) Patent No.: US 9,677,977 B2
(45) Date of Patent: *Jun. 13, 2017

(54) FIXATIVE AND STAINING SOLUTIONS

(71) Applicant: Roche Diagnostics Hematology, Inc., Westborough, MA (US)

(72) Inventors: Daniel Lapen, Lancaster, MA (US); Kerri Horton, Boston, MA (US)

(73) Assignee: Roche Diagnostics Hematology, Inc., Westborough, MA (US)

( * ) Notice: Subject to any disclaimer, the term of this patent is extended or adjusted under 35 U.S.C. 154(b) by 610 days.

This patent is subject to a terminal disclaimer.

(21) Appl. No.: 13/795,536

(22) Filed: Mar. 12, 2013

(65) Prior Publication Data
US 2013/0196370 A1    Aug. 1, 2013

Related U.S. Application Data

(63) Continuation of application No. 13/526,164, filed on Jun. 18, 2012, now Pat. No. 8,445,284.
(Continued)

(51) Int. Cl.
*G01N 1/30* (2006.01)
*G01N 1/31* (2006.01)
(Continued)

(52) U.S. Cl.
CPC .............. *G01N 1/30* (2013.01); *Y10T 436/10* (2015.01); *Y10T 436/101666* (2015.01); *Y10T 436/108331* (2015.01); *Y10T 436/25* (2015.01)

(58) Field of Classification Search
None
See application file for complete search history.

(56) References Cited

U.S. PATENT DOCUMENTS 4,225,669 A  9/1980 Melnick
4,290,769 A  9/1981 Liao
(Continued)

FOREIGN PATENT DOCUMENTS

CN  101035589  9/2007
CN  102083456  6/2011
(Continued)

OTHER PUBLICATIONS

Kuhlmann "Romanoiwsky-Giemsa staining" Oct. 9, 2006.*
(Continued)

*Primary Examiner* — Blaine Lankford
*Assistant Examiner* — Lauren K Van Buren
(74) *Attorney, Agent, or Firm* — Fish & Richardson P.C.

(57) ABSTRACT

The formulations, systems, and methods disclosed herein permit automated preparation of specimens (e.g., biological specimens) for examination. The disclosed formulations, systems, and methods provide fast, efficient, and highly uniform specimen processing using minimal quantities of fluids. The methods include at least a fixing phase for fixing a specimen to a substrate such as a microscope slide, a staining phase for staining the specimen, and a rinsing phase for rinsing the specimen. One or more of the fixing, staining, and rinsing phases include one or more agitation phases for distributing reagents evenly and uniformly across the specimen. The systems can be implemented as a standalone device or as a component in a larger system for preparing and examining specimens.

16 Claims, 31 Drawing Sheets

Related U.S. Application Data

(60) Provisional application No. 61/498,159, filed on Jun. 17, 2011, provisional application No. 61/505,011, filed on Jul. 6, 2011, provisional application No. 61/510,180, filed on Jul. 21, 2011.

(51) Int. Cl.

| | |
|---|---|
| *G01N 1/28* | (2006.01) |
| *G01N 35/00* | (2006.01) |
| *G01N 35/10* | (2006.01) |
| *A61B 10/00* | (2006.01) |
| *C12M 1/34* | (2006.01) |
| *C12Q 1/02* | (2006.01) |

(56) References Cited

U.S. PATENT DOCUMENTS

| | | | |
|---|---|---|---|
| 4,336,337 A | 6/1982 | Wallis | |
| 4,363,632 A | 12/1982 | Custard | |
| 4,382,075 A | 5/1983 | Liao | |
| 4,392,864 A | 7/1983 | Helfrich | |
| 4,595,524 A | 6/1986 | Yip | |
| 4,687,489 A | 8/1987 | Rieke | |
| 4,741,898 A | 5/1988 | Mallik | |
| 4,810,487 A | 3/1989 | Kass | |
| 4,816,244 A | 3/1989 | Starkweather | |
| 4,933,164 A | 6/1990 | Rieke | |
| 4,983,375 A * | 1/1991 | Mauthner | G01N 33/5094 435/40.51 |
| 5,109,429 A | 4/1992 | Bacus | |
| 5,485,527 A | 1/1996 | Bacus et al. | |
| 5,677,183 A | 10/1997 | Takarada | |
| 5,728,582 A | 3/1998 | Taki | |
| 5,733,784 A | 3/1998 | Studhome | |
| 5,739,318 A | 4/1998 | Frantzen | |
| 5,804,448 A | 9/1998 | Wang et al. | |
| 6,165,734 A | 12/2000 | Garini | |
| 6,174,728 B1 | 1/2001 | Ben-David et al. | |
| 6,190,609 B1 | 2/2001 | Chapman | |
| 6,352,672 B1 | 3/2002 | Mabile | |
| 6,399,553 B1 | 6/2002 | Cable et al. | |
| 6,664,110 B1 | 12/2003 | Tsuji | |
| 6,858,432 B2 | 2/2005 | Stokes et al. | |
| 6,861,264 B2 | 3/2005 | Mabile | |
| 6,947,583 B2 | 9/2005 | Ellis | |
| 6,951,713 B2 | 10/2005 | Hei | |
| 6,955,872 B2 | 10/2005 | Maples et al. | |
| 6,967,015 B1 | 11/2005 | Burkett | |
| 7,026,110 B1 | 4/2006 | Veriac | |
| 7,045,757 B1 | 5/2006 | Tuschel | |
| 7,049,093 B2 | 5/2006 | Tsuji | |
| 7,303,920 B2 | 12/2007 | Stokes et al. | |
| 7,323,461 B2 | 1/2008 | Juneau | |
| 7,326,579 B2 | 2/2008 | Yamao | |
| 7,432,372 B2 | 10/2008 | Batchelor | |
| 7,521,405 B2 | 4/2009 | Zhang et al. | |
| 7,592,300 B2 | 9/2009 | Taylor et al. | |
| 7,611,831 B2 | 11/2009 | Hei | |
| 7,713,472 B2 | 5/2010 | Raad | |
| 7,745,219 B2 | 6/2010 | Summer | |
| 7,767,210 B2 | 8/2010 | Dittner | |
| 7,782,447 B2 | 8/2010 | Lindberg | |
| 7,820,158 B2 | 10/2010 | Chudzik | |
| 7,875,261 B2 | 1/2011 | Batchelor et al. | |
| 7,941,275 B2 | 5/2011 | Gholap | |
| 7,979,212 B2 | 7/2011 | Gholap | |
| 8,068,988 B2 | 11/2011 | Gholap | |
| 8,158,381 B2 | 4/2012 | Wiederhold | |
| 8,280,134 B2 | 10/2012 | Hoyt | |
| 2004/0043495 A1 | 3/2004 | Stokes et al. | |
| 2004/0191854 A1* | 9/2004 | Lapen | G01N 1/30 435/40.5 |
| 2005/0148083 A1 | 7/2005 | Stokes et al. | |
| 2006/0034902 A1 | 2/2006 | Cormier et al. | |
| 2006/0199243 A1 | 9/2006 | Garner et al. | |
| 2008/0064113 A1 | 3/2008 | Goix et al. | |
| 2008/0227143 A1* | 9/2008 | Kosmeder | G01N 1/30 435/40.52 |
| 2011/0212055 A1 | 9/2011 | Commissiong | |
| 2011/0229879 A1 | 9/2011 | Churukian | |
| 2011/0311123 A1 | 12/2011 | Gholap | |
| 2012/0093387 A1 | 4/2012 | Gholap | |
| 2012/0122151 A1* | 5/2012 | Dagiral et al. | 435/40.5 |

FOREIGN PATENT DOCUMENTS

| | | |
|---|---|---|
| EP | 656540 | 6/1995 |
| FR | 2402204 | 3/1979 |
| FR | 2907220 | 4/2008 |
| JP | 62-240860 | 10/1987 |
| JP | 2004-504036 | 2/2004 |
| JP | 2005-524072 | 8/2005 |
| WO | WO 02/06524 | 1/2002 |
| WO | WO 03/091729 | 11/2003 |
| WO | 2008/043963 | 4/2008 |
| WO | 2008154457 | 12/2008 |
| WO | 2009076645 | 6/2009 |
| WO | 2009148885 | 12/2009 |
| WO | 2011010064 | 1/2011 |
| WO | WO2011010064 * | 1/2011 |

OTHER PUBLICATIONS

International Preliminary Report on Patentability mailed Jan. 3, 2014 in international application No. PCT/US2012/042961, 13 pgs.
Examination Report mailed Mar. 4, 2014 in corresponding Australian application No. 2012271330, 5 pgs.
Examination Report mailed Sep. 22, 2014 in corresponding Australian application No. 2012271330, 4 pgs.
English translation of Japanese Office Action issued on Apr. 5, 2016 in corresponding JP Patent Application No. 2014-516078, 10 pages.
English translation of Second Office Action issued on Dec. 28, 2015 in corresponding Chinese Application No. 201280039988.1, 28 pages.
English translation of Search Report issued on on Dec. 28, 2015 in corresponding Chinese Application No. 201280039988.1, 3 pages.
Biocare Medical, Wash Buffer and Mounting Media, Sep. 22, 2010, http://web.archive.org/web/20100922222303/http://biocare.net/products/ancillaries/buffers-wash-buffers-mounting-media/.
Authorized officer Richard Michalitsch, International Search Report and Written Opinion issued in application No. PCT/US2012/042961, dated Nov. 14, 2012, 19 total pages.
Apostolou, A. et al., "Armet, a UPR-upregulated protein, inhibits cell proliferation and ER stress-induced cell death", Exp Cell Res., vol. 14(13):2454-67 (2008).
English translation of the Second Office Action for corresponding CN Appl. No. 201380016366.1 issued on Feb. 19, 2016, 5 pp.
English Translation of First Office Action issued on May 19, 2015 in corresponding Chinese application No. 201280039988.1, 28 pgs.
English translation of Search Report issued on May 19, 2015 in corresponding Chinese application No. 20280039988.1, 5 pgs.

* cited by examiner

FIXATIVE AND STAINING SOLUTIONS

CROSS REFERENCE TO RELATED APPLICATIONS

This application is a continuation of U.S. application Ser. No. 13/526,164, filed on Jun. 18, 2012, which claims the benefit of U.S. Provisional Application No. 61/498,159, filed on Jun. 17, 2011, U.S. Provisional Application No. 61/505,011, filed on Jul. 6, 2011, and U.S. Provisional Application No. 61/510,180, filed on Jul. 21, 2011; the disclosures of each of which are incorporated herein by reference in their entireties.

TECHNICAL FIELD

This disclosure relates to formulations for preparation of biological specimens, and more particularly to fixing, staining, and rinsing formulations.

BACKGROUND

For years, laboratory technologists have used dyes and stains such as those used in Romanowsky staining for preparing biological specimens to improve the contrast of a specimen during examination. Such examination typically utilizes a microscope, an automated device that captures images of the specimen, or, in other instances, unaided visual examination. Several different systems and methods for preparing a specimen for examination are known. For example, U.S. Pat. Nos. 6,096,271; 7,318,913; 5,419,279; and 5,948,360, and published U.S. Patent Application Nos. 2008/0102006 and 2006/0073074 relate to machines and methods for staining a substrate during specimen processing. These publications provide various details on staining and preparing specimens for examination.

SUMMARY

The present disclosure relates to formulations, systems, and methods for preparing specimens for examination. The specimens can include, for example, blood samples comprising red blood cells, white blood cells, and platelets from biological samples, e.g., a blood sample, applied to a substrate, e.g., a microscope slide or a cover slip. Different embodiments can be used to prepare specimens from biological samples including bone marrow, urine, vaginal tissue, epithelial tissue, tumors, semen, saliva, and other body fluids. Additional aspects of the disclosure include systems and methods for fixing, staining, rinsing, and agitating the specimens, using the formulations of the disclosure. In general, the formulations, systems, and methods disclosed herein provide for rapid, efficient, and highly uniform specimen preparation and processing using minimal fluid quantities. The methods include one or more fixing, staining, and rinsing phases, including one or multiple agitation phases after one or more, e.g., after each of, the fixing, staining, and rinsing phases. The systems can be implemented as a standalone device or as a component in a larger system for preparing and examining specimens.

In a first aspect, the disclosure features a cytological fixative solution including Azure B; a surfactant; methanol; and ethylene glycol.

For example, the cytological fixative solution can include about 0.5 g/L to about 5.0 g/L Azure B; about 0.5 mL/L to about 2.0 mL/L polysorbate 20; about 5 mL/L to about 50 mL/L ethylene glycol, propylene glycol, or polypropylene glycol; about 0.1 g/L to about 10 g/L HEPES sodium salt; and methanol.

As another example, the cytological fixative solution can include about 0.8 g/L to about 1.2 g/L Azure B; about 0.8 mL/L to about 1.2 mL/L polysorbate 20; about 9 mL/L to about 11 mL/L ethylene glycol; about 0.25 g/L to about 0.38 g/L HEPES sodium salt; and methanol.

For example, the cytological fixative solution can include about one g/L Azure B; about one mL/L polysorbate 20; about 10 mL/L ethylene glycol; about 0.32 g/L HEPES sodium salt; and methanol.

As another example, the cytological fixative solution can include about one g/L Azure B; about 0.5 mL/L polysorbate 20; about 10 mL/L propylene glycol; about 0.32 g/L HEPES sodium salt; and methanol.

As a further example, the cytological fixative solution can include about one g/L Azure B; about 1.5 mL/L polysorbate 20; about 10 mL/L polypropylene glycol; about 0.32 g/L HEPES sodium salt; and methanol.

In a second aspect, the disclosure features a first cytological staining solution, including eosin Y; a buffering agent; a surfactant; sodium chloride; ethylene glycol; and water.

For example, the first cytological staining solution can include about 0.5 g/L to about 5.0 g/L Eosin Y; about 5 mM to about 250 mM bis-tris or phosphate buffer; about 0.5 mL/L to about 2.0 mL/L polysorbate 20; about one g/L to about 20 g/L sodium chloride; about five mL/L to about 50 mL/L ethylene glycol; about 0.2 ppm to about 50 ppm ProClin 300®; acetic acid; and water, wherein the solution has a pH of from about 5.8 to about 6.2.

As another example, the first cytological staining solution can include about 0.6 g/L to about 0.9 g/L Eosin Y; about 45 mM to about 55 mM bis-tris buffer; about 0.8 mL/L to about 1.2 mL/L polysorbate 20; about three g/L to about five g/L sodium chloride; about nine mL/L to about 11 mL/L ethylene glycol; about 10 ppm to about 20 ppm ProClin 300®; acetic acid; and water, wherein the solution has a pH of from about 5.8 to about 6.2.

For example, the first cytological staining solution can include about 0.75 g/L Eosin Y; about 50 mM bis-tris buffer; about one mL/L polysorbate 20; about four g/L sodium chloride; about 10 mL/L ethylene glycol; about 15 ppm ProClin 300®; acetic acid; and water, wherein the solution has a pH of from about 5.8 to about 6.2.

As another example, the first cytological staining solution can include about 0.75 g/L Eosin Y; about 50 mM bis-tris buffer; about 0.5 mL/L polysorbate 20; about six g/L sodium chloride; about 20 mL/L ethylene glycol; about 15 ppm ProClin 300®; acetic acid; and water, wherein the solution has a pH of from about 5.8 to about 6.2.

As a further example, the first cytological staining solution can include about 0.75 g/L Eosin Y; about 50 mM phosphate buffer; about 2.0 mL/L polysorbate 20; about four g/L sodium chloride; about 50 mL/L ethylene glycol; about 15 ppm ProClin 300®; acetic acid; and water, wherein the solution has a pH of from about 5.8 to about 6.2.

In a third aspect, the disclosure features a second cytological staining solution, including Azure B; methylene blue; a buffering agent; a surfactant, sodium chloride, and water.

For example, the second cytological staining solution can include about 0.25 to about 2.5 g/L Azure B; about 0.25 g/L to about 2.5 g/L methylene blue; about 5 mM to about 250 mM bis-tris or HEPES buffer; about 0.5 mL/L to about 2.0 mL/L polysorbate 20, about one g/L to about 20 g/L sodium chloride, and about 0.2 ppm to about 50 ppm ProClin 300®; acetic acid; and water, wherein the solution has a pH of from about 6.8 to about 7.2.

As another example, the second cytological staining solution can include about 0.4 to about 0.6 g/L Azure B; about 0.4 g/L to about 0.5 g/L methylene blue; about 45 mM to about 55 mM bis-tris buffer; about 0.8 mL/L to about 1.2 mL/L polysorbate 20, about 1.8 g/L to about 2.2 g/L sodium chloride, and about 10 ppm to about 20 ppm ProClin 300®; acetic acid; and water, wherein the solution has a pH of from about 6.8 to about 7.2.

For example, the second cytological staining solution can include about 0.5 g/L Azure B; about 0.45 g/L methylene blue; about 50 mM bis-tris buffer; about one mL/L polysorbate 20, about two g/L sodium chloride, and about 15 ppm ProClin 300®; acetic acid; and water, wherein the solution has a pH of from about 6.8 to about 7.2.

As another example, the second cytological staining solution can include about 0.5 g/L Azure B; about 0.45 g/L methylene blue; about 50 mM HEPES buffer; about 0.5 mL/L polysorbate 20, about two g/L sodium chloride, and about 15 ppm ProClin 300®; acetic acid; and water, wherein the solution has a pH of from about 6.8 to about 7.2.

As a further example, the second cytological staining solution can include about 0.5 g/L Azure B; about 0.45 g/L methylene blue; about 50 mM HEPES buffer; about one mL/L polysorbate 20, about one g/L sodium chloride, and about 15 ppm ProClin 300®; acetic acid; and water, wherein the solution has a pH of from about 6.8 to about 7.2.

In a fourth aspect, the disclosure features a rinse solution for an automated specimen preparation apparatus, including polyethylene glycol; a buffering agent; a surfactant; methanol; and water.

For example, the rinse solution can include about 0.2 g/L to about ten g/L polyethylene glycol; about 1 mM to about 250 mM HEPES, MES, or bis-tris buffer; about 0.1 mL/L to about 2.40 mL/L polysorbate 20; about 0.04 ppm to about 50 ppm ProClin 300®; about 9 mL/L to about 200 mL/L methanol; and water, wherein the rinse solution has a pH of from about 6.6 to about 7.0.

For example, the rinse solution can include about one g/L to about ten g/L polyethylene glycol; about 5 mM to about 250 mM HEPES, MES, or bis-tris buffer; about 0.5 mL/L to about 2.0 mL/L polysorbate 20; about 0.2 ppm to about 50 ppm ProClin 300®; about 10 mL/L to about 200 mL/L methanol; and water, wherein the rinse solution has a pH of from about 6.6 to about 7.0.

As another example, the rinse solution can include about 4.5 g/L to about 5.5 g/L polyethylene glycol; about 45 mM to about 55 mM HEPES buffer; about 0.8 mL/L to about 1.2 mL/L polysorbate 20; about 10 ppm to about 20 ppm ProClin 300®; about 45 mL/L to about 55 mL/L methanol; and water, wherein the rinse solution has a pH of from about 6.6 to about 7.0.

For example, the rinse solution includes about five g/L polyethylene glycol; about 50 mM HEPES buffer; about one mL/L polysorbate 20; about 15 ppm ProClin 300®; about 50 mL/L methanol; and water, wherein the rinse solution has a pH of from about 6.6 to about 7.0.

As another example, the rinse solution includes about 10 g/L polyethylene glycol; about 50 mM MES buffer; about one mL/L polysorbate 20; about 15 ppm ProClin 300®; about 50 mL/L methanol; and water, wherein the rinse solution has a pH of from about 6.6 to about 7.0.

As a further example, the rinse solution includes about 10 g/L polyethylene glycol; about 50 mM bis-tris buffer; about 0.5 mL/L polysorbate 20; about 15 ppm ProClin 300®; about 50 mL/L methanol; and water, wherein the rinse solution has a pH of from about 6.6 to about 7.0.

For example, the rinse solution can include about 0.2 g/L to about two g/L polyethylene glycol; about one mM to about 50 mM HEPES buffer; about 0.16 mL/L to about 0.24 mL/L polysorbate 20; about 0.04 ppm to about 10 ppm ProClin 300®; about 9 mL/L to about 11 mL/L methanol; and water, wherein the rinse solution has a pH of from about 6.6 to about 7.0.

As another example, the rinse solution can include about 0.9 g/L to about 1.1 g/L polyethylene glycol; about 9 mM to about 11 mM HEPES buffer; about 0.16 mL/L to about 0.24 mL/L polysorbate 20; about 2 ppm to about 10 ppm ProClin 300®; about 9 mL/L to about 11 mL/L methanol; and water, wherein the rinse solution has a pH of from about 6.6 to about 7.0.

In still another example, the rinse solution includes about one g/L polyethylene glycol; about 10 mM HEPES buffer; about 0.2 mL/L polysorbate 20; about 3 ppm ProClin 300®; about 10 mL/L methanol; and water, wherein the rinse solution has a pH of from about 6.6 to about 7.0.

In a fifth aspect, the disclosure features a specimen preparation kit including a cytological fixative solution; a first cytological staining solution; a second cytological staining solution; and a rinse solution. In some embodiments, the specimen preparation kit includes a separately packaged cytological fixative solution; a separately packaged first cytological staining solution; a separately packaged second cytological staining solution; and a separately packaged rinse solution.

In a sixth aspect, the disclosure features a method of preparing a specimen on a substrate for examination, including (a) positioning the substrate with respect to a surface so that the specimen faces the surface, so that the substrate is positioned to form a separation between the surface and at least a portion of the substrate of at least about 100 microns; (b) performing a fixing phase including (i) dispensing a fixative solution into the separation between the substrate and the surface in an amount sufficient to contact the specimen and the surface; (ii) performing at least a first agitation phase, wherein the first agitation phase comprises changing the distance between the substrate and surface while the fixative solution is contacting the specimen for the duration of the first agitation phase; and (iii) removing the fixative solution from the separation and the specimen; (c) performing a first staining phase; (d) performing a second staining phase; and (e) performing a first rinse phase.

In a seventh aspect, the disclosure features a system for imaging a specimen, including an automated specimen analysis machine, and a cytological fixative solution; a first cytological staining solution; a second cytological staining solution; and/or a rinse solution. In some embodiments, the system for imaging a specimen includes an automated specimen analysis machine and a specimen prepared with: a cytological fixative solution; a first cytological staining solution; a second cytological staining solution; and/or a rinse solution.

Embodiments of the cytological fixative solutions, first cytological staining solutions, second cytological staining solutions, rinse solutions, methods, kits, and systems described herein can include any one or more of the following features.

In some embodiments, the cytological fixative solution can include from about 0.5 to about five g/L of Azure B (e.g., about one g/L Azure B). For example, a 1:1000 dilution of the cytological fixative solution in water has a UV absorbance of from about 0.1 to about one at a peak wavelength of from about 640 to about 650 nm.

In some embodiments, the cytological fixative solution is free or substantially free of one (or more) red stains (e.g., one or more conventional red stains known in the art, e.g., eosin Y, and fluorescein derivatives).

The cytological fixative solution can include from about 0.05% to about 0.5% by volume or by weight (e.g., from about 0.05% to about 0.3% by volume or by weight of the surfactant, from about 0.05% to about 0.1% by volume or by weight) of the surfactant. The surfactant can be selected from the group consisting of non-ionic, cationic, anionic, and zwitterionic surfactants. In some embodiments, the surfactant is non-ionic, and can include, for example, polysorbate 20. For example, the cytological fixative solution can include from about 0.5 mL/L to about two mL/L (e.g., from about 0.5 mL/L to about 1.5 mL/L, about one ml/L) of polysorbate 20.

In some embodiments, the cytological fixative solution can further include a buffering agent, such as bis-tris, phosphate, HEPES, MES, and/or Tris buffers. For example, a 1:10 dilution of the cytological fixative solution in water can have a pH of from about 6 to about 8 (e.g., from about 6.7 to about 7.3) and include from about 0.5 mM to about 10 mM of HEPES.

The cytological fixative solution can include from about 0.5 to about 5% (e.g., about one percent) by volume ethylene glycol.

In some embodiments, the cytological fixative solution can include about one g/L Azure B; about one mL/L polysorbate 20; about 10 mL/L ethylene glycol; about 0.32 g/L HEPES sodium salt; and methanol.

In some embodiments, the first cytological staining solution can include an antimicrobial agent (e.g., from about 0.2 to about 50 ppm of the antimicrobial agent), which can include, for example, benzalkonium chloride, 5-chloro-2-methyl-4-isothiazolin-3-one, 2-methyl-4-isothiazolin-3-one, ProClin® (e.g., ProClin 300®), azides, merthiolates, antibiotics, and any combination thereof. For example, the antimicrobial agent can include 5-chloro-2-methyl-4-isothiazolin-3-one and 2-methyl-4-isothiazolin-3-one. In some embodiments, the antimicrobial agent is ProClin 300®. For example, the first cytological staining solution can include about 15 ppm ProClin 300®.

The first cytological staining solution can include from about 0.5 to about one g/L (e.g., about 0.75 g/L) eosin Y. For example, a 1:500 dilution of the solution in water can have a UV absorbance of from about 0.1 to about one at a peak wavelength of from about 510 to about 530 nm.

In some embodiments, the first cytological staining solution is free or substantially free of one (or more) other red stains (e.g., one or more other conventional red stains known in the art, e.g., other fluorescein derivatives).

In some embodiments, the first cytological staining solution is free or substantially free of one (or more) blue stains (e.g., one or more conventional blue stains known in the art, e.g., azure B, methylene blue, and/or other thiazine dyes).

In some embodiments, the first cytological staining solution is free or substantially free of one (or more) other red stains (e.g., one or more other conventional red stains known in the art, e.g., other fluorescein derivatives), and the first cytological staining solution is free or substantially free of one (or more) blue stains (e.g., one or more conventional blue stains known in the art, e.g., azure B, methylene blue, and/or other thiazine dyes).

The first cytological staining solution can include from about 0.5 to about five percent (e.g., about one percent) by volume ethylene glycol.

In some embodiments, the first cytological staining solution can have a pH of from about 5 to about 8 and a buffering agent concentration of from about five to about 250 mM.

The buffering agent can include bis-tris, phosphate, HEPES, MES, Tris, and any combination thereof. For example, the first cytological staining solution can have a pH of from about 5.8 to about 6.2 and a bis-tris buffer concentration of from about five mM to about 250 mM. In some embodiments, the first cytological staining solution can further include acetic acid (e.g., from about two to about three mL/L acetic acid).

In some embodiments, the first cytological staining solution can include from about 0.05 to about 0.5% (e.g., from about 0.05% to about 0.3%, from about 0.05% to about 0.1%) by volume or by weight of the surfactant. The surfactant can be selected from the group consisting of non-ionic, cationic, anionic or zwitterionic surfactants. For example, the surfactant can be non-ionic, such as polysorbate 20. In some embodiments, the first cytological staining solution can include from about 0.5 mL/L to about two mL/L (e.g., from about 0.5 mL/L to about 1.5 mL/L, about one ml/L) of polysorbate 20.

In some embodiments, the first cytological staining solution can include from about one to about 20 g/L sodium chloride.

In some embodiments, the first cytological staining solution can include about 0.75 g/L Eosin Y; about 50 mM bis-tris buffer; about one mL/L polysorbate 20; about four g/L sodium chloride; about 10 mL/L ethylene glycol; about 15 ppm ProClin 300®; acetic acid; and water, wherein the solution has a pH of from about 5.8 to about 6.2.

In some embodiments, the second cytological staining solution can include an antimicrobial agent (e.g., from about 0.2 to about 50 ppm of the antimicrobial agent), which can include, for example, benzalkonium chloride, 5-chloro-2-methyl-4-isothiazolin-3-one, 2-methyl-4-isothiazolin-3-one, ProClin® (e.g., ProClin 300®), azides, merthiolates, antibiotics, and any combination thereof. For example, the antimicrobial agent can include 5-chloro-2-methyl-4-isothiazolin-3-one and 2-methyl-4-isothiazolin-3-one. In some embodiments, the second cytological staining solution can include ProClin 300® (e.g., about 15 ppm ProClin 300®).

In some embodiments, the second cytological staining solution can include from about 0.25 to about one g/L (e.g., about 0.5 g/L) azure B. The second cytological staining solution can include from about 0.25 to about one g/L (e.g., about 0.45 g/L) methylene blue. For example, a 1:1000 dilution of the second cytological staining solution in water can have a UV absorbance of from about 0.1 to about one at a peak wavelength of from about 640 to about 660 nm.

In some embodiments, the second cytological staining solution is free or substantially free of one (or more) other blue stains (e.g., one or more other conventional blue stains known in the art, e.g., azure B, methylene blue, and/or other thiazine dyes).

In some embodiments, the second cytological staining solution is free or substantially free of one (or more) red stains (e.g., one or more conventional red stains known in the art, e.g., fluorescein derivatives).

In some embodiments, the second cytological staining solution is free or substantially free of one (or more) other blue stains (e.g., one or more other conventional blue stains known in the art, e.g., other thiazine dyes), and the second cytological staining solution is free or substantially free of one (or more) red stains (e.g., one or more conventional red stains known in the art, e.g., fluorescein derivatives).

In some embodiments, the second staining solution can have a pH of from about 5 to about 8 and a buffering agent concentration of from about 5 mM to about 250 mM (e.g., a pH of from about 6.8 to about 7.2 and a bis-tris buffer concentration of from about 25 mM to about 100 mM). The buffering agent can include bis-tris buffer, phosphate, HEPES, MES, Tris, and any combination thereof. In some embodiments, the second cytological staining solution can further include acetic acid.

In some embodiments, the second cytological staining solution can include from about 0.05 to about 0.5% (e.g., from about 0.05% to about 0.3%, from about 0.05% to about 0.1%) by volume or by weight of the surfactant, which can include non-ionic, cationic, anionic, and zwitterionic surfactants. In some embodiments, the surfactant is non-ionic and can include polysorbate 20, and the second cytological staining solution can include from about 0.5 mL/L to about two mL/L (e.g., from about 0.5 mL/L to about 1.5 mL/L, about one ml/L) of polysorbate 20.

In some embodiments, the second cytological staining solution can include from about one to about 20 g/L sodium chloride.

In some embodiments, the second cytological staining solution can include about 0.5 g/L Azure B; about 0.45 g/L methylene blue; about 50 mM bis-tris buffer; about one mL/L polysorbate 20, about two g/L sodium chloride, and about 15 ppm ProClin 300®; acetic acid; and water. The solution can have a pH of from about 6.8 to about 7.2.

In some embodiments, the rinse solution can include an antimicrobial agent (e.g., from about 0.2 to about 50 ppm of the antimicrobial agent or from about 0.04 to about 10 ppm of the antimicrobial agent), which can include, for example, benzalkonium chloride, 5-chloro-2-methyl-4-isothiazolin-3-one, 2-methyl-4-isothiazolin-3-one, ProClin® (e.g., ProClin 300®), azides, merthiolates, antibiotics, and any combination thereof. In some embodiments, the antimicrobial agent can include 5-chloro-2-methyl-4-isothiazolin-3-one and 2-methyl-4-isothiazolin-3-one. For example, the rinse solution can include ProClin 300® (e.g., about 15 ppm ProClin 300 to about 3 ppm ProClin 300°).

The rinse solution can include from about one to about ten g/L (e.g., about five g/L) polyethylene glycol.

The rinse solution can include from about 0.2 to about two g/L (e.g., about one g/L) polyethylene glycol.

The rinse solution can have a pH of from 5 to 8 and a buffering agent concentration of from about five mM to about 250 mM (e.g., a pH of from about 5 to about 8 and a HEPES buffer concentration of about 50 mM). The buffering agent can include bis-tris buffer, phosphate, HEPES, MES, Tris, and any combination thereof.

The rinse solution can have a pH of from 5 to 8 and a buffering agent concentration of from about one mM to about 50 mM (e.g., a pH of from about 5 to about 8 and a HEPES buffer concentration of about 10 mM). The buffering agent can include bis-tris buffer, phosphate, HEPES, MES, Tris, and any combination thereof.

In some embodiments, the rinse solution includes from about 0.05 to about 0.5% (e.g., from about 0.05% to about 0.3%, from about 0.05% to about 0.1%) by volume or by weight of the surfactant. The surfactant can be selected from the group consisting of non-ionic, cationic, anionic, and zwitterionic surfactants. For example, the surfactant can be non-ionic and can include polysorbate 20 (e.g., from about 0.5 mL/L to about two mL/L, from about 0.5 mL/L to about 1.5 mL/L of polysorbate 20).

In some embodiments, the rinse solution includes from about 0.01 to about 0.1% (e.g., from about 0.01% to about 0.06%, from about 0.01% to about 0.02%) by volume or by weight of the surfactant. The surfactant can be selected from the group consisting of non-ionic, cationic, anionic, and zwitterionic surfactants. For example, the surfactant can be non-ionic and can include polysorbate 20 (e.g., from about 0.1 mL/L to about 0.4 mL/L, from about 0.1 mL/L to about 0.3 mL/L of polysorbate 20).

In some embodiments, the rinse solution includes from about 45 to about 55 mL/L (e.g., about 50 mL/L) methanol.

In some embodiments, the rinse solution includes from about 9 to about 11 mL/L (e.g., about 10 mL/L) methanol.

In some embodiments, the rinse solution includes about five g/L polyethylene glycol; about 50 mM HEPES buffer; about one mL/L polysorbate 20; about 15 ppm ProClin 300®; about 50 mL/L methanol; and water. The rinse solution can have a pH of from about 6.6 to about 7.0.

In some embodiments, the rinse solution includes about one g/L polyethylene glycol; about 10 mM HEPES buffer; about 0.2 mL/L polysorbate 20; about 3 ppm ProClin 300®; about 10 mL/L methanol; and water. The rinse solution can have a pH of from about 6.6 to about 7.0.

In some embodiments, the cytological fixative solutions are free of the dye Patent Blue VF (e.g., contain none or less than the amount of Patent Blue VF that is present in the formulations disclosed in WO 2007/117798).

In some embodiments, first cytological staining solutions are free of the dye Patent Blue VF (e.g. contain none or less than the amount of Patent Blue VF that is present in the formulations disclosed in WO 2007/117798).

In some embodiments, second cytological staining solutions are free of the dye Patent Blue VF (e.g. contain none or less than the amount of Patent Blue VF that is present in the formulations disclosed in WO 2007/117798).

In some embodiments, the rinse solutions are free of the dye Patent Blue VF (e.g. contain none or less than the amount of Patent Blue VF that is present in the formulations disclosed in WO 2007/117798).

In some embodiments, the cytological fixative solutions are free of a proteolytic enzyme (e.g., contain none or less than the amount of a proteolytic enzyme that is present in the formulations disclosed in WO 2007/117798).

In some embodiments, first cytological staining solutions are free of a proteolytic enzyme (e.g., contain none or less than the amount of a proteolytic enzyme that is present in the formulations disclosed in WO 2007/117798).

In some embodiments, second cytological staining solutions are free of a proteolytic enzyme (e.g., contain none or less than the amount of a proteolytic enzyme that is present in the formulations disclosed in WO 2007/117798).

In some embodiments, the rinse solutions are free of a proteolytic enzyme (e.g., contain none or less than the amount of a proteolytic enzyme that is present in the formulations disclosed in WO 2007/117798).

In some embodiments, performing a first staining phase includes (i) dispensing a first cytological staining solution into the separation between the substrate and the surface in an amount sufficient to contact the specimen and the surface; (ii) performing at least a second agitation phase, wherein the second agitation phase includes changing the distance between the substrate and surface while the first staining solution is contacting the specimen for the duration of the second agitation phase; and (iii) removing the first staining solution from the separation and the specimen.

In some embodiments, performing a second staining phase includes (i) dispensing a second cytological staining solution into the separation between the substrate and the surface in an amount sufficient to contact the specimen and the surface; (ii) performing at least a third agitation phase, wherein the third agitation phase comprises changing the distance between the substrate and surface while the second staining solution is contacting the specimen for the duration of the third agitation phase; and (iii) removing the second staining solution from the separation and the specimen.

In some embodiments, performing a first rinse phase includes (i) dispensing a rinse solution into the separation between the substrate and the surface in an amount sufficient to contact the specimen and the surface; (ii) performing at least a fourth agitation phase, wherein the fourth agitation phase comprises changing the distance between the substrate and surface while the rinse solution is contacting the specimen for the duration of the fourth agitation phase; and (iii) removing the rinse solution from the separation and the specimen.

In some embodiments, the automated specimen analysis machine includes a substrate arm including a substrate gripper; a first actuator connected to the substrate arm and configured to move the substrate arm between an open position and a specimen processing position; a second actuator arranged and configured to agitate a substrate gripped by the substrate gripper on the substrate arm; a platform having a top surface located opposite the substrate when the substrate arm is in the specimen processing position; and two or more offsets arranged on the top surface of the platform such that when the substrate contacts all of the offsets in the substrate processing position, the substrate and top surface of the platform are substantially parallel and form a separation of at least about 50 microns.

Embodiments of the automated specimen examination system can include any one or more of the features disclosed herein, as appropriate, including any one or more of the features of the specimen preparation apparatus' disclosed herein.

In embodiments of the methods, kits, and systems described herein, one, two, three, or four (e.g., four) of (A), (B), (C), and (D) can apply.

(A) The cytological fixative solution includes Azure B; a surfactant; methanol; and ethylene glycol.

For example, the cytological fixative solution can include about 0.5 g/L to about 5.0 g/L Azure B; about 0.5 mL/L to about 2.0 mL/L polysorbate 20; about 5 mL/L to about 50 mL/L ethylene glycol, propylene glycol, or polypropylene glycol; about 0.1 g/L to about 10 g/L HEPES sodium salt; and methanol.

As another example, the cytological fixative solution can include about 0.8 g/L to about 1.2 g/L Azure B; about 0.8 mL/L to about 1.2 mL/L polysorbate 20; about 9 mL/L to about 11 mL/L ethylene glycol; about 0.25 g/L to about 0.38 g/L HEPES sodium salt; and methanol.

For example, the cytological fixative solution can include about one g/L Azure B; about one mL/L polysorbate 20; about 10 mL/L ethylene glycol; about 0.32 g/L HEPES sodium salt; and methanol.

As another example, the cytological fixative solution can include about one g/L Azure B; about 0.5 mL/L polysorbate 20; about 10 mL/L propylene glycol; about 0.32 g/L HEPES sodium salt; and methanol.

As a further example, the cytological fixative solution can include about one g/L Azure B; about 1.5 mL/L polysorbate 20; about 10 mL/L polypropylene glycol; about 0.32 g/L HEPES sodium salt; and methanol.

Embodiments can include any one or more of the features described above and/or in the Detailed Description and/or in the claims.

(B) The first cytological staining solution includes eosin Y; a buffering agent; a surfactant; sodium chloride; ethylene glycol; and water.

For example, the first cytological staining solution can include about 0.5 g/L to about 5.0 g/L Eosin Y; about 5 mM to about 250 mM bis-tris or phosphate buffer; about 0.5 mL/L to about 2.0 mL/L polysorbate 20; about one g/L to about 20 g/L sodium chloride; about five mL/L to about 50 mL/L ethylene glycol; about 0.2 ppm to about 50 ppm ProClin 300®; acetic acid; and water, wherein the solution has a pH of from about 5.8 to about 6.2.

As another example, the first cytological staining solution can include about 0.6 g/L to about 0.9 g/L Eosin Y; about 45 mM to about 55 mM bis-tris buffer; about 0.8 mL/L to about 1.2 mL/L polysorbate 20; about three g/L to about five g/L sodium chloride; about nine mL/L to about 11 mL/L ethylene glycol; about 10 ppm to about 20 ppm ProClin 300®; acetic acid; and water, wherein the solution has a pH of from about 5.8 to about 6.2.

For example, the first cytological staining solution can include about 0.75 g/L Eosin Y; about 50 mM bis-tris buffer; about one mL/L polysorbate 20; about four g/L sodium chloride; about 10 mL/L ethylene glycol; about 15 ppm ProClin 300®; acetic acid; and water, wherein the solution has a pH of from about 5.8 to about 6.2.

As another example, the first cytological staining solution can include about 0.75 g/L Eosin Y; about 50 mM bis-tris buffer; about 0.5 mL/L polysorbate 20; about six g/L sodium chloride; about 20 mL/L ethylene glycol; about 15 ppm ProClin 300®; acetic acid; and water, wherein the solution has a pH of from about 5.8 to about 6.2.

As a further example, the first cytological staining solution can include about 0.75 g/L Eosin Y; about 50 mM phosphate buffer; about 2.0 mL/L polysorbate 20; about four g/L sodium chloride; about 50 mL/L ethylene glycol; about 15 ppm ProClin 300®; acetic acid; and water, wherein the solution has a pH of from about 5.8 to about 6.2.

Embodiments can include any one or more of the features described above and/or in the Detailed Description and/or in the claims.

(C) The second cytological staining solution includes Azure B; methylene blue; a buffering agent; a surfactant, sodium chloride, and water.

For example, the second cytological staining solution can include about 0.25 to about 2.5 g/L Azure B; about 0.25 g/L to about 2.5 g/L methylene blue; about 5 mM to about 250 mM bis-tris or HEPES buffer; about 0.5 mL/L to about 2.0 mL/L polysorbate 20, about one g/L to about 20 g/L sodium chloride, and about 0.2 ppm to about 50 ppm ProClin 300®; acetic acid; and water, wherein the solution has a pH of from about 6.8 to about 7.2.

As another example, the second cytological staining solution can include about 0.4 to about 0.6 g/L Azure B; about 0.4 g/L to about 0.5 g/L methylene blue; about 45 mM to about 55 mM bis-tris buffer; about 0.8 mL/L to about 1.2 mL/L polysorbate 20, about 1.8 g/L to about 2.2 g/L sodium chloride, and about 10 ppm to about 20 ppm ProClin 300®; acetic acid; and water, wherein the solution has a pH of from about 6.8 to about 7.2.

For example, the second cytological staining solution can include about 0.5 g/L Azure B; about 0.45 g/L methylene blue; about 50 mM bis-tris buffer; about one mL/L polysorbate 20, about two g/L sodium chloride, and about 15 ppm ProClin 300®; acetic acid; and water, wherein the solution has a pH of from about 6.8 to about 7.2.

As another example, the second cytological staining solution can include about 0.5 g/L Azure B; about 0.45 g/L methylene blue; about 50 mM HEPES buffer; about 0.5 mL/L polysorbate 20, about two g/L sodium chloride, and about 15 ppm ProClin 300®; acetic acid; and water, wherein the solution has a pH of from about 6.8 to about 7.2.

As a further example, the second cytological staining solution can include about 0.5 g/L Azure B; about 0.45 g/L methylene blue; about 50 mM HEPES buffer; about one mL/L polysorbate 20, about one g/L sodium chloride, and about 15 ppm ProClin 300®; acetic acid; and water, wherein the solution has a pH of from about 6.8 to about 7.2.

The solution can have a pH of from about 6.8 to about 7.2.

Embodiments can include any one or more of the features described above and/or in the Detailed Description and/or in the claims.

(D) The rinse solution for an automated specimen preparation apparatus includes polyethylene glycol; a buffering agent; a surfactant; methanol; and water.

For example, the rinse solution can include about 0.2 g/L to about ten g/L polyethylene glycol; about 1 mM to about 250 mM HEPES, MES, or bis-tris buffer; about 0.1 mL/L to about 2.40 mL/L polysorbate 20; about 0.04 ppm to about 50 ppm ProClin 300®; about 9 mL/L to about 200 mL/L methanol; and water, wherein the rinse solution has a pH of from about 6.6 to about 7.0.

As another example, the rinse solution can include about one g/L to about ten g/L polyethylene glycol; about 5 mM to about 250 mM HEPES, MES, or bis-tris buffer; about 0.5 mL/L to about 2.0 mL/L polysorbate 20; about 0.2 ppm to about 50 ppm ProClin 300®; about 10 mL/L to about 200 mL/L methanol; and water, wherein the rinse solution has a pH of from about 6.6 to about 7.0.

As a further example, the rinse solution can include about 4.5 g/L to about 5.5 g/L polyethylene glycol; about 45 mM to about 55 mM HEPES buffer; about 0.8 mL/L to about 1.2 mL/L polysorbate 20; about 10 ppm to about 20 ppm ProClin 300®; about 45 mL/L to about 55 mL/L methanol; and water, wherein the rinse solution has a pH of from about 6.6 to about 7.0.

For example, the rinse solution includes about five g/L polyethylene glycol; about 50 mM HEPES buffer; about one mL/L polysorbate 20; about 15 ppm ProClin 300®; about 50 mL/L methanol; and water, wherein the rinse solution has a pH of from about 6.6 to about 7.0.

As another example, the rinse solution includes about 10 g/L polyethylene glycol; about 50 mM MES buffer; about one mL/L polysorbate 20; about 15 ppm ProClin 300®; about 50 mL/L methanol; and, wherein the rinse solution has a pH of from about 6.6 to about 7.0.

As a further example, the rinse solution includes about 10 g/L polyethylene glycol; about 50 mM bis-tris buffer; about 0.5 mL/L polysorbate 20; about 15 ppm ProClin 300®; about 50 mL/L methanol; and water, wherein the rinse solution has a pH of from about 6.6 to about 7.0.

For example, the rinse solution can include about 0.2 g/L to about two g/L polyethylene glycol; about one mM to about 50 mM HEPES buffer; about 0.16 mL/L to about 0.24 mL/L polysorbate 20; about 0.04 ppm to about 10 ppm ProClin 300®; about 9 mL/L to about 11 mL/L methanol; and water, wherein the rinse solution has a pH of from about 6.6 to about 7.0.

As another example, the rinse solution can include about 0.9 g/L to about 1.1 g/L polyethylene glycol; about 9 mM to about 11 mM HEPES buffer; about 0.16 mL/L to about 0.24 mL/L polysorbate 20; about 2 ppm to about 10 ppm ProClin 300®; about 9 mL/L to about 11 mL/L methanol; and water, wherein the rinse solution has a pH of from about 6.6 to about 7.0.

In still another example, the rinse solution includes about one g/L polyethylene glycol; about 10 mM HEPES buffer; about 0.2 mL/L polysorbate 20; about 3 ppm ProClin 300®; about 10 mL/L methanol; and water, wherein the rinse solution has a pH of from about 6.6 to about 7.0.

As used herein, when a solution is "free" of one or more substances, this means that the solution contain less than 5% (e.g., less than 4%, less than 3%, less than 2%, less than 1%, 0% (w/w or w/v or v/v)) of the indicated one or more substances as determined by HPLC, UV spectroscopy, electrophoresis, and/or enzyme assay detection.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

Like reference symbols in the various drawings indicate like elements.

DETAILED DESCRIPTION

Figure 1:
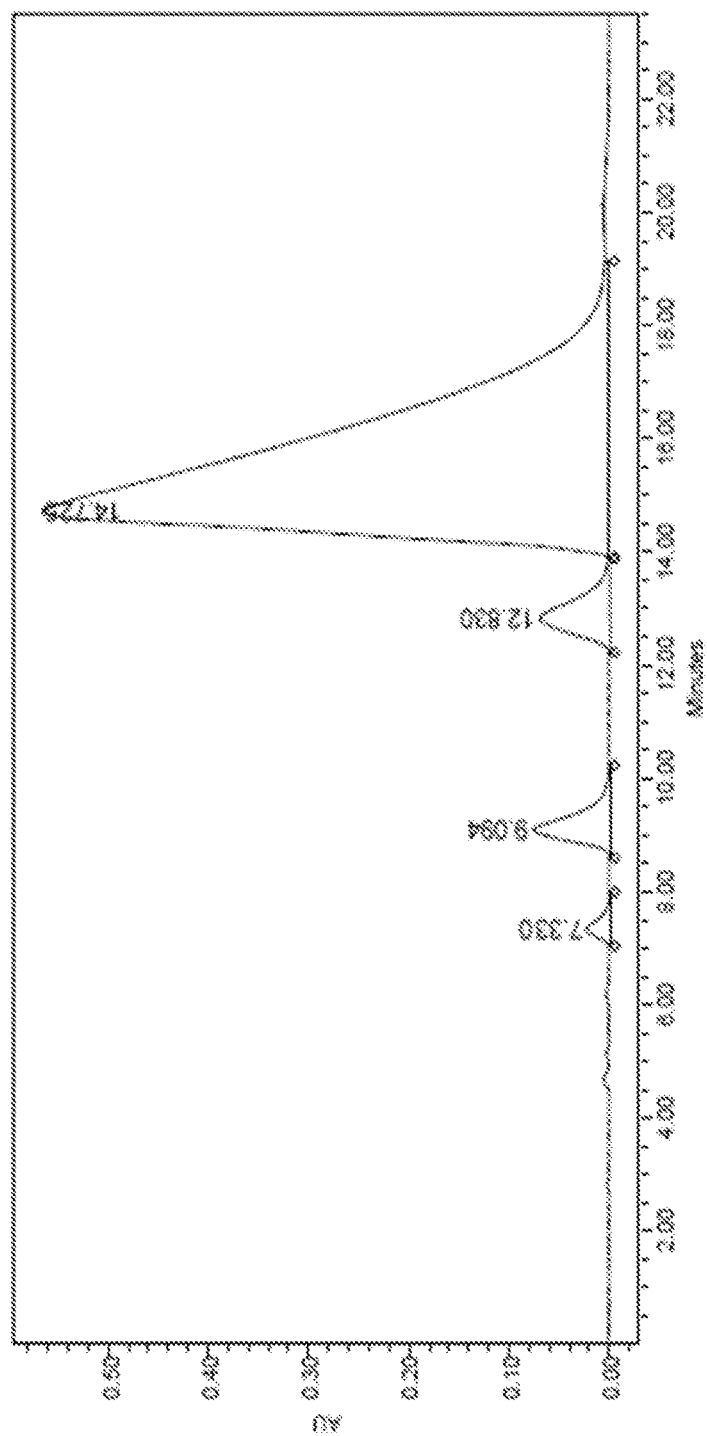
FIG. 1 is an HPLC chromatograph of an embodiment of a fixative solution.

Disclosed herein are formulations, methods, and systems for automated specimen processing. The automated specimen processing methods and systems described herein provide advantages over manual and other automated processing methods, including enhanced processing speed using minimal reagent volumes with a concurrent highly uniform staining that significantly reduces the variability associated with the application of stains, fixatives, and other reagents when specimens are processed by hand or by other systems. The fixative, stain, and rinse solutions can provide enhanced contrast to the specimen, and can be easily dispensed from the automated specimen processing systems. Further, the fixative, stain, and rinse solutions can provide improved cell identification and cell classification over conventional fixative, stain, and rinse solutions.

Conventional fixative, staining, and rinsing solutions typically provide poor staining results, such as light-colored staining or non-specific staining of biological samples (e.g., non-specific staining of cytoplasms); or require large volumes of processing fluids. The formulations disclosed herein permit high contrast and selective staining of biological samples with low volumes of processing fluids, for example, when used with the automated specimen processing systems.

Furthermore, conventional automated processing methods typically have relatively high processing throughput while at the same time consuming large volumes of processing fluids, or have relatively low processing throughput while consuming reduced volumes of fluids. For many applications, however, both high throughput operation and low fluid consumption are desirable. By maintaining high throughput, specimens can be efficiently processed and examined. By keeping fluid consumption low, the amount of processing waste is reduced along with the required volume of processing reagents, keeping operating costs low. The formulations, systems, and methods disclosed herein permit rapid automated processing of specimens (e.g., more than 100 specimens per hour by a single machine) using low volumes of processing fluids (e.g., less than about 1 mL of fluids per specimen, less than about 1.5 mL of fluids per specimen, less than about 2 mL of fluids per specimen), while producing highly uniform and repeatable results.

Formulations for Use with Specimen Preparation Systems

A fixative solution, one or more staining solutions, and a rinse solution are provided herein, which can be used in an automated specimen preparation system. Each of the solutions can have a specific formulation. For example, the fixative solution can include a cytological dye, a surfactant, an organic solvent, an agent to minimize non-specific binding, and a buffering agent. A first aqueous staining solution can include a cytological dye, a buffering agent, a surfactant, a salt, an agent to minimize non-specific binding, and an antimicrobial agent. A second aqueous staining solution can include one or more cytological dye(s), a buffering agent, a surfactant, a salt, and an antimicrobial agent. The rinse solution can include a buffering agent, a surfactant, an antimicrobial, an organic solvent, and a water-soluble polymer. The formulation components can be analyzed for purity and/or purified by HPLC. The formulations can also include an acid for adjusting the pH. Each formulation is described in greater detail below.

Fixative Solution

Fixatives that can be included in a fixative solution include chemicals used for protecting biological samples from decay. Such fixatives can impede biochemical reactions occurring in the specimen and increase the mechanical strength and stability of the specimen. Various fixatives can be included in a fixative solution, e.g., methanol, ethanol, isopropanol, acetone, formaldehyde, glutaraldehyde, EDTA, surfactants, metal salts, metal ions, urea, and amino compounds. In some embodiments, the fixative solution includes an organic solvent or a fixation agent that can precipitate, crosslink, or otherwise preserve components (e.g., proteins) within a cell for imaging purposes. For example, the fixation agent can include an organic solvent, such as one or more alcohols including methanol, ethanol, and isopropanol, or other organic solvent such as acetone and ether. In some embodiments, the fixative solution includes an organic solvent such as methanol. The organic solvent can have an ACS grade of less than about 0.1% water (e.g., less than about 0.05% water, less than about 0.01% water). The organic solvent can be present in the solution in an amount that is the remaining balance after other components have been added to the fixative solution. The organic solvent can serve as a drying agent for a specimen and can displace water from the specimen.

In some embodiments, the fixative solution includes a cytological dye. The dye can increase the staining of a specimen and can include, for example, Azure B, methylene blue, eosin, thiazine stains, and fluorescein derivatives. The dye can be at least about 80% pure (e.g., at least about 85% pure, at least about 90% pure, at least about 95% pure, or at least about 99% pure). A representative HPLC chromatogram of azure B is shown, for example, in FIG. 1. The dye can have a concentration of from approximately 0.5 g/L (e.g., approximately 0.75 g/L, approximately one g/L, approximately two g/L, approximately three g/L, or approximately four g/L) to approximately five g/L (e.g., approximately four g/L, approximately three g/L, approximately two g/L, approximately one g/L, or approximately 0.75 g/L) in the fixative solution. For example, the fixative solution can include approximately one g/L of Azure B. In some embodiments, the fixative solution can include approximately 0.8 g/L of Azure B.

Figure 13A:
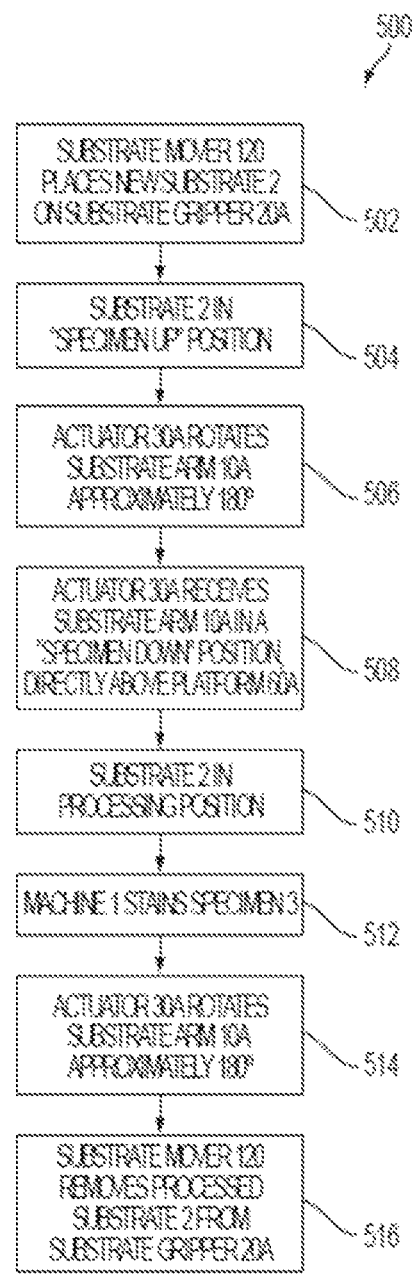
FIG. 13A is a flow chart showing a series of steps for moving substrate arms from an open position to closed (specimen processing) position.
Figure 13B:
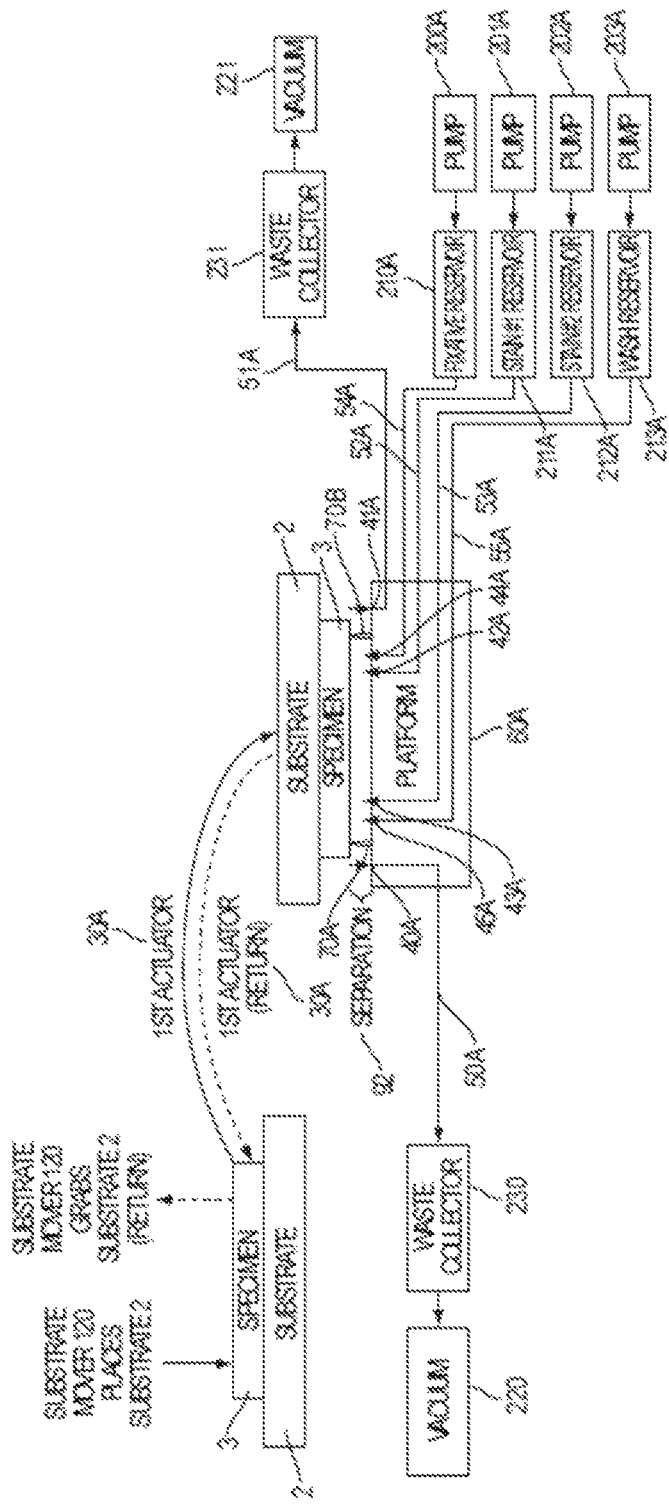
FIG. 13B is a schematic diagram of an embodiment of a specimen preparation apparatus as described herein.

The fixative solution can include a surfactant. Without wishing to be bound by any theory, it is believed that a surfactant reduces the surface tension of a solvent, and provides good spreadability of a solution onto a sample substrate at separation 92 as shown in FIG. 13B. In some embodiments, the surfactant is non-ionic, and can minimize the likelihood of precipitation from solution that can result from ionic interactions with components within a formulation, such as an ionically charged dye. A solution having little or no precipitates can be more easily discharged from a dispensing nozzle and can reduce the likelihood that the dispensing nozzle will clog or that a liquid flow is diminished over time. In some embodiments, the surfactant can decrease the likelihood of non-specific binding of components within a fixative solution to the specimen, which can minimize imaging artifacts.

The fixative solution can include from approximately 0.05% (e.g., from approximately 0.075%, from approximately 0.1%, from approximately 0.2%, from approximately 0.3%, or from approximately 0.4%) to approximately 0.5% (e.g., to approximately 0.4%, to approximately 0.3%, to approximately 0.2%, to approximately 0.1%, or to approximately 0.075%) by volume of a liquid surfactant or by weight of a solid surfactant. In some embodiments, the fixative solution can include from approximately 0.5 to approximately two mL/L of a surfactant (e.g., a non-ionic surfactant). For example, the fixative solution can include approximately one mL/L of polysorbate 20 (e.g., Tween 20).

The surfactant may be non-ionic, cationic, anionic or zwitterionic. Mixtures of surfactants may also be used. Exemplary classes of surfactants include alcohol ether sulfates, alcohol sulfates, alkanolamides, alkyl sulfonates, amine oxides, amphoteric surfactants, anionic surfactants, betaine derivatives, cationic surfactants, disulfonates, dodecylbenzene, sulfonic acid, ethoxylated alcohols, ethoxylated alkyl phenols, ethoxylated fatty acids, glycerol esters hydrotropes, lauryl sulfates, mono and diglycerides, non-ionic surfactants, phosphate esters, quaternary surfactants, and sorbitan derivatives.

Examplary non-ionic surfactants include, for example, BigCHAP(N,N-Bis[3-(D-gluconamido)propyl]cholamide), Bis(polyethylene glycol bis[imidazoyl carbonyl]), Brij® 30 (Polyoxyethylene 4 lauryl ether) Brij® 35 (Polyoxyethylene 23 lauryl ether), Brij® 52 (Polyoxyethylene 2 cetyl ether), Brij® 56 (Polyoxyethylene 10 cetyl ether), Brij® 58 (Polyoxyethylene 20 cetyl ether), Brij® 72 (Polyoxyethylene 2 stearyl ether), Brij® 76 (Polyoxyethylene 10 stearyl ether), Brij® 78 (Polyoxyethylene 20 stearyl ether), Brij® 92 (Polyoxyethylene 2 oleyl ether), Brij® 97 (Polyoxyethylene 10 oleyl ether), Brij® 98 (Polyoxyethylene 20 oleyl ether), Brij® 700 (Polyoxyethylene 100 stearyl ether), Cremophor® EL (castor oil/ethylene oxide polyether), Decaethylene glycol monododecyl ether, octanoyl-N-methylglucamide (MECA-8), decanoyl-N-methylglucamide (MECA-10), n-octylglucoside, n-decylglucoside, isotridecyl-poly (ethyleneglycolether)$_n$, N-Decanoyl-N-methylglucamine, n-Decyl α-Dglucopyranoside, Decyl β-D-maltopyranoside, n-Dodecanoyl-N-methylglucamide, n-Dodecyl α-D-maltoside, n-Dodecyl β-D-maltoside, Heptaethylene glycol monodecyl ether, Heptaethylene glycol monotetradecyl ether, n-Hexadecyl β-D-maltoside, Hexaethylene glycol monododecyl ether, Hexaethylene glycol monohexadecyl ether, Hexaethylene glycol monooctadecyl ether, Hexaethylene glycol monotetradecyl ether, Igepal CA-630 (Octylphenyl-polyethylene glycol), Igepal® CA-210 (polyoxyethylene(2) isooctylphenyl ether), Igepal® CA-520 (polyoxyethylene(5) isooctylphenyl ether), Igepal® CO-630 (polyoxyethylene(9)nonylphenyl ether), Igepal® CO-720 (polyoxyethylene(12) nonylphenyl ether), Igepal® CO-890 (polyoxyethylene(40) nonylphenyl ether), Igepal® CO-990 (polyoxyethylene(100) nonylphenyl ether), Igepal® DM-970 (polyoxyethylene(150) dinonylphenyl ether), Methy 1-6-O—(N-heptylcarbamoyl)-α-D-glucopyranoside, Nonaethylene glycol monododecyl ether, N-Nonanoyl-N-methylglucamine, Octaethylene glycol monodecyl ether, Octaethylene glycol monododecyl ether, Octaethylene glycol monohexadecyl ether, Octaethylene glycol monooctadecyl ether, Octaethylene glycol monotetradecyl ether, Octyl-β-D-glucopyranoside, Pentaethylene glycol monodecyl ether, Pentaethylene glycol monododecyl ether, Pentaethylene glycol monohexadecyl ether, Pentaethylene glycol monohexyl ether, Pentaethylene glycol monooctadecyl ether, Pentaethylene glycol monooctyl ether, Polyethylene glycol diglycidyl ether, Polyethylene glycol ether W-1, Polyoxyethylene 10 tridecyl ether, Polyoxyethylene 100 stearate, Polyoxyethylene 20 isohexadecyl ether, Polyoxyethylene 20 oleyl ether, Polyoxyethylene 40 stearate, Polyoxyethylene 50 stearate, Polyoxyethylene 8 stearate, Polyoxyethylene bis(imidazolyl carbonyl), Polyoxyethylene 25 propylene glycol stearate, Saponin, Span® 20 (Sorbitan monolaurate), Span® 40 (Sorbitan monopalmitate), Span® 60 (Sorbitan mono stearate), Span® 65 (Sorbitan tristearate), Span® 80 (Sorbitan monooleate), Span® 85 (Sorbitan trioleate), Tergitol in any form (including Types 15-S-5,15-S-7,15-S-9,15-S-12, 15-S-30, NP-4, NP-7, NP-9, NP-10, NP-40, NPX (Imbentin-N/63), TMN-3 (Polyethylene glycol trimethylnonyl ether), TMN-6 (Polyethylene glycol trimethylnonyl ether), TMN-10 (Polyethylene glycol trimethylnonyl ether), MIN FOAM 1x, and MIN FOAM 2x), Tetradecyl-β-D-maltoside, Tetraethylene glycol monodecyl ether, Tetraethylene glycol monododecyl ether, Tetraethylene glycol monotetradecyl ether, Triethylene glycol monodecyl ether, Triethylene glycol monododecyl ether, Triethylene glycol monohexadecyl ether, Triethylene glycol monooctyl ether, Triethylene glycol monotetradecyl ether, Triton® CF-21, Triton® CF-32, Triton® DF-12, Triton® DF-16, Triton® GR-5M, Triton® N-101 (Polyoxyethylene branched nonylphenyl ether), Triton® QS-15, Triton® QS-44, Triton® RW-75 (Polyethylene glycol 260 mono (hexadecyl/octadecyl)ether and 1-Octadecanol), Triton® X-100 (Polyethylene glycol tert-octylphenyl ether), Triton® X-102, Triton® X-15, Triton® X-151, Triton® X-200, Triton® X-207, Triton® X-114, Triton® X-165, Triton® X-305, Triton® X-405 (polyoxyethylene (40) isooctylphenyl ether), Triton® X-405 reduced (polyoxyethylene (40) isooctylcyclohexyl ether), Triton® X-45 (Polyethylene glycol 4-tert-octylphenyl ether), Triton® X-705-70, TWEEN® in any form (including TWEEN® 20 (Polyoxyethylenesorbitan monolaurate, or polysorbate 20), TWEEN® 21 (Polyoxyethylenesorbitan monolaurate), TWEEN® 40 (polyoxyethylene(20) sorbitan monopalmitate), TWEEN® 60 (Polyethylene glycol sorbitan monostearate), TWEEN® 61 (Polyethylene glycol sorbitan monostearate), TWEEN® 65 (Polyoxyethylenesorbitan Tristearate), TWEEN® 80 (Polyoxyethylenesorbitan monooleate), TWEEN® 81 (Polyoxyethylenesorbitan monooleate), and TWEEN® 85 (polyoxyethylene(20) sorbitan trioleate)), Tyloxapol (4-(1,1,3,3-tetramethylbutyl) phenol polymer with formaldehyde and oxirane), and n-Undecyl β-D-glucopyranoside.

Exemplary anionic surfactants include Chenodeoxycholic acid, Cholic acid, Dehydrocholic acid, Deoxycholic acid, Digitonin, Digitoxigenin, N,N-Dimethyldodecylamine N-oxide, Sodium docusate, Sodium glycochenodeoxycholate, Glycocholic acid, Glycodeoxycholic acid, Glycolithocholic acid 3-sulfate disodium salt, Glycolithocholic acid ethyl ester, N-Lauroylsarcosine, Lithium dodecyl sulfate, Lugol (Iodine Potassium Iodide), Niaproof (2-Ethylhexyl sulfate sodium salt), Niaproof 4 (7-Ethyl-2-methyl-4-undecyl sulfate sodium salt), optionally substituted alkylsulfonate salts (including salts of 1-butanesulfonate, pentanesulfonate, hexanesulfonate, 1-Octanesulfonate, 1-decanesulfonate, 1-dodecanesulfonate, 1-heptanesulfonate, 1-heptanesulfonate, 1-nonanesulfonate, 1-propanesulfonate, and 2-bromoethanesulfonate, especially the sodium salts), Sodium cholate, Sodium deoxycholate, optionally substituted Sodium dodecyl sulfate, Sodium octyl sulfate, Sodium taurocholate, Sodium taurochenodeoxycholate, Sodium taurohyodeoxycholate, Taurolithocholic acid 3-sulfate disodium salt, Tauroursodeoxycholic acid sodium salt, Trizma® dodecyl sulfate, Ursodeoxycholic acid. The anionic surfactant can be provided in acid or salt form, or both.

Exemplary cationic surfactants include Alkyltrimethylammonium bromide, Benzalkonium chloride, Benzyldimethylhexadecylammonium chloride, Benzyldimethyltetradecylammonium chloride, Benzyldodecyldimethylammonium bromide, Benzyltrimethylammonium tetrachloroiodate, Dimethyldioctadecylammonium bromide, Dodecylethyldimethylammonium bromide, Dodecyltrimethylammonium bromide, Ethylhexadecyldimethylammonium bromide, Girard's reagent T, Hexadecyltrimethylammonium bromide, N,N',N'-Polyoxyethylene(10)-N-tallow-1,3-diaminopropane, Thonzonium bromide, and Trimethyl(tetradecyl) ammonium bromide.

Exemplary zwitterionic surfactants include CHAPS (3-{(3-cholamidopropyl)-dimethylammonio}-1-propane-sulfonate), CHAPSO (3-{(3-cholamidopropyl)dimethyl-ammonio}-2-hydroxy-1-propane-sulfonate), 3-(Decyldimethylammonio) propanesulfonate, 3-(Dodecyldimethylammonio) propanesulfonate, 3-(N,N-Dimethylmyristylammonio) propanesulfonate, 3-(N,N-Dimethyloctadecylammonio) propanesulfonate, 3-(N,N-Dimethyloctylammonio) propanesulfonate, and 3-(N,N-Dimethylpalmitylammonio) propanesulfonate.

The surfactant includes those known or discoverable in the art. The surfactant can be synthesized or can be obtained commercially from any of a variety of vendors (e.g., Sigma Aldrich Corp., St. Louis, Mo., USA, www.sigmaaldrich.com). A given surfactant may be tested for its ability to reduce artifacts by evaluating a sample treated with test surfactant against a sample processed without a surfactant treatment, and against a sample processed with a surfactant or other positive control treatment known to reduce staining artifacts. A given surfactant may be tested for its ability to reduce precipitation of a formulation's components by visually inspecting a solution containing a surfactant against a solution without surfactant, after the solutions have been allowed to rest for at least two weeks.

The fixative solution can include an agent to minimize non-specific binding of a dye to cellular components, such as ethylene glycol, propylene glycol, and/or polyethylene glycol. In some embodiments, the fixative solution can include from approximately 0.5% (e.g., approximately 0.75%, approximately one %, approximately two %, approximately three %, or approximately four %) to approximately five % (e.g., approximately four %, approximately three %, approximately two %, approximately one %, or approximately 0.75%) by volume of a liquid non-specific binding minimizing agent, or by weight of a solid non-specific binding minimizing agent. For example, the fixative solution can include from approximately five mL/L (e.g., approximately 10 mL/L, approximately 15 mL/L, approximately 20 mL/L, approximately 25 mL/L, approximately 30 mL/L, approximately 35 mL/L, approximately 40 mL/L, or approximately 45 mL/L) to approximately 50 mL/L (e.g., approximately 45 mL/L, approximately 40 mL/L, approximately 35 mL/L, approximately 30 mL/L, approximately 25 mL/L, approximately 20 mL/L, approximately 15 mL/L, or approximately 10 mL/L) ethylene glycol. In some embodiments, the fixative solution includes approximately 10 mL/L (e.g., approximately 15 mL/L, approximately 20 mL/L, or approximately 25 mL/L) ethylene glycol.

The fixative solution can include a buffering agent. Examples of buffering agents include HEPES buffer (e.g., a HEPES sodium salt and/or a HEPES free acid), MES, vis-tris, and other organic buffers. The fixative solution can include from approximately 0.5 mM (e.g., approximately one mM, approximately three mM, approximately five mM, approximately seven mM, or approximately nine mM) to approximately 10 mM (e.g., approximately nine mM, approximately seven mM, approximately five mM, approximately three mM, or approximately one mM) of a buffering agent. For example, the fixative solution can include approximately 1.5 mM (e.g., approximately two mM or approximately one mM) HEPES sodium salt. The fixative solution can include from approximately 0.1 g/L to approximately 10 g/L HEPES (e.g., from approximately 0.5 g/L to approximately 10 g/L, from approximately 0.25 g/L to approximately 0.38, approximately 0.32 g/L).

The fixative solution can have a pH of from approximately 6 to approximately 8 (e.g., a pH of from approximately 6.3 to approximately 7.7, a pH of from approximately 6.5 to approximately 7.5, a pH of from approximately 6.7 to approximately 7.3, a pH of from approximately 6.8 to approximately 7.2, a pH of from approximately 6.9 to approximately 7.1, or a pH of approximately 7.0) when diluted in water at a ratio of about 1:10 fixative solution to water. In some embodiments, the fixative can have an absorbance of approximately from 0.1 to one (e.g., approximately from 0.1 to 0.8, approximately from 0.1 to 0.7, approximately from 0.1 to 0.5, approximately from 0.1 to 0.4, approximately from 0.1 to 0.3, approximately from 0.15 to 0.3, approximately from 0.15 to 0.2, approximately from 0.185 to 0.205, approximately 0.19, or approximately 0.2) at a peak wavelength of from about 640 to about 650 nm (e.g., about 646 to about 648 nm) at a dilution of 1:1000 fixative solution to water.

As an example, to make the fixative solution, an organic solvent, such as methanol, can first be added to a mixing vessel to less than 100% (e.g., approximately 90%) of the final desired volume. Calculated amounts of a non-specific binding minimizer agent (e.g., ethylene glycol), a surfactant (e.g., polysorbate 20), a cytological dye (e.g., Azure B), and a buffering agent (e.g., HEPES sodium salt) can be added to the methanol. Further methanol can be added to bring solution to its final desired volume. The mixture can be mixed with a magnetic stir plate/stir bar and/or an impeller for a minimum of about 30 minutes. After mixing, a 1:10 dilution of the fixative solution in distilled water can be prepared, and a pH reading can be carried out using a pH meter (e.g., a Mettler pH meter). In some embodiments, if the pH is not within a desired range, then further buffering agent can be added to the undiluted fixative solution until a 1:10 dilution of the fixative solution in distilled water reaches the desired pH.

Figure 2:
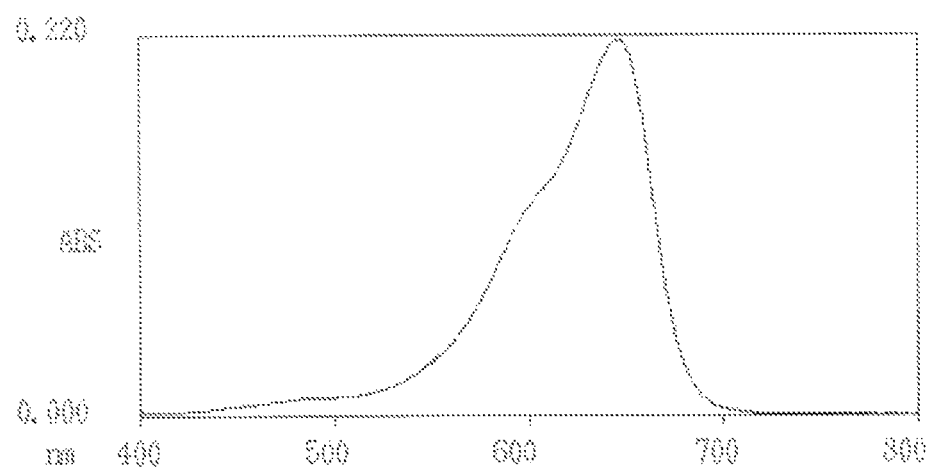
FIG. 2 is a UV-Vis absorption spectrum of an embodiment of a fixative solution.

Fixative solution absorbance can be measured using a UV-spectrophotometer (e.g., a Hitachi UV-spectrophotometer). A baseline can first be run on the spectrophotometer. For example, a 10 mL sample of the fixative solution can be filtered through a 0.45 µm syringe filter, the solution can be diluted 1:1000 with distilled water and run on the spectrophotometer at between approximately 500 to approximately 700 nm. The absorbance at about 640 to about 650 nm can be recorded. A representative UV-Vis absorption spectrum of a fixative solution including azure B is shown, for example, in FIG. 2. If necessary, additional cytological dye can be added to the fixative solution to bring the absorbance to a desired range. If additional cytological dye is added to the fixative solution, the solution is mixed for a minimum of about 30 minutes, and the measurement process (e.g., filtering a 10 mL aliquot, diluting the aliquot in distilled water at a ratio of 1:1000, and taking an absorbance measurement) is repeated. The pH of the solution can also be re-measured and adjusted (if necessary) by the method described above.

Finally, the fixative solution may be filtered through a 0.45 µm filter to remove any particulates before bottling. In some embodiments, a finer or coarser filter can be used. For example, a 0.1 to one µm filter (e.g., a 0.2 µm filter, a 0.4 µm filter, or a 0.8 µm filter) can be used to remove any microorganisms and/or particulates in the fixative solution. In some embodiments, the fixative can be stored in a 500 mL bottle and filled to 396 g±1 g, as measured by a balance. The pH of the final product can be measured, if desired. In some embodiments, a fixative solution's HPLC chromatogram can be obtained, for example, to assess fixative solution purity.

In some embodiments, the fixative solution includes a HEPES buffer (e.g., HEPES sodium salt and/or HEPES free acid) as it is soluble in methanol, is compatible with Azure B, and/or can adjust pH to about 7.8. Azure B can preferentially stain certain cellular components (e.g., a cell nucleus, basophils, cytoplasm, granules, etc.) to provide enhanced contrast. Polysorbate 20 can enhance spreadability of the fixative solution across a substrate (e.g., a microscope slide), and/or can prime a nozzle for delivery of subsequent aqueous solutions. Ethylene glycol can decrease non-specific binding of a dye to cell components (e.g., chromatin to provide lighter colored nucleoli compared to a nucleus) so as to provide better contrast in a stained specimen.

For example, the cytological fixative solution can include about 0.5 g/L to about 5.0 g/L Azure B; about 0.5 mL/L to about 2.0 mL/L polysorbate 20; about 5 mL/L to about 50 mL/L ethylene glycol, propylene glycol, or polypropylene glycol; about 0.1 g/L to about 10 g/L HEPES sodium salt; and methanol.

As another example, the cytological fixative solution can include about 0.8 g/L to about 1.2 g/L Azure B; about 0.8 mL/L to about 1.2 mL/L polysorbate 20; about 9 mL/L to about 11 mL/L ethylene glycol; about 0.25 g/L to about 0.38 g/L HEPES sodium salt; and methanol.

For example, the cytological fixative solution can include about one g/L Azure B; about one mL/L polysorbate 20; about 10 mL/L ethylene glycol; about 0.32 g/L HEPES sodium salt; and methanol.

As another example, the cytological fixative solution can include about one g/L Azure B; about 0.5 mL/L polysorbate 20; about 10 mL/L propylene glycol; about 0.32 g/L HEPES sodium salt; and methanol.

As a further example, the cytological fixative solution can include about one g/L Azure B; about 1.5 mL/L polysorbate 20; about 10 mL/L polypropylene glycol; about 0.32 g/L HEPES sodium salt; and methanol.

First and Second Staining Solutions

Figure 3:
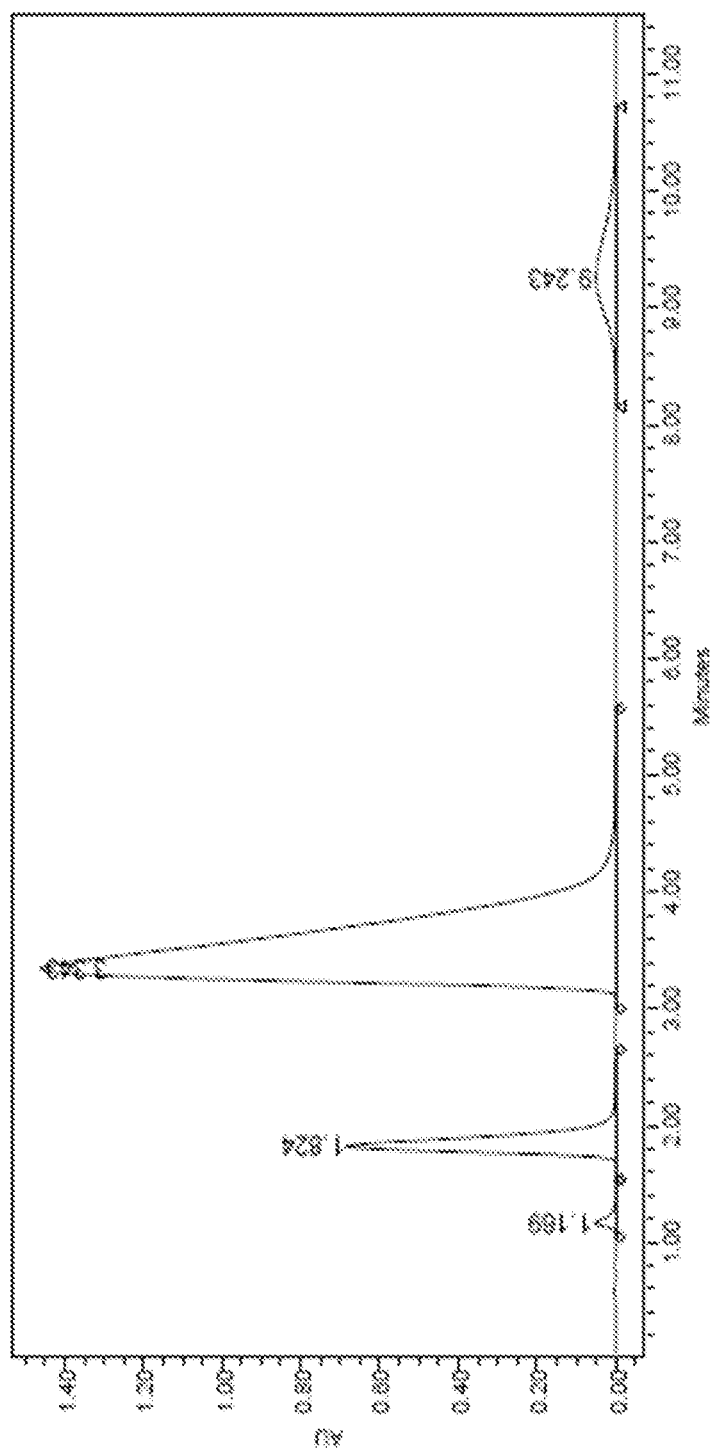
FIG. 3 is an HPLC chromatograph of an embodiment of a first staining solution.

Generally, the first staining solution can be an aqueous solution. The solvent can include distilled water or deionized water. The first staining solution includes a cytological dye. The first staining solution can provide a red stain. The dye can increase the staining of a specimen and can include, for example, eosin Y, and fluorescein derivatives. In some embodiments, eosin Y can stain the cytoplasm and the nuclei of cells within a specimen prepared, for example, from a blood sample. In some embodiments, eosinophils and neutrophils are preferentially stained with eosin Y. The dye can be at least about 80% pure (e.g., at least about 85% pure, at least about 90% pure, at least about 95% pure, or about 100% pure). A representative HPLC chromatogram of Eosin Y is shown, for example, in FIG. 3. The dye can have a concentration of from approximately 0.5 g/L (e.g., approximately 0.75 g/L, approximately one g/L, approximately two g/L, approximately three g/L, or approximately four g/L) to approximately five g/L (e.g., approximately four g/L, approximately three g/L, approximately two g/L, approximately one g/L, or approximately 0.75 g/L) in the first staining solution. For example, the first staining solution can include approximately 0.75 g/L (e.g., approximately one g/L, approximately two g/L, approximately three g/L, approximately four g/L, or approximately five g/L) eosin Y.

Figure 5:
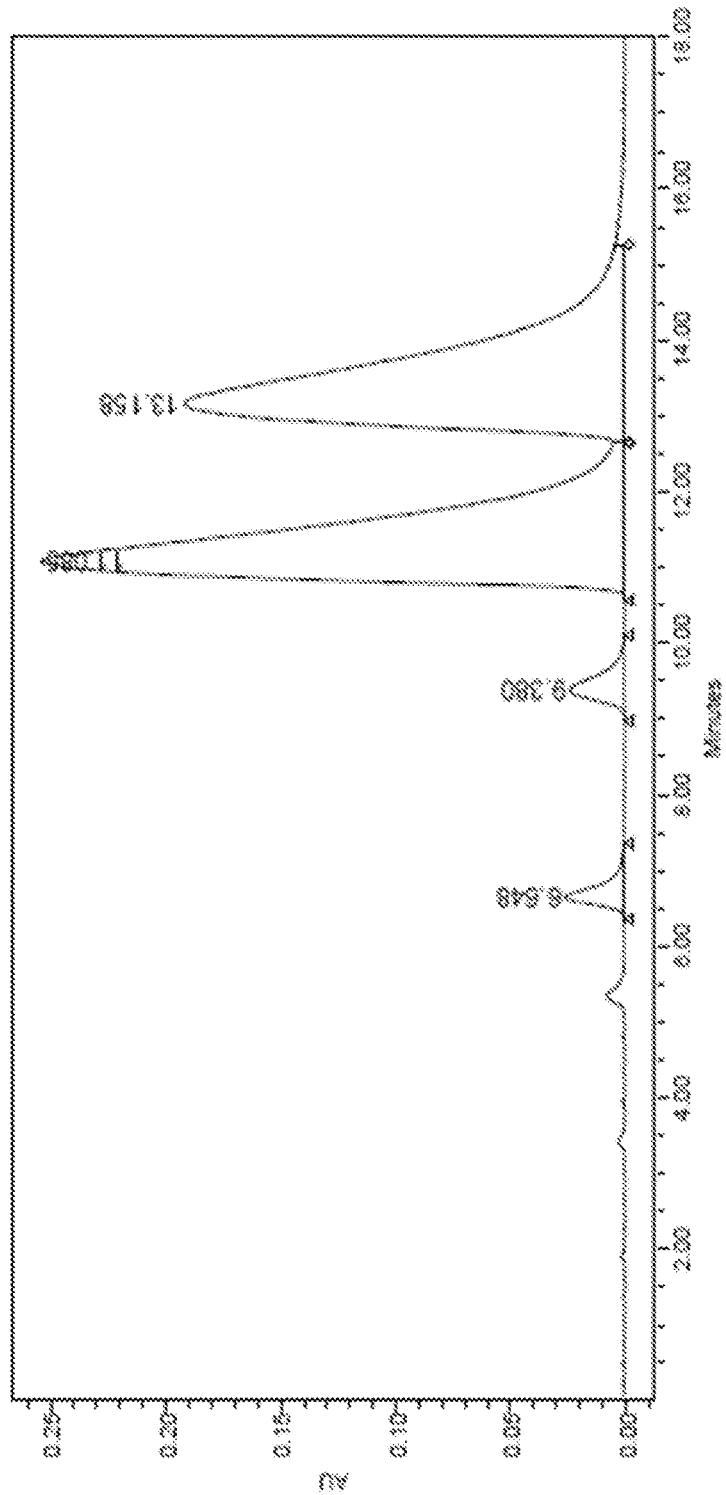
FIG. 5 is an HPLC chromatograph of an embodiment of a second staining solution.

Generally, the second staining solution can be an aqueous solution. The solvent can include distilled water or deionized water. The second staining solution can include two or more cytological dyes. The second staining solution can provide a blue stain. The dyes can increase the staining of a specimen and can include, for example, at least two of azure B, methylene blue, and/or other thiazine dyes. In some embodiments, azure B can preferentially stain a cell nucleus, while methylene blue can primarily stain the cytoplasm and to a minor amount, the nucleus of cells in a specimen prepared, for example, from a blood sample. The dyes can each independently be at least about 80% pure (e.g., at least about 85% pure, at least about 90% pure, at least about 95% pure, or about 100% pure). Each dye can independently have a concentration of from approximately 0.25 g/L (e.g., approximately 0.3 g/L, approximately 0.4 g/L, approximately 0.45 g/L, approximately 0.5 g/L, approximately 0.75 g/L, approximately one g/L, approximately 1.5 g/L, or approximately two g/L) to approximately 2.5 g/L (e.g., approximately two g/L, approximately 1.5 g/L, approximately one g/L, approximately 0.75 g/L, or approximately 0.5 g/L, approximately 0.45 g/L, approximately 0.4 g/L, or approximately 0.3 g/L) in the second staining solution. For example, the second staining solution can include approximately 0.5 g/L azure B and approximately 0.45 g/L methylene blue hydrate. In some embodiments, the second staining solution can include approximately 1:4 to approximately 4:1 (e.g., approximately 3:1, approximately 2:1, approximately 1:1, approximately 1:2, or approximately 1:3) ratio of two dyes, as assessed by the area under the largest HPLC peak for each of the dyes when the absorbance is monitored at a wavelength corresponding to the maximum absorbance for each dye (e.g., at about 630 nm and about 660 nm). A representative HPLC chromatograph of a second staining solution including an approximately 1:1 ratio of azure B to methylene blue is shown, for example, in FIG. 5.

The first and second staining solutions can each independently include a surfactant. Without wishing to be bound by any theory, it is believed that a surfactant reduces the surface tension of a solvent, and can provide good spreadability of a solution onto a sample substrate. In some embodiments, the surfactant is non-ionic, and can minimize the likelihood of precipitation from solution that can result, for example, from ionic interactions with components within a formulation, such as an ionically charged dye. A solution having little or no precipitates can be more easily discharged from a dispensing nozzle and can reduce the likelihood that the dispensing nozzle will clog or that a liquid flow is diminished. In some embodiments, the surfactant can decrease the likelihood of non-specific binding or minimize artifacts that can occur as a result of non-specific binding. Solutions having little or no precipitates can also minimize artifacts that can be present in a sample.

The first and second staining solutions can each independently include from approximately 0.05% (e.g., approximately 0.075%, approximately 0.1%, approximately 0.2%, approximately 0.3%, or approximately 0.4%) to approximately 0.5% (e.g., approximately 0.4%, approximately 0.3%, approximately 0.2%, approximately 0.1%, or approximately 0.075%) by volume of a liquid surfactant or by weight of a solid surfactant. In some embodiments, the first and second staining solutions can each independently include from approximately 0.5 to approximately two mL/L of a surfactant (e.g., a non-ionic surfactant). For example, the first and second staining solutions can each independently include approximately one ml/L of polysorbate 20 (e.g., Tween 20).

The surfactant may be non-ionic, cationic, anionic or zwitterionic. Mixtures of surfactants may also be used. Exemplary classes of surfactants include alcohol ether sulfates, alcohol sulfates, alkanolamides, alkyl sulfonates, amine oxides, amphoteric surfactants, anionic surfactants, betaine derivatives, cationic surfactants, disulfonates, dodecylbenzene, sulfonic acid, ethoxylated alcohols, ethoxylated alkyl phenols, ethoxylated fatty acids, glycerol esters hydrotropes, lauryl sulfates, mono and diglycerides, non-ionic surfactants, phosphate esters, quaternary surfactants, and sorbitan derivatives. Exemplary surfactants are as previously provided under the section entitled "Fixative Solution."

The first and second staining solutions can each independently include an agent to minimize non-specific binding of a dye to cellular components, such as ethylene glycol, propylene glycol, polyethylene glycol. In some embodiments, the first and second staining solutions can each independently include from approximately 0.5% (e.g., approximately 0.75%, approximately one %, approximately two %, approximately three %, or approximately four %) to approximately five % (e.g., approximately four %, approximately three %, approximately two %, approximately one %, or approximately 0.75%) by volume of a liquid non-specific binding minimizing agent, or by weight of a solid non-specific binding minimizing agent. For example, the first and second staining solutions can each independently include from approximately five mL/L (e.g., approximately 10 mL/L, approximately 15 mL/L, approximately 20 mL/L, approximately 25 mL/L, approximately 30 mL/L, approximately 35 mL/L, approximately 40 mL/L, or approximately 45 mL/L) to approximately 50 mL/L (e.g., approximately 45 mL/L, approximately 40 mL/L, approximately 35 mL/L, approximately 30 mL/L, approximately 25 mL/L, approximately 20 mL/L, approximately 15 mL/L, or approximately 10 mL/L) ethylene glycol. In some embodiments, the first and second staining solutions can each independently include approximately 10 mL/L (e.g., approximately 15 mL/L, approximately 20 mL/L, or approximately 25 mL/L) ethylene glycol.

The first and second staining solutions can each independently include a buffering agent. Examples of buffering agents include bis-tris buffer, phosphate, HEPES, MES, Tris, and organic buffers having a pH between about 5 and about 8. The first and second staining solutions can each independently include from approximately five mM (e.g., approximately 25 mM, approximately 50 mM, approximately 100 mM, approximately 150 mM, or approximately 200 mM) to approximately 250 mM (e.g., approximately 200 mM, approximately 150 mM, approximately 100 mM, approximately 50 mM, or approximately 25 mM) of a buffering agent. For example, the first and second staining solutions can each independently include approximately 50 mM bis-tris. In some embodiments, the buffering agent in the second stain solution is the same as the buffering agent in the first stain solution, to increase compatibility between the stain solutions.

The first and second staining solutions can each independently include a salt, such as sodium chloride, potassium chloride, sodium acetate, calcium chloride, magnesium chloride, sodium sulfate, magnesium sulfate, and ammonium sulfate. The first and second staining solutions can each independently include a salt concentration of from approximately one g/L (e.g., approximately two g/L, approximately five g/L, approximately 10 g/L, or approximately 15 g/L) to approximately 20 g/L (e.g., approximately 15 g/L, approximately 10 g/L, approximately five g/L, or approximately two g/L). For example, the first and second staining solutions can each independently include approximately four g/L (approximately three g/L or approximately two g/L) of a salt, such as sodium chloride. For example, the second staining solution can include approximately two g/L (e.g., approximately three g/L, or approximately four g/L) of a salt, such as sodium chloride. A salt can diminish non-specific binding of a cytological dye to a specimen. Without wishing to be bound by any theory, it is believed that the negative and positive ions of a salt can shield non-specific charge-charge interactions between a dye and a specimen by, for example, binding to charged species within a specimen.

The first and second staining solution can each independently include an antimicrobial agent. An antimicrobial agent can inhibit the growth of microorganisms and increase the shelf life of a staining solution. The antimicrobial agent can include benzalkonium chloride, 5-chloro-2-methyl-4-isothiazolin-3-one, 2-methyl-4-isothiazolin-3-one, ProClin® (e.g., ProClin 300®), azides, merthiolates, and/or antibiotics. In some embodiments, the antimicrobial agent includes 5-chloro-2-methyl-4-isothiazolin-3-one and 2-methyl-4-isothiazolin-3-one. For example, the antimicrobial agent can be ProClin® 300, which can contain about 2.3% 5-chloro-2-methyl-4-isothiazolin-3-one and about 0.7% 2-methyl-4-isothiazolin-3-one in inert solvents (e.g., modified glycol and alkyl carboxylate) available from Sigma-Aldrich. The first and second stain solutions can each independently include the antimicrobial agent at a concentration of from approximately 0.2 ppm (e.g., approximately one ppm, approximately five ppm, approximately 10 ppm, approximately 20 ppm, approximately 30 ppm, or approximately 40 ppm) to approximately 50 ppm (e.g. approximately 40 ppm, approximately 30 ppm, approximately 20 ppm, approximately 10 ppm, approximately five ppm, or approximately one ppm). In some embodiments, the first and second staining solutions can each independently contain approximately 15 ppm (approximately 10 ppm, approximately 5 ppm, or approximately 2 ppm) ProClin 300®.

In some embodiments, the first and second staining solutions can each independently further include an acid to adjust a pH. The acid can be any acid traditionally used to adjust the pH of a solution. For example, acetic acid, nitric acid, hydrochloric acid, phosphoric acid, formic acid, sulfuric acid, or citric acid can be used.

The first and second staining solutions can each independently have a pH of from approximately 5 to approximately 8 (e.g., from approximately 5.5 to approximately 8, from approximately 5.5 to approximately 7.5, from approximately 5.5 to approximately 7, from approximately 5.5 to approximately 6, from approximately 5.8 to approximately 6.2, from approximately 5.9 to approximately 6.1, a pH of approximately 6, or a pH of approximately 7). In some embodiments, the first staining solution can have an absorbance of from approximately 0.1 to approximately 1 (e.g., from approximately 0.1 to approximately 0.8, from approximately 0.1 to approximately 0.7, from approximately 0.1 to approximately 0.5, from approximately 0.1 to approximately 0.4, from approximately 0.1 to approximately 0.3, from approximately 0.15 to approximately 0.3, from approximately 0.15 to approximately 0.2, from approximately 0.185 to approximately 0.205, approximately 0.19, or approximately 0.2) at a maximum peak wavelength of from about 510 to about 530 nm (e.g., about 510 to about 520 nm, or about 515 to about 517 nm) at a dilution in water of 1:500 first staining solution to water. In some embodiments, the second staining solution can have an absorbance of from approximately 0.1 to approximately 1 (e.g., from approximately 0.1 to approximately 0.8, from approximately 0.1 to approximately 0.7, from approximately 0.1 to approximately 0.5, from approximately 0.1 to approximately 0.4, from approximately 0.1 to approximately 0.3, from approximately 0.15 to approximately 0.3, from approximately 0.15 to approximately 0.2, from approximately 0.185 to approximately 0.205, approximately 0.19, or approximately 0.2) at a peak wavelength of from about 630 to about 660 nm (e.g., about 640 to about 660 nm, about 640 to about 655 nm, about 645 to about 655 nm, about 650 to about 655 nm, or about 650.5 to about 652.5 nm) at a dilution of 1:1000 second staining solution to water.

In some embodiments, to make the first or second staining solution, distilled or deionized water is first added to a mixing vessel to less than 100% (e.g., approximately 90%) of the final desired volume. Calculated amounts of a non-specific binding minimizer agent (e.g., ethylene glycol), a surfactant (e.g., polysorbate 20), one or more cytological dyes (e.g., eosin Y, or azure B and methylene blue), a salt (e.g., NaCl), an antimicrobial agent (e.g., ProClin 300®), an acid (e.g., acetic acid), and/or a buffering agent (e.g., bis tris) can be added to the water. Further water can be added to bring the solution to its final desired volume. The mixture can be mixed with a magnetic stir plate/stir bar and/or an impeller for a minimum of about 30 minutes. After mixing, a pH reading is carried out on an aliquot of the first or second staining solution using a pH meter (e.g., a Mettler pH meter). In some embodiments, if the pH is not within a desired range (e.g., five to eight), then further acid can be added to the first or second staining solution until the desired pH is attained.

Figure 4:
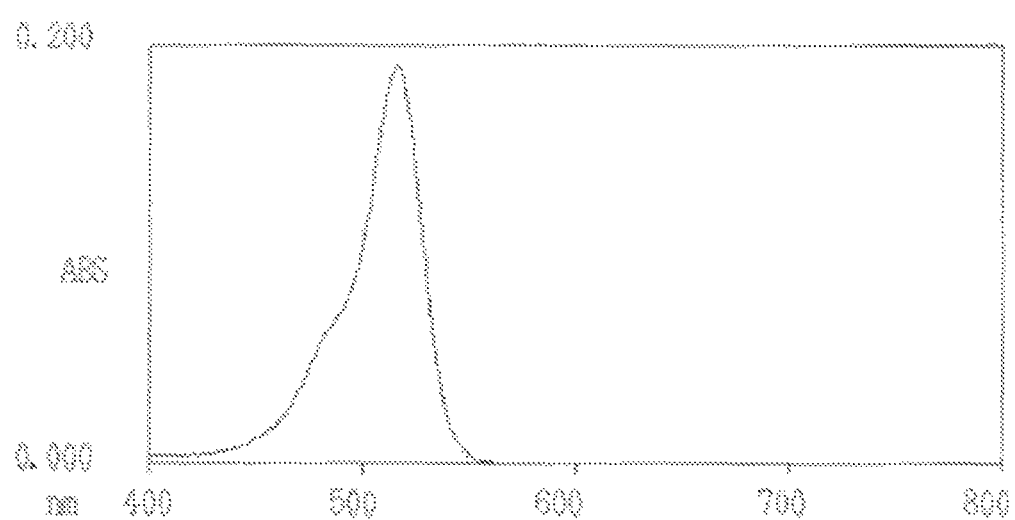
FIG. 4 is a UV-Vis absorption spectrum of an embodiment of a first staining solution.

First staining solution absorbance can be measured using a UV-spectrophotometer (e.g., a Hitachi UV-spectrophotometer). A baseline can first be run on the spectrophotometer. For example, a 10 mL sample of the first staining solution can be filtered through a 0.45 µm syringe filter, diluted 1:500 with distilled water, and then scanned on the spectrophotometer at between 500-700 nm. The absorbance at 510 to 530 nm can be recorded. A representative UV-Vis absorption spectrum of a first staining solution including eosin Y is shown, for example, in FIG. 4. If necessary, additional cytological dye can be added to the first staining solution to bring the absorbance to a desired range. If additional cytological dye (e.g., eosin) is added to the first staining solution, the solution can be mixed for a minimum of about 30 minutes, and the measurement process (e.g., filtering a 10 mL aliquot, diluting the aliquot in distilled water at a ratio of 1:500, and taking an absorbance measurement) can be repeated. The pH of the solution can be re-measured and adjusted to pH 5-8 (if necessary) by the method above.

Figure 6:
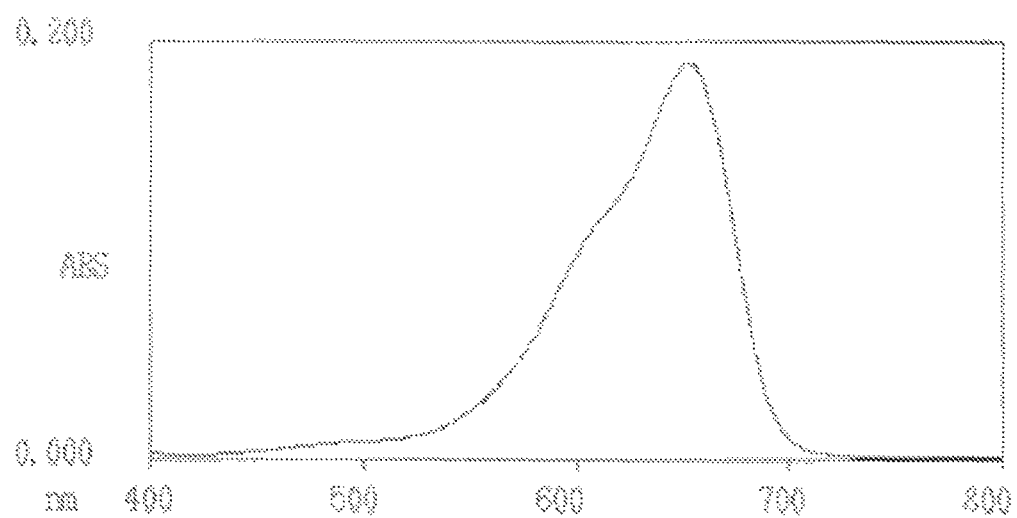
FIG. 6 is a UV-Vis absorption spectrum of an embodiment of a second staining solution.

Second staining solution absorbance can be measured using a UV-spectrophotometer (e.g., a Hitachi UV-spectrophotometer). A baseline can first be run on the spectrophotometer. A 10 mL sample of the second staining solution can be filtered through a 0.45 µm syringe filter, diluted 1:1000 with distilled water, and then scanned on the spectrophotometer at between 500-700 nm. The absorbance at 630-660 nm can be recorded. A representative UV-Vis absorption spectrum of a second staining solution including 1:1 methylene blue to azure B is shown, for example, in FIG. 6. If necessary, additional cytological dye can be added to the second staining solution to bring the absorbance to a desired range. A portion of the filtered sample can also be chromatographed using high-performance liquid chromatography (HPLC) and the area of the tallest absorbance peak corresponding to each dye within the sample can be recorded. The peak areas can be approximately equivalent between the different dye constituents.

If the HPLC peak areas for the dyes within the second staining solution are not approximately equivalent, additional cytological dye (e.g., azure B and/or methylene blue) can be added to the second staining solution until the solution can include approximately equal amounts (as assessed by the peak areas) of each of the dyes. After adding one or more dyes, the second staining solution can be mixed for a minimum of about 30 minutes, and the measurement process (e.g., filtering a 10 mL aliquot, diluting the aliquot in distilled water at a ratio of 1:500, and taking absorbance and HPLC measurements) can be repeated. The pH of the solution can be re-measured and adjusted to a desired range (if necessary) by the method described above.

Finally, the first and second staining solution can each be independently filtered through a 0.45 µm filter to remove any particulates before bottling. In some embodiments, a finer or coarser filter can be used. For example, a 0.1 to one µm filter (e.g., a 0.2 µm filter, a 0.4 µm filter, or a 0.8 µm filter) can be used to remove any microorganisms and/or particulates in the first or second staining solution. In some embodiments, the first or second staining solution can each be independently stored in a 250 mL bottle and filled to 250 g±1 g, as measured by a balance. The pH of the final product can be measured, if desired. In some embodiments, a first staining solution's HPLC chromatogram can be obtained, for example, to assess solution purity. In some embodiments, a second staining solution's HPLC chromatogram can be obtained, for example, to assess solution purity and/or to obtain a ratio of the dyes within the solution.

In some embodiments, a first stain solution can stain certain cells of a specimen prepared from, for example, a blood sample (e.g., eosinophils, neutrophils). The first stain solution can contain a bis-tris buffer, and the resulting stain solution can provide a redder color and a more visually pleasing stained specimen. The bis-tris buffer can be compatible with eosin Y. In some embodiments, azure B is included in more than one formulation, such as in a fixative solution and a second stain solution. When a specimen is exposed more than once to azure B, it is believed that better staining of the specimen can occur compared to a single exposure to azure B.

The first and second stain solutions can each independently contain NaCl and ethylene glycol, which together can provide a synergistic shielding effect to non-specific binding, i.e., where a formulation containing both NaCl and ethylene glycol can have less non-specific binding than a formulation containing an equivalent concentration of either NaCl or ethylene glycol. For example, a formulation including both NaCl and ethylene glycol can provide a lighter colored nucleoli than the remaining nucleus, while a formulation without NaCl and ethylene glycol can provide a uniformly dark nucleus. In some embodiments, a stain solution including NaCl can have decreased background staining compared to a stain solution without NaCl.

For example, the first cytological staining solution can include about 0.5 g/L to about 5.0 g/L Eosin Y; about 5 mM to about 250 mM bis-tris or phosphate buffer; about 0.5 mL/L to about 2.0 mL/L polysorbate 20; about one g/L to about 20 g/L sodium chloride; about five mL/L to about 50 mL/L ethylene glycol; about 0.2 ppm to about 50 ppm ProClin 300®; acetic acid; and water, wherein the solution has a pH of from about 5.8 to about 6.2.

As another example, the first cytological staining solution can include about 0.6 g/L to about 0.9 g/L Eosin Y; about 45 mM to about 55 mM bis-tris buffer; about 0.8 mL/L to about 1.2 mL/L polysorbate 20; about three g/L to about five g/L sodium chloride; about nine mL/L to about 11 mL/L ethylene glycol; about 10 ppm to about 20 ppm ProClin 300®; acetic acid; and water, wherein the solution has a pH of from about 5.8 to about 6.2.

For example, the first cytological staining solution can include about 0.75 g/L Eosin Y; about 50 mM bis-tris buffer; about one mL/L polysorbate 20; about four g/L sodium chloride; about 10 mL/L ethylene glycol; about 15 ppm ProClin 300®; acetic acid; and water, wherein the solution has a pH of from about 5.8 to about 6.2.

As another example, the first cytological staining solution can include about 0.75 g/L Eosin Y; about 50 mM bis-tris buffer; about 0.5 mL/L polysorbate 20; about six g/L sodium chloride; about 20 mL/L ethylene glycol; about 15 ppm ProClin 300®; acetic acid; and water, wherein the solution has a pH of from about 5.8 to about 6.2.

As a further example, the first cytological staining solution can include about 0.75 g/L Eosin Y; about 50 mM phosphate buffer; about 2.0 mL/L polysorbate 20; about four g/L sodium chloride; about 50 mL/L ethylene glycol; about 15 ppm ProClin 300®; acetic acid; and water, wherein the solution has a pH of from about 5.8 to about 6.2.

For example, the second cytological staining solution can include about 0.25 to about 2.5 g/L Azure B; about 0.25 g/L to about 0.5 g/L methylene blue; about 5 mM to about 250 mM bis-tris or HEPES buffer; about 0.5 mL/L to about 2.0 mL/L polysorbate 20, about one g/L to about 20 g/L sodium chloride, and about 0.2 ppm to about 50 ppm ProClin 300®; acetic acid; and water, wherein the solution has a pH of from about 6.8 to about 7.2.

As another example, the second cytological staining solution can include about 0.4 to about 0.6 g/L Azure B; about 0.4 g/L to about 0.5 g/L methylene blue; about 45 mM to about 55 mM bis-tris buffer; about 0.8 mL/L to about 1.2 mL/L polysorbate 20, about 1.8 g/L to about 2.2 g/L sodium chloride, and about 10 ppm to about 20 ppm ProClin 300®; acetic acid; and water, wherein the solution has a pH of from about 6.8 to about 7.2.

For example, the second cytological staining solution can include about 0.5 g/L Azure B; about 0.45 g/L methylene blue; about 50 mM bis-tris buffer; about one mL/L polysorbate 20, about two g/L sodium chloride, and about 15 ppm ProClin 300®; acetic acid; and water, wherein the solution has a pH of from about 6.8 to about 7.2.

As another example, the second cytological staining solution can include about 0.5 g/L Azure B; about 0.45 g/L methylene blue; about 50 mM HEPES buffer; about 0.5 mL/L polysorbate 20, about two g/L sodium chloride, and about 15 ppm ProClin 300®; acetic acid; and water, wherein the solution has a pH of from about 6.8 to about 7.2.

As a further example, the second cytological staining solution can include about 0.5 g/L Azure B; about 0.45 g/L methylene blue; about 50 mM HEPES buffer; about one mL/L polysorbate 20, about one g/L sodium chloride, and about 15 ppm ProClin 300®; acetic acid; and water, wherein the solution has a pH of from about 6.8 to about 7.2.

Rinse Solution

Generally, the rinse solution can be an aqueous solution. The solvent can include distilled water or deionized water. The rinse solution can include a non-specific binding minimizer agent, such as polyethylene glycol, polyvinyl pyrrolidone, polyacrylic acid, polyvinyl alcohol, polysaccharides, and/or other hydrophilic water-soluble polymers. In some embodiments, the non-specific binding minimizer agent can include ethylene glycol or propylene glycol. Without wishing to be bound by any theory, it is believed that the non-specific binding minimizer agent can prepare a specimen for drying processes during sample preparation. The non-specific binding minimizer agent can provide a lacquer over the specimen and can provide an enhanced visual appearance to the specimen. The non-specific binding minimizer agent can have a concentration of from approximately one g/L (e.g., approximately two g/L, approximately three g/L, approximately four g/L, approximately five g/L, approximately six g/L, approximately seven g/L, approximately eight g/L, or approximately nine g/L) to approximately ten g/L (e.g., approximately nine g/L, approximately eight g/L, approximately seven g/L, approximately six g/L, approximately five g/L, approximately four g/L, approximately three g/L, or approximately two g/L) in the rinse solution. For example, the rinse solution can include approximately five g/L polyethylene glycol (e.g., polyethylene glycol 1450).

The rinse solution can include a surfactant. Without wishing to be bound by any theory, it is believed that a surfactant reduces the surface tension of a solvent, and can provide good spreadability of a solution onto a sample substrate. In some embodiments, the surfactant is non-ionic, and can minimize the likelihood of precipitation of solution components that can result, for example, from ionic interactions with components within a formulation, such as an ionically charged dye. A solution having little or no precipitates can be more easily discharged from a dispensing nozzle and can reduce the likelihood that the dispensing nozzle will clog or that a liquid flow is diminished. In some embodiments, the surfactant can decrease the likelihood of non-specific binding or minimize artifacts that can occur as a result of non-specific binding. A solution having little or no precipitates can minimize artifacts that can be present in a specimen.

The rinse solution can include from approximately 0.05% (e.g., approximately 0.075%, approximately 0.1%, approximately 0.2%, approximately 0.3%, or approximately 0.4%) to approximately 0.5% (e.g., approximately 0.4%, approximately 0.3%, approximately 0.2%, approximately 0.1%, or approximately 0.075%) by volume of a liquid surfactant or by weight of a solid surfactant. In some embodiments, the rinse solution can include from approximately 0.5 to approximately two mL/L of a surfactant (e.g., a non-ionic surfactant). For example, the rinse solution can include approximately one ml/L of polysorbate 20 (e.g., Tween 20).

The surfactant may be non-ionic, cationic, anionic or zwitterionic. Mixtures of surfactants may also be used. Exemplary classes of surfactants include alcohol ether sulfates, alcohol sulfates, alkanolamides, alkyl sulfonates, amine oxides, amphoteric surfactants, anionic surfactants, betaine derivatives, cationic surfactants, disulfonates, dodecylbenzene, sulfonic acid, ethoxylated alcohols, ethoxylated alkyl phenols, ethoxylated fatty acids, glycerol esters hydrotropes, lauryl sulfates, mono and diglycerides, non-ionic surfactants, phosphate esters, quaternary surfactants, and sorbitan derivatives. Exemplary surfactants are as previously provided under the section entitled "Fixative Solution".

The rinse solution can include a buffering agent. Examples of buffering agents include HEPES buffer (e.g., HEPES sodium salt and/or HEPES free acid), bis-tris buffer, phosphate, MES, Tris, and organic buffers having a pH between 5 and 8. The rinse solution can include from approximately five mM (e.g., approximately 25 mM, approximately 50 mM, approximately 100 mM, approximately 150 mM, or approximately 200 mM) to approximately 250 mM (e.g., approximately 200 mM, approximately 150 mM, approximately 100 mM, approximately 50 mM, or approximately 25 mM) of a buffering agent. For example, the rinse solution can include approximately 50 mM HEPES.

The rinse solution can include an antimicrobial agent. An antimicrobial agent can inhibit the growth of microorganisms and increase the shelf life of a rinse solution. The antimicrobial agent can include benzalkonium chloride, 5-chloro-2-methyl-4-isothiazolin-3-one, 2-methyl-4-isothiazolin-3-one, ProClin® (ProClin 300®), azides, merthiolates, and/or antibiotics. In some embodiments, the antimicrobial agent includes 5-chloro-2-methyl-4-isothiazolin-3-one and 2-methyl-4-isothiazolin-3-one. For example, the antimicrobial agent can be ProClin 300®, which can contain about 2.3% 5-chloro-2-methyl-4-isothiazolin-3-one and about 0.7% 2-methyl-4-isothiazolin-3-one in inert solvents (e.g., modified glycol and alkyl carboxylate) available from Sigma-Aldrich. The antimicrobial agent can be present at a concentration of from approximately 0.2 ppm (e.g., approximately one ppm, approximately five ppm, approximately 10 ppm, approximately 20 ppm, approximately 30 ppm, or approximately 40 ppm) to approximately 50 ppm (e.g. approximately 40 ppm, approximately 30 ppm, approximately 20 ppm, approximately 10 ppm, approximately five ppm, or approximately one ppm). In some embodiments, the rinse solution contains approximately 15 ppm (approximately 10 ppm, approximately 5 ppm, or approximately 2 ppm) ProClin 300®.

In some embodiments, the rinse solution further includes an acid to adjust a pH. The acid can be any acid traditionally used to adjust the pH of a solution. For example, acetic acid, nitric acid, hydrochloric acid, phosphoric acid, formic acid, sulfuric acid, or citric acid can be used.

The rinse solution can include an alcohol, such as methanol, ethanol, or propanol. The alcohol can remove excess dyes, can promote faster drying of the rinse solution on the specimen and/or the substrate. In some embodiments, DMSO or other organic solvent in which the dyes are soluble can be used in the rinse solution and can provide complete fluid evacuation from a delivering nozzle. For example, the rinse solution can include from approximately 10 mL/L (e.g., approximately 25 mL/L, approximately 50 mL/L, approximately 75 mL/L, approximately 100 mL/L, approximately 125 mL/L, approximately 150 mL/L, or approximately 175 mL/L) to approximately 200 mL/L (e.g., approximately 175 mL/L, approximately 150 mL/L, approximately 125 mL/L, approximately 100 mL/L, approximately 75 mL/L, approximately 50 mL/L, or approximately 25 mL/L) of an alcohol. In some embodiments, the rinse solution includes approximately 50 mL/L methanol. In some embodiments, the rinse solution can have at most approximately 200 mL/L of an organic solvent, so that a rinse solution cannot wash an excessive amount of desired dye from a stained biological sample.

The rinse solution can have a pH of from approximately 5 to approximately 8 (e.g., from approximately 5.5 to approximately 8, from approximately 5.5 to approximately 7.5, from approximately 5.5 to approximately 7, from approximately 5.5 to approximately 6, from approximately 5.8 to approximately 6.2, from approximately 5.9 to approximately 6.1, a pH of approximately 7.0, or a pH of approximately 6.0). For example, the rinse solution can have a pH of approximately 7.0.

To make the rinse solution, distilled or deionized water can be added to a mixing vessel to less than 100% (e.g., approximately 90%) of the final desired volume.

Calculated amounts of an alcohol (e.g., methanol), a non-specific binding minimizer agent (e.g., PEG), a buffering agent (e.g., HEPES sodium salt and HEPES free acid), a surfactant (e.g., polysorbate 20), an acid (if used), and an antimicrobial agent (e.g., ProClin 300®) can be added to the water. Further water can be added to bring the solution to its final desired volume. The mixture can be mixed with a magnetic stir plate/stir bar and/or an impeller for a minimum of about 30 minutes. After mixing, a pH reading can be carried out on an aliquot of the rinse solution using a pH meter (e.g., a Mettler pH meter). In some embodiments, if the pH is not within a desired range (e.g., about five to about eight), then further acid can be added to the second staining solution until a desired pH is attained.

Finally, the rinse solution can be filtered through a 0.45 μm filter to remove any particulates before bottling. In some embodiments, a finer or coarser filter can be used. For example, a 0.1 to one μm filter (e.g., a 0.2 μm filter, a 0.4 μm filter, or a 0.8 μm filter) can be used to remove any microorganisms and/or particulates in the rinse solution. In some embodiments, the rinse solution can be stored in a 500 mL bottle and filled to 500 g±1 g, as measured by a balance. The pH of the final product can be measured, if desired.

In some embodiments, a rinse solution that includes polyethylene glycol that is applied at the end of stain application can improve the visual appearance of a specimen, compared to a specimen treated with a rinse solution without polyethylene glycol. In some embodiments, a rinse solution including HEPES buffer at a pH of approximately 6.8 can improve the appearance of cells, such as red blood cells, by providing a better color balance between red and blue colors.

In some embodiments, the components of the rinse solution can be present at concentrations lower than those described above (e.g., by a factor of five).

The polyethylene glycol component of the rinse solution can have a concentration of from approximately 0.2 g/L (e.g., approximately 0.4 g/L, approximately 0.6 g/L, approximately 0.8 g/L, approximately one g/L, approximately 1.2 g/L, approximately 1.4 g/L, approximately 1.6 g/L, or approximately 1.8 g/L) to approximately two g/L. For example, the rinse solution can include approximately one g/L polyethylene glycol (e.g., polyethylene glycol 1450).

The rinse solution can include from approximately 0.01% (e.g., approximately 0.015%, approximately 0.02%, approximately 0.04%, approximately 0.06%, or approximately 0.8%) to approximately 0.1% by volume of a liquid surfactant or by weight of a solid surfactant. In some embodiments, the rinse solution can include from approximately 0.0501% to 0.306% of a surfactant. In some embodiments, the rinse solution can include from approximately 0.1 to approximately 0.4 mL/L of a surfactant (e.g., a non-ionic surfactant). For example, the rinse solution can include approximately 0.2 ml/L of polysorbate 20 (e.g., Tween 20).

The rinse solution can include from approximately one mM (e.g., approximately 5 mM, approximately 10 mM, approximately 20 mM, approximately 30 mM, or approximately 40 mM) to approximately 50 mM of a buffering agent. For example, the rinse solution can include approximately 10 mM HEPES.

The antimicrobial agent can be present at a concentration of from approximately 0.04 ppm (e.g., approximately 0.2 ppm, approximately one ppm, approximately two ppm, approximately five ppm, approximately six ppm, or approximately eight ppm) to approximately 10 ppm. In some embodiments, the rinse solution contains approximately three ppm (approximately two ppm, approximately one ppm, or approximately 0.4 ppm) ProClin 300®.

The rinse solution can include from approximately two mL/L (e.g., approximately five mL/L, approximately ten mL/L, approximately 15 mL/L, approximately 20 mL/L, approximately 25 mL/L, approximately 30 mL/L, or approximately 35 mL/L) to approximately 40 mL/L of an alcohol. In some embodiments, the rinse solution includes approximately ten mL/L methanol. In some embodiments, the rinse solution can have at most approximately 40 mL/L of an organic solvent, so that a rinse solution cannot wash an excessive amount of desired dye from a stained biological sample.

For example, the rinse solution can include about 0.2 g/L to about ten g/L polyethylene glycol; about 1 mM to about 250 mM HEPES, MES, or bis-tris buffer; about 0.1 mL/L to about 2.40 mL/L polysorbate 20; about 0.04 ppm to about 50 ppm ProClin 300®; about 9 mL/L to about 200 mL/L methanol; and water, wherein the rinse solution has a pH of from about 6.6 to about 7.0.

For example, the rinse solution can include about one g/L to about ten g/L polyethylene glycol; about 5 mM to about 250 mM HEPES, MES, or bis-tris buffer; about 0.5 mL/L to about 2.0 mL/L polysorbate 20; about 0.2 ppm to about 50 ppm ProClin 300®; about 10 mL/L to about 200 mL/L methanol; and water, wherein the rinse solution has a pH of from about 6.6 to about 7.0.

As another example, the rinse solution can include about 4.5 g/L to about 5.5 g/L polyethylene glycol; about 45 mM to about 55 mM HEPES buffer; about 0.8 mL/L to about 1.2 mL/L polysorbate 20; about 10 ppm to about 20 ppm ProClin 300®; about 45 mL/L to about 55 mL/L methanol; and water, wherein the rinse solution has a pH of from about 6.6 to about 7.0.

For example, the rinse solution includes about five g/L polyethylene glycol; about 50 mM HEPES buffer; about one mL/L polysorbate 20; about 15 ppm ProClin 300®; about 50 mL/L methanol; and water, wherein the rinse solution has a pH of from about 6.6 to about 7.0.

As another example, the rinse solution includes about 10 g/L polyethylene glycol; about 50 mM MES buffer; about one mL/L polysorbate 20; about 15 ppm ProClin 300®; about 50 mL/L methanol; and water, wherein the rinse solution has a pH of from about 6.6 to about 7.0.

As a further example, the rinse solution includes about 10 g/L polyethylene glycol; about 50 mM bis-tris buffer; about 0.5 mL/L polysorbate 20; about 15 ppm ProClin 300®; about 50 mL/L methanol; and water, wherein the rinse solution has a pH of from about 6.6 to about 7.0.

For example, the rinse solution can include about 0.2 g/L to about two g/L polyethylene glycol; about one mM to about 50 mM HEPES buffer; about 0.16 mL/L to about 0.24 mL/L polysorbate 20; about 0.04 ppm to about 10 ppm ProClin 300®; about 9 mL/L to about 11 mL/L methanol; and water, wherein the rinse solution has a pH of from about 6.6 to about 7.0.

As another example, the rinse solution can include about 0.9 g/L to about 1.1 g/L polyethylene glycol; about 9 mM to about 11 mM HEPES buffer; about 0.16 mL/L to about 0.24 mL/L polysorbate 20; about 2 ppm to about 10 ppm ProClin 300®; about 9 mL/L to about 11 mL/L methanol; and water, wherein the rinse solution has a pH of from about 6.6 to about 7.0.

In still another example, the rinse solution includes about one g/L polyethylene glycol; about 10 mM HEPES buffer; about 0.2 mL/L polysorbate 20; about 3 ppm ProClin 300®; about 10 mL/L methanol; and water, wherein the rinse solution has a pH of from about 6.6 to about 7.0.

Kits

Figure 25:
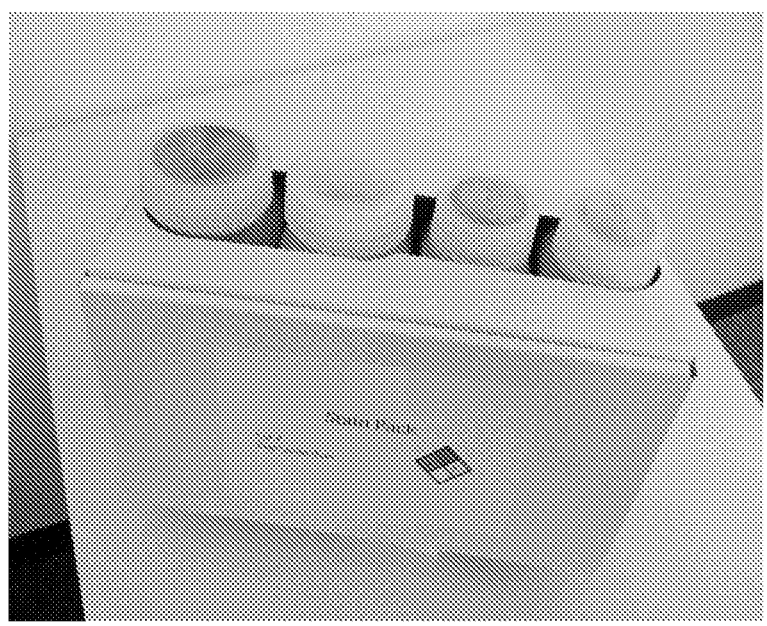
FIG. 25 is an embodiment of a kit containing a fixative solution, a first staining solution, a second staining solution, and a rinse solution.

In some embodiments, a kit can include one or more bottles of each of the fixative solution, first stain solution, second stain solution, and/or a rinse solution. The kit can include instructions and labels. The labels can include, for example, lot information and expiration date(s). FIG. 25 shows an example of a kit including a fixative solution, first and second staining solutions, and a rinse solution.

In some embodiments, the processing steps include applying a fixative solution, applying a fixative solution, applying a first stain solution, applying a second stain solution, applying a rinse solution, and applying a rinse solution.

Specimen Preparation Systems and Methods

Figure 7:
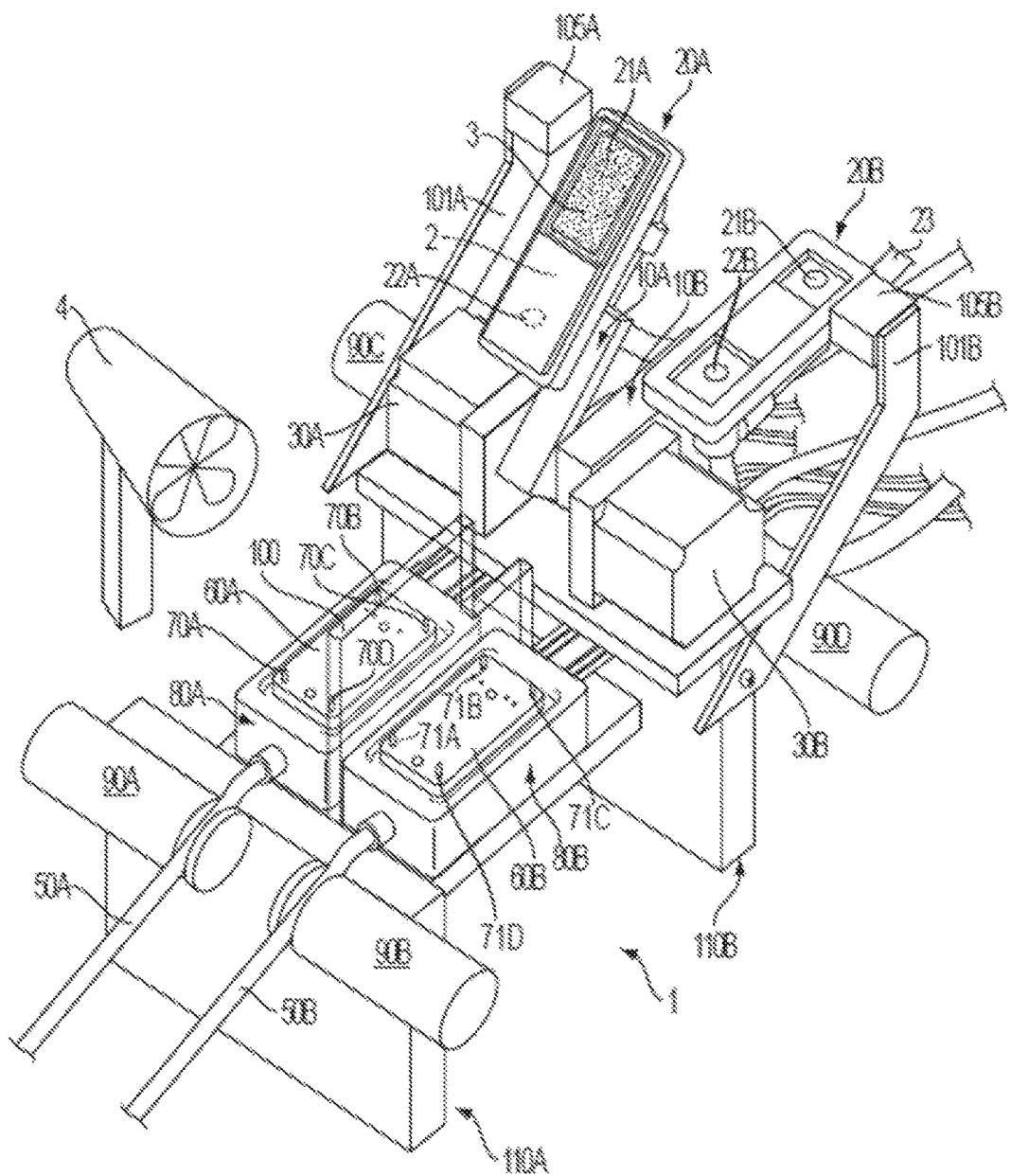
FIG. 7 is a perspective view of an embodiment of an apparatus for preparing specimens for examination, with both sample grippers 20A and 20B in an open position.

The fixative, staining, and rinse formulations above can be used in an apparatus or machine for preparing a specimen (as described, for example, in U.S. application Ser. No. 13/293,050, filed Nov. 9, 2011, herein incorporated by reference in its entirety), to enhance the visual appearance of certain features in the specimens. FIG. 7 illustrates an embodiment of an apparatus or machine 1 for preparing a specimen on a substrate 2 such as a microscope slide, cover slip, or other transparent surface, for examination or imaging. Machine 1 can be incorporated into an overall system for preparing and analyzing specimens comprising body fluids or other biological samples containing cells, such as system 2000 shown in FIG. 21 and described below. Machine 1 can generally include, or form a portion of, a system that features a first station that obtains a specimen, a second station that applies the specimen to a substrate, third and fourth stations for fixing and staining the specimen, respectively, a fifth station that dries the specimen, a sixth station that images the specimen, and a seventh station for analyzing the images and data obtained from the specimen. Certain embodiments of machine 1 are compatible with system 2000; some embodiments of machine 1 can be used in other specimen preparation systems, and/or as stand-alone devices.

Figure 8:
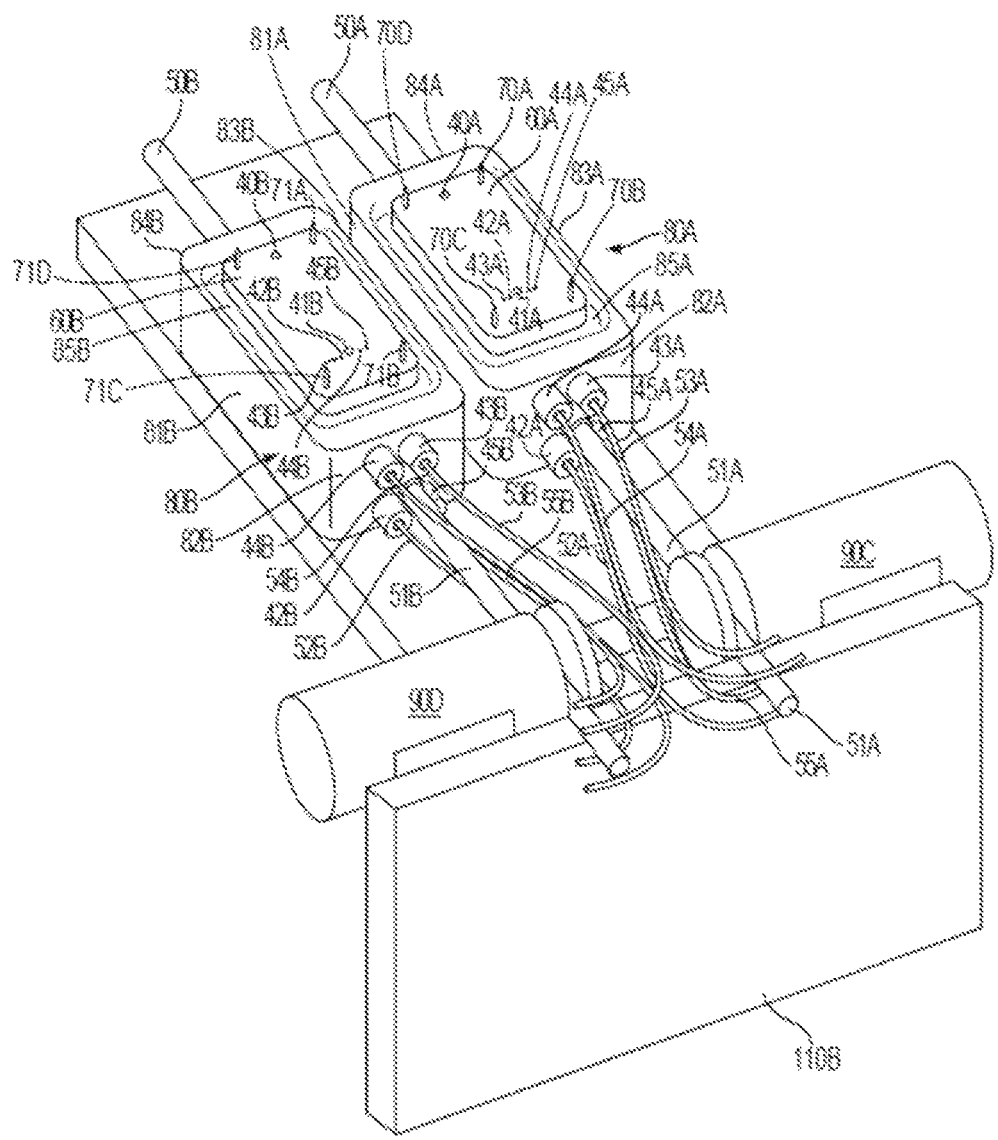
FIG. 8 is another perspective view of a portion of the apparatus of FIG. 7 (with the substrate arms and sample grippers not shown).

In general, machine 1 may include one or more (e.g., two, three, four, five, or more than five) platforms 60A and 60B as shown in FIGS. 7-9 for specimen processing. As shown in FIG. 8, platform 60A can include lateral sides for supporting a top side of the platform. A shield 100, shown in FIGS. 7 and 9, can be positioned between the platforms 60A and 60B to prevent fluids from splattering between the platforms 60. In some embodiments, shield 100 can be formed from a transparent material that blocks fluids from one of platforms 60A and 60B from contaminating the other platform. In certain embodiments, shield 100 can be formed from a material that is translucent or opaque. In FIGS. 7 and 9, shield 100 is depicted as being formed from a transparent material to allow other components positioned behind shield 100 to be shown in the same figure. Shield 100 could also have been shown as being formed from an opaque material, in which case portions of some components such as platform 60A and block 80A would have been obscured.

Figure 9A:
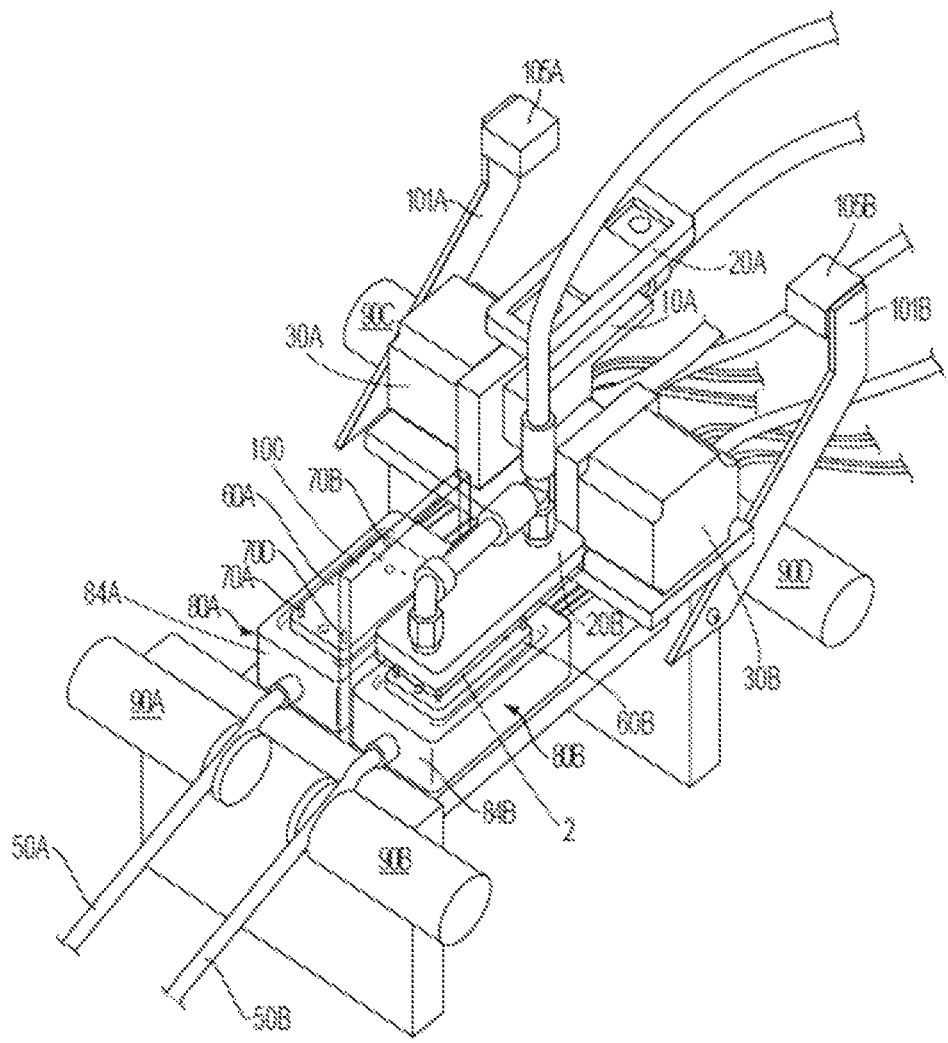
FIG. 9A is a further perspective view of the apparatus of FIG. 7, with sample gripper 20A in an open position and sample gripper 20B in a closed (specimen processing) position.
Figure 9B:
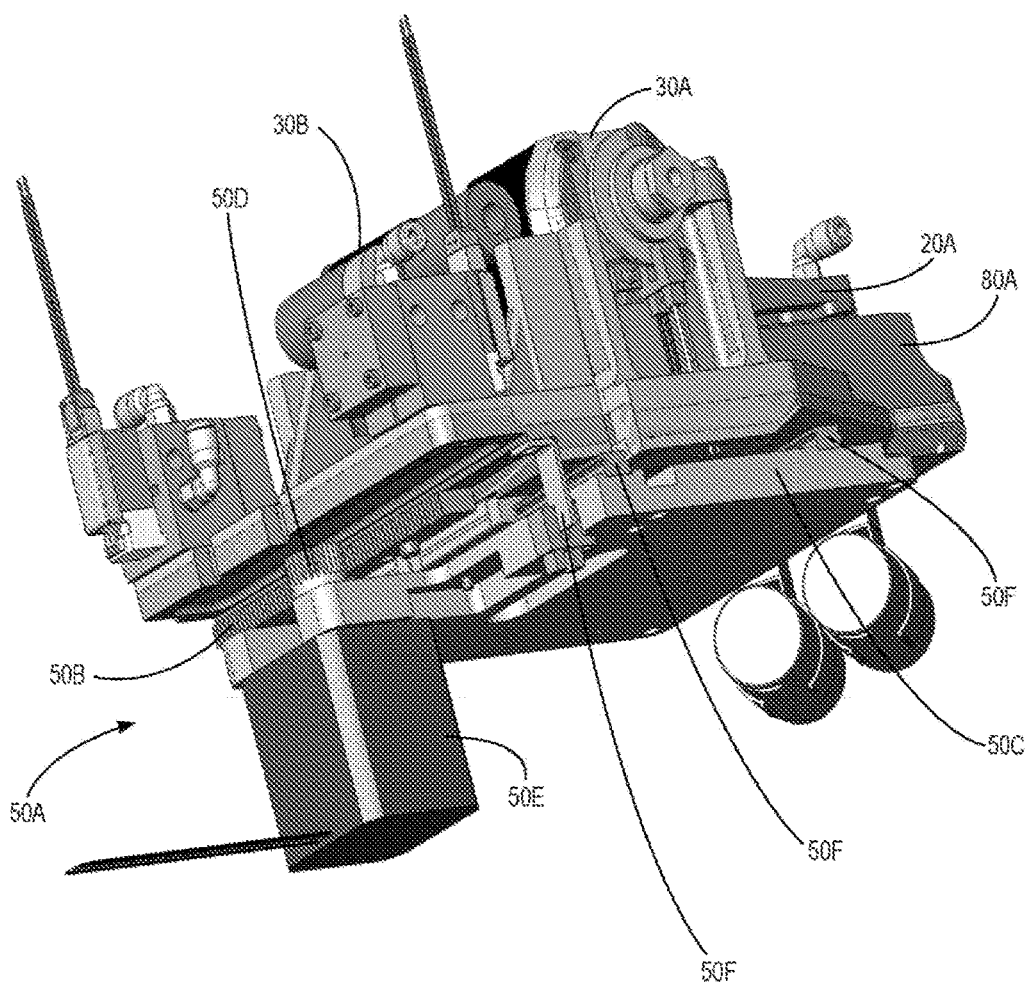
FIG. 9B is a perspective view of an indexing mechanism of the apparatus of FIG. 7.

FIG. 9B shows an indexing mechanism 50A that can be used to translate the machine 1 to provide substrates 2 from each of the substrate grippers 20A, 20B to a position for specimen processing. The indexing mechanism 50A can be in many forms, such as electromechanical devices (e.g., a rack and pinion gear set powered by an electric motor), linear actuators (e.g., pneumatic actuators, hydraulic actuators, or electromagnetic actuators). Although, in the illustrated embodiment, the indexing mechanism 50A translates the machine 1 linearly between two positions, other translation paths are possible based on the number of platforms included on the machine 1, and their configuration and layout, such as circular or semi-circular (e.g., an indexing table that can move in an arcuate path). As shown, the indexing mechanism 50A can include a gear rack 50B attached to a base 50C of the machine 1 and a pinion gear 50D attached to an electric motor 50E that is fixed to the base 50C. The machine 1 can be attached to the base 50C using one or more sliding devices 50F so that the machine 1 can move smoothly when translated by the indexing mechanism 50A. During use, the indexing mechanism 50A can move the machine 1 so that the multiple substrate grippers 20A and/or 20B of the machine 1 to receive a substrate 2 from a substrate mover 120 (shown in FIG. 11) so that a sample disposed on the substrate 2 can be prepared by the machine 1, and also so that, once prepared, the substrate gripper 20A and/or 20B can provide the substrate 2 having a prepared sample can be provided to the substrate mover 120 for sample processing.

For machines having two platforms 60A and 60B, as in the illustrated embodiment, substrates 2 are typically provided to, and from, the substrate mover 120 in an alternating manner. In some embodiments, a first substrate 2 is provided from the substrate mover 120 to a first substrate gripper 20A, to be processed at a first platform 60A, while the machine 1 is in a first position. While the first substrate 2 is processed at the first platform 60A, the indexing mechanism 50A can translate the machine 1 to a second position so that a second substrate gripper 20B can receive a second substrate, to be processed at the second platform 60B, from the substrate mover 120. While the second substrate is processed at the second platform 60B, the indexing mechanism 50A can translate the machine 1 back to the first position so that the substrate mover 120 can remove the first substrate 2 from the first substrate gripper 20A. Once the substrate 2 is removed from the first gripping platform 20A, a next substrate can be provided to the first gripping platform 20A. This method for providing substrates to alternating gripping platforms can be implemented for more than two (e.g., three, four, five, or more than five) platforms thereby increasing throughput of specimens prepared for further evaluation.

Platforms 60A and 60B are typically formed from one or more materials that are relatively chemically inert with respect to the fluids used during specimen processing and provide a suitable surface tension. Exemplary materials that can be used to form platforms 60A and 60B include engineering thermoplastics, such as polyoxymethylene (e.g., Delrin® manufactured by DuPont), high molecular weight fluorocarbons, such as polytetrafluoroethylene (PTFE) (e.g., Teflon® manufactured by DuPont), and metals such as aluminum, steel, and titanium, provided they are provided, manufactured, and/or treated to provide a suitable surface tension that acts to assist in evenly distributing and confining the processing fluids to the space between substrate 2 and the platforms, and allowing suitable evacuation of the processing fluids as well. By selection of suitable materials, the platforms can also advantageously reduce or minimize the formation of bubbles or spaces within the fluids as they are distributed, and at the same time maintain a sufficient surface tension such that fluid leakage out of the separation between the platforms and substrate 2 is reduced or eliminated.

In general, the surface area of platforms 60A and 60B can be selected as desired for purposes of substrate handling and fluid delivery. Factors such as the surface area of platforms 60A and 60B can also influence the selected surface area of substrate 2. For example, in some embodiments, the surface area of platform 60A (e.g., the area of the surface of platform 60A that faces substrate 2) is slightly smaller than the area of the surface of substrate 2 that faces platform 60A. By maintaining such a relationship between the areas of the facing surfaces of platform 60A and substrate 2, fluid leakage from the region between the surfaces can be reduced or eliminated. Typically, for example, the area of the surface of substrate 60A that faces substrate 2 is smaller than the area of the surface of substrate 2 by 2% or more (e.g., 3% or more, 5% or more, 7% or more, 10% or more, 15% or more, 20% or more, 25% or more, 30% or more).

Platforms 60A and 60B can be attached to blocks 80A and 80B, respectively. Block 80A includes lateral sides 81A-84A supporting a top side 85A as shown in FIG. 8. Blocks 80A and 80B can be made of the same or similar materials to those used for the platforms, including metals, ceramics, and/or plastics. Thus, materials such as Delrin® can be used to form blocks 80A and 80B, particularly in embodiments that implement Romanowsky staining of specimens. Other materials that can be used in embodiments include metals, and Teflon® brand polytetrafluoroethylene-coated aluminum, steel, or titanium.

In some embodiments, platforms 60A and/or 60B can be raised as shown in FIGS. 7-9. Alternatively, in certain embodiments, platforms 60A and/or 60B can be flush with the upper surface of blocks 80A and 80B, respectively. In either case, certain features of machine 1 as well as surface tension of fluids and surface energy of the platform or block prevent excess fluids from flowing past the edges of platforms 60A/60B and/or blocks 80A/80B.

As shown in FIGS. 7 and 8, platform 60A can include offsets 70A-70D to provide a separation between the surface of platform 60A and substrate 2, and prevent substrate 2 from contacting platform 60A. Platform 60B can include a corresponding set of offsets 71A-71D. Offsets can include standoffs, pins, pegs, rods, beads, walls, or other structures that provide separation between the surface of platform 60A and/or 60B and substrate 2. Offsets 70A-70D and 71A-71D ensure that the surfaces of platforms 60A and 60B and substrate 2 remain substantially parallel when substrate 2 contacts the offsets. The benefit of maintaining these two surfaces in parallel is that the volume enclosed between these two surfaces is thus defined and can be precisely controlled. If the two surfaces are not substantially parallel, and the angle between them changes, then the volume between them also changes and is not fixed and precisely controlled. In addition, the fluids may not apply uniformly to the specimen if such two surfaces are not substantially parallel.

As used herein, the phrase "substantially parallel" means that two surfaces are exactly parallel or nearly parallel, so that imperfections in the surface flatness of substrate 2 are reduced or eliminated when substrate 2 contacts the offsets. For example, although great care is taken in the production of substrates, certain substrates may have imperfections such as twist and/or non-coplanar corners. In the systems and methods disclosed herein, the use of offsets assists in correcting these imperfections by improving the surface flatness of substrate 2 where needed, orienting substrate 2 in a substantially parallel relationship to platforms 60A and 60B in the process. The phrase "substantially parallel" covers situations in which the two surfaces are not perfectly flat, but the offsets are all the same size or height, so that at least the contact points of a surface of the substrate with the offsets are in the same plane.

Figure 12A:
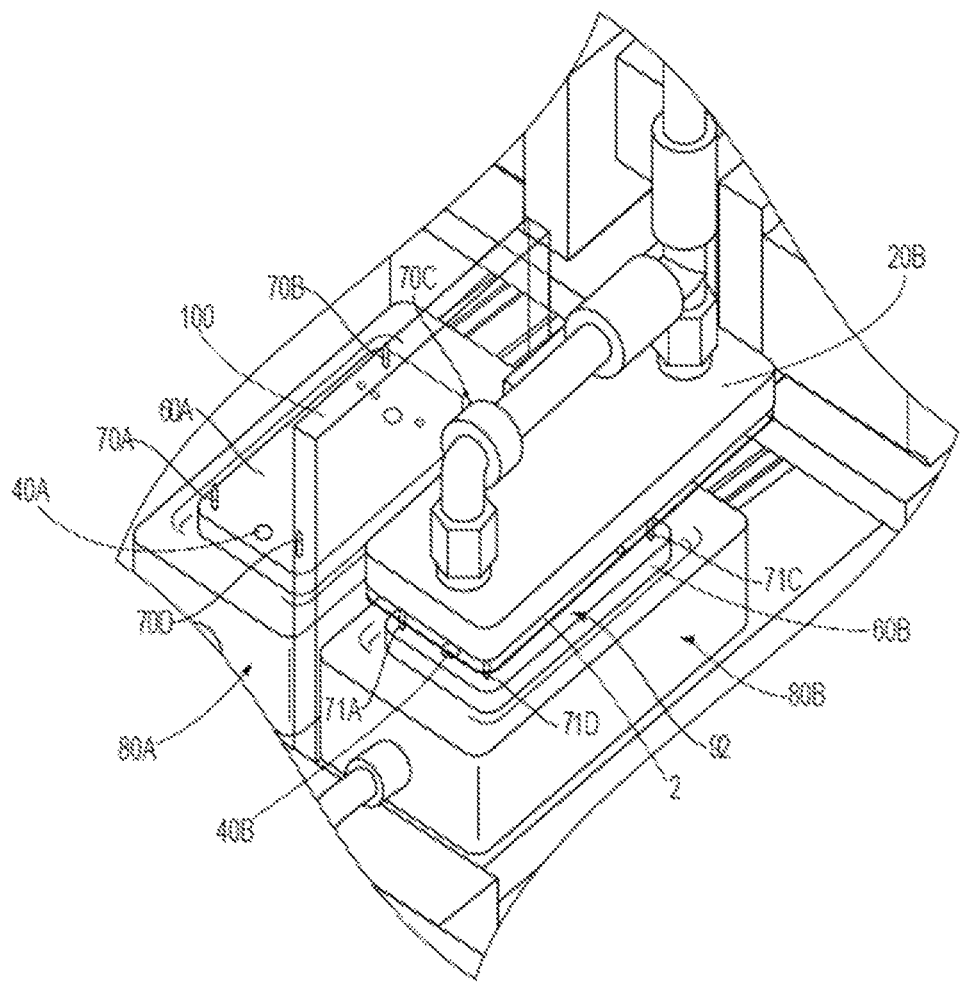
FIG. 12A is an expanded perspective view of a portion of the apparatus of FIG. 7 showing specimen gripper 20B, platform 60B, and block 80B in detail.

FIG. 12A shows substrate 2, substrate gripper 20B, blocks 80A, 80B, platforms 60A, 60B, offsets 70A-70D and 71A-71D, and separation 92 between substrate 2 and platform 60B. Separation 92 allows fluids to travel between the surface of platform 60B containing ports 40B-45B and substrate 2. The separation distance required for optimal specimen fixing, staining, and rinsing will vary depending on the flow rate of fluids dispensed from ports 40B-45B (and/or ports 40A-45A), port diameter, the viscosity of the fluids applied during processing, and the amount of suction available for removing fluids from the substrate, separation, and platform.

In some embodiments, for example, offsets providing a separation 92 of about 100-200 microns between the surface of platform 60B and substrate 2 enable fixing, staining, and rinsing for specimens comprising blood cells in embodiments capable of dispensing fluids at flow rates ranging from about 50 to about 300 microliters per second from ports 40B-45B having a diameter ranging from 500 to 1,500 microns. In general, the size or height of separation 92 can vary from about 50 microns to 1,000 microns for certain embodiments (e.g., from about 50 to 500 microns, from about 75 to 250 microns, from about 100 to 200 microns), provided such embodiments are capable of overcoming surface tension from fluids in the separation while dispensing and removing fluid during specimen processing. In addition, in certain embodiments, the diameters of ports located on platform 60A and/or 60B can vary from about 125 microns to 5,000 microns.

Figure 12B:
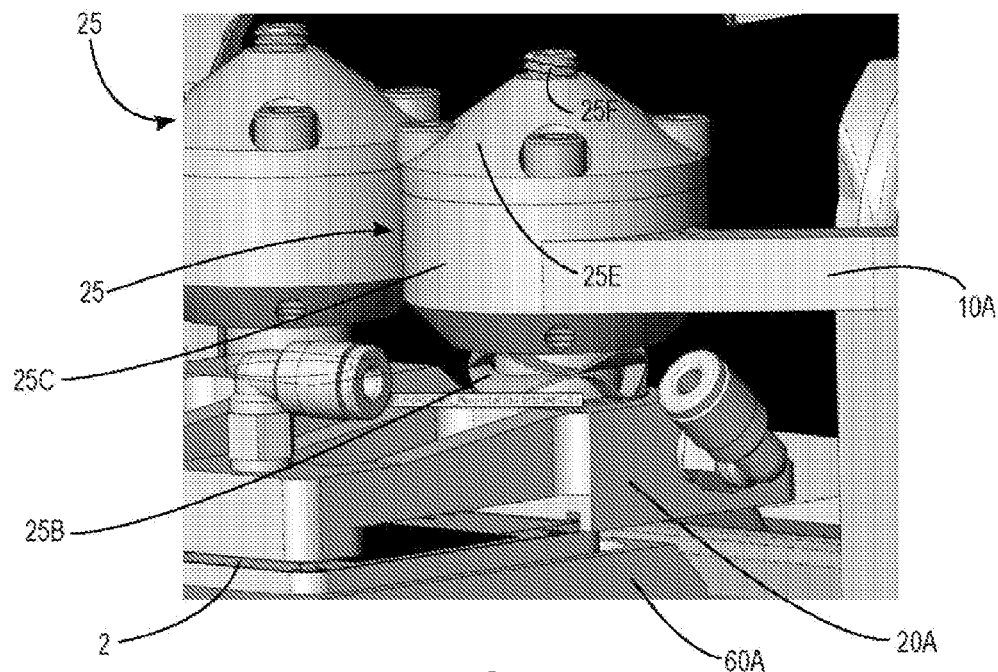
FIG. 12B is a perspective view of a ball joint mechanism of the apparatus of FIG. 7.
Figure 12C:
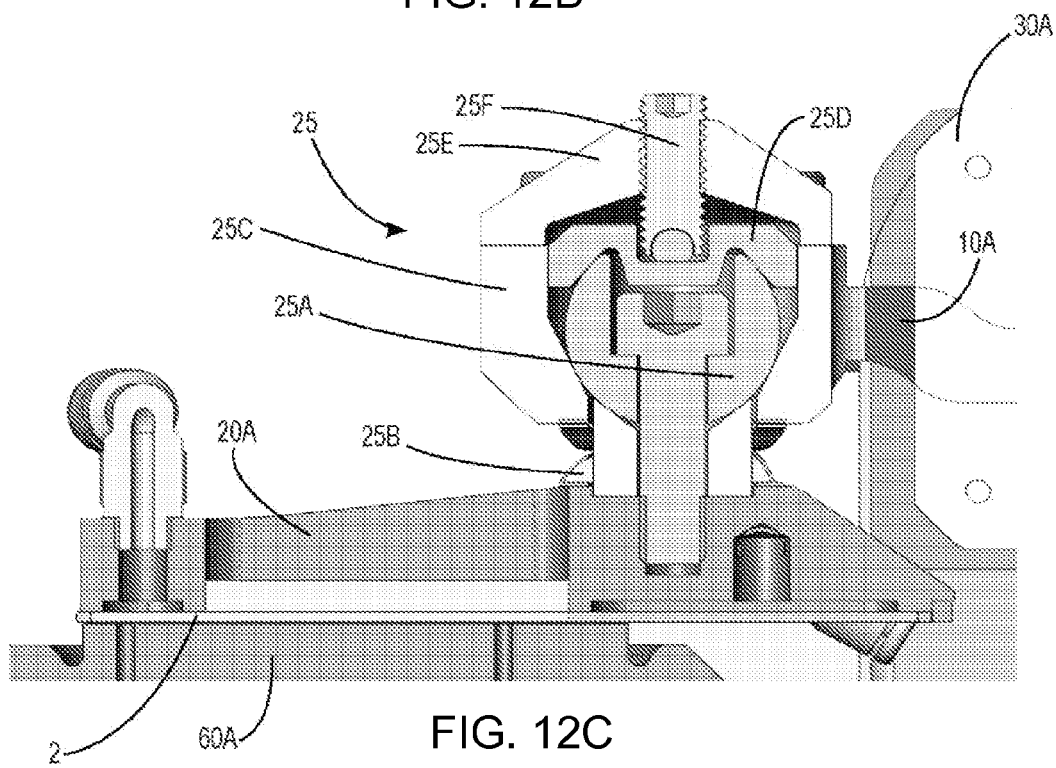
FIG. 12C is a cross-sectional view of the ball joint mechanism of FIG. 12B.

FIGS. 12B and 6C show a ball joint mechanism 25 that can be used to align a substrate gripper 20A to be parallel with a platform 60A. The ball joint mechanism 25 can include a ball member 25A that is rigidly fixed to the substrate gripper 20A, a deflection element 25B (e.g., a spring), a lower socket 25C that is rigidly connected to the substrate arm 10A, an upper socket 25D, a cap 25E that is fixed to the lower socket 25C (e.g., using fasteners), and a set screw 25F. In some embodiments, during manufacturing and/or set up of the machine 1 and substrate grippers 20A and/or 20B, the ball joint mechanism 25 can be adjusted to compensate for any misalignment that may be present due to tolerance stack-up or fabrication problems. To adjust the ball joint mechanism 25, in some embodiments, the set screw 25F is loosened and the substrate arm 10A is moved to the closed position. Since the set screw 25F is loosened, the substrate gripper 20A, while gripping a substrate 2, is able to lay substantially parallel to the platform 60A while the substrate 2 positioned along the contact offsets 70. Alternatively, in some embodiments, the number of offsets on platform 60 can be reduced or eliminated completely; a shim with a thickness corresponding to the desired separation distance can be used temporarily during set up or calibration of machine 1 in conjunction with ball joint mechanism 25 to set separation 92 at a desired distance for specimen processing. Although the ball joint mechanism 25 is loosened, the deflection element 25B applies a force to keep the substrate gripper 20A semi-fixed to the substrate arm 10A so that it is able to move independently, but it is not so loose and not free to move so much as to interfere with, or cause damage to, other components of the machine 1. Once the substrate 2 is pressed firm in a closed position so the substrate 2 is substantially parallel to the platform 60A, the set screw 25F can be tightened to secure the ball joint mechanism 25. As shown, when tightened, the set screw 25F applies a downward force on the upper socket 25D and thus applies a frictional force to the top of the ball member 25A via the upper socket 25D. Since the lower socket 25C is fixed to the cap 25E, the force created by the set screw 25F also lifts the lower socket 25C such that the lower socket 25C applies a frictional force to the bottom side of the ball member 25A to constrain the ball member 25A within the upper and lower sockets 25C, 25D. Once constrained to the ball member 25A, the substrate gripper 20A becomes fixed to the substrate arm 10A.

Typically, once the substrate gripper 20A is positioned and constrained with the set screw 25F, the ball joint mechanism 25 need not be adjusted again during normal use. However, if the substrate gripper 20A becomes misaligned and therefore the ball joint mechanism 25 requires adjustment (e.g., due to damage, machine repair, poor performance, or other reasons), the set screw 25F can be loosened, the substrate gripper 20A can be moved to a closed position to position so that a substrate gripped by the substrate gripper 20A is substantially parallel to the platform 60A, and then set screw 25F can be tightened to secure the ball joint mechanism 25.

In general, actuators 30A and/or 30B can be configured to adjust the position of substrate arms 10A and/or 10B to vary the extent of separation between the surface of platforms 60A and/or 60B and substrate 2. Varying this separation provides greater flexibility in embodiments that allow for adjusting the fluids assigned to each port, flow rates, fluid viscosities, and evacuation forces from platforms 60A and/or 60B. For example, a 100 micron separation 92 can provide sufficient specimen fixing, staining, and rinsing when fluids applied from platform 60A are dispensed at a flow rate of 115 microliters per second from ports 40A-45A having port diameters ranging from 500 microns to 1,500 microns. Alternatively, with a separation 92 distance between the surface of platform 60A and substrate 2 of approximately 200 microns, a higher flow rate for fluids dispensed from ports 40A-45A, such as 140 microliters per second, can be used for specimen processing.

Figure 10:
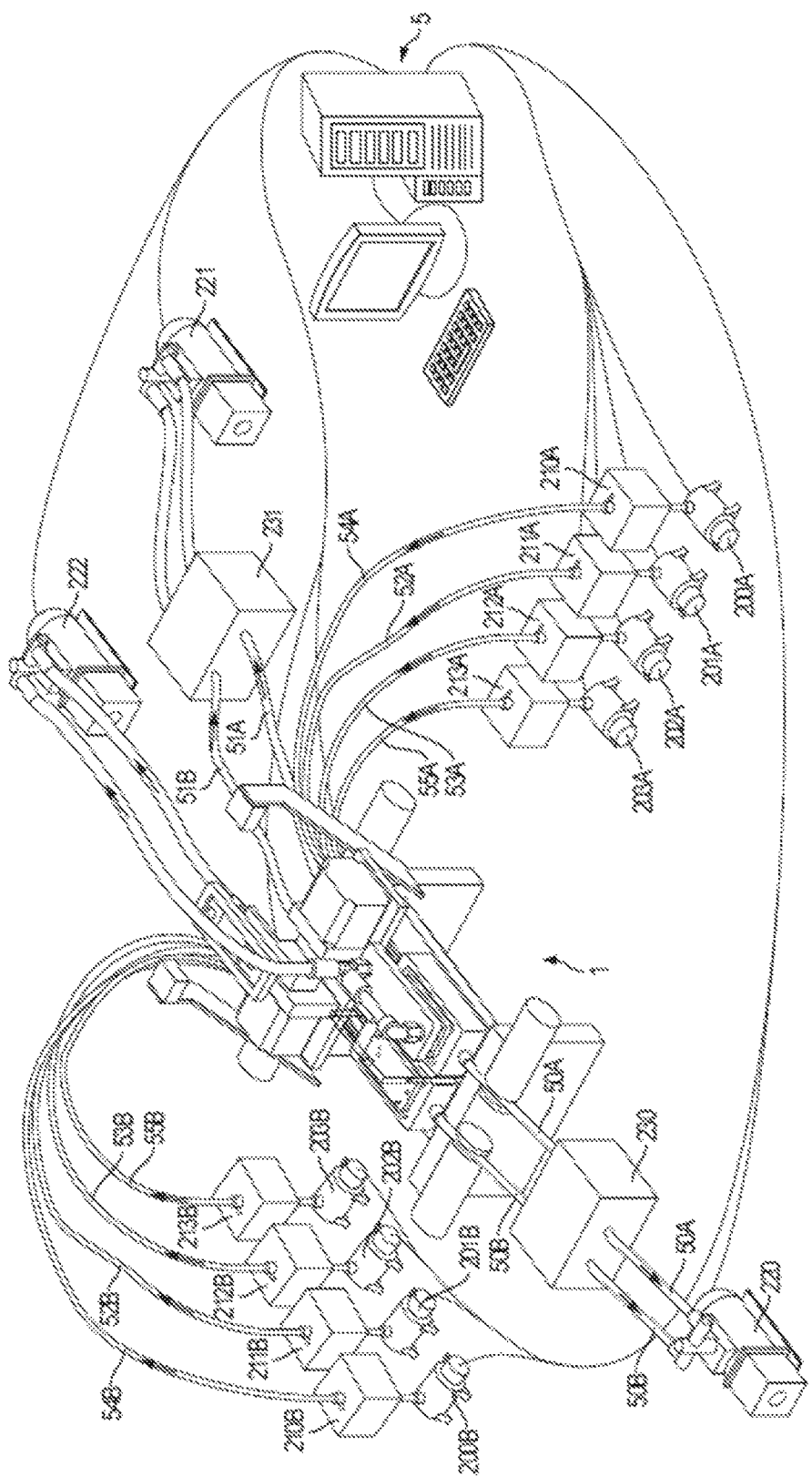
FIG. 10 is a perspective view of the apparatus of FIG. 7 showing connections between the apparatus and fluid reservoirs by means of multiple fluid conduits.

As disclosed above, machine 1 may contain a series of ports and tubes for dispersing and removing fluids applied during specimen processing. The following discussion describes various ports, tubes, and other components associated with platform 60A, but similar considerations apply to platform 60B and its associated components. FIG. 8 shows a close up view of the apparatus shown in FIG. 7, and shows in detail ports 40A-45A on platform 60A and tubes 50A-55A connected to block 80A. Tubes 52A-55A distribute certain fluids including one or more fixatives, stains, and rinse solutions across the platform, into the separation, and onto the substrate. As shown in FIG. 8, the top side of platform 60A includes six ports 40A-45A that are connected to tubes 50A-55A. Fluids are driven by one or more pumps through the tubes and ports onto substrate 2. One or more fluid reservoirs 210A-213A (such as a first stain reservoir 211A, a second stain reservoir 212A, a fixative reservoir 210A, and a rinse solution reservoir 213A), e.g., as shown in FIG. 10, can direct fluid onto platform 60A and substrate 2. The diameters of ports 40A-45A shown in FIGS. 7-9 range from approximately 500 microns to 1,500 microns, although the diameters can also be smaller or larger in certain embodiments. In some embodiments, the diameters of the vacuum ports 40A and 41A are more than twice the diameters of fluid ports 42A-45A.

Each of ports 40A-45A is typically dedicated to a particular fluid or vacuum source. Alternatively, more than one port may be used for each fluid or vacuum source, or multiple tubes from various fluid and vacuum sources may connect to a single port located on platform 60A. For example, in some embodiments, only one port on platform 60A may be used for waste removal, but when using more viscous fluids, the single port may not provide sufficient suction to evacuate residual fluid from the platform. Thus, it may be desirable in certain embodiments to provide two suction ports at different positions on the platform (e.g., one suction port at each end of the platform) for removing excess stain, fixative, and rinse fluids as shown with ports 40A-41A in FIG. 8. Further highlighting the variability of fluid-to-port configurations, in certain embodiments, a single port on platform 60A may be dedicated for a particular stain, while in other embodiments multiple ports are used for applying stains during specimen processing. Indeed, various combinations relating to the number of ports, port locations, and fluids assigned to each port and fluid tube may be used in different embodiments of the invention.

Ports 40A-45A can generally be positioned as desired on platform 60A to provide for fluid delivery to, and fluid removal from, substrate 2. Typically, each of the fluid ports is positioned on platform 60A such that the port's aperture is not positioned directly adjacent or beneath specimen 3 on substrate 2 when the specimen is undergoing processing. With certain combinations of specimens and stains, for example, if stains are dispensed from a port located directly adjacent or beneath a portion of specimen 3, a larger quantity of stain may be applied to cells in that portion (in the vicinity of the port) than to cells in other portions of the specimen. As a result, cells receiving the larger quantity of stain may appear darker in specimen images, and this non-uniform staining of specimen cells can introduce errors into diagnostic measurements and analytical outcomes based on the images. Thus, fluid ports that deliver stain to specimen 3 can be spaced a certain distance from the specimen-containing area of a substrate (e.g., a slide) to improve staining results.

In addition, the use of pairs of ports, e.g., multiple pairs of ports, located opposite each other, can also improve staining uniformity. For example, in some embodiments, two ports are used to deliver stain to specimen 3. The two ports can be located on platform 60A at positions spaced a certain distance (e.g., are offset) from the edges of specimen 3, and located opposite each other in a direction parallel to the short edges of platform 60A. When stain is dispensed from the two spaced ports, a relatively uniform quantity of stain is deposited on the cells in different regions of specimen 3, and improved staining homogeneity is observed in specimen images.

Similarly, while ports 40A-45A can generally be positioned as desired to remove excess fluids from the surface of substrate 2 using one or more vacuum sources, in some embodiments ports that are used for fluid removal are spaced at a distance from positions on platform 60A that are directly beneath cells within specimen 3 on substrate 2. Positioning waste removal ports in this manner reduces the chances that when such ports are actuated to evacuate fluids from substrate 2, cells from specimen 3 are inadvertently also drawn into the fluid removal ports. In certain embodiments, due to the difference in lengths of the long and short sides of platform 60A, the waste removal ports are spaced apart from the edge of the specimen area and arranged opposite each other along a direction parallel to the long edges of platform 60A.

Machine 1 can include or connect to a control system 5 as shown in FIG. 10, which provides another perspective view of machine 1. Control system 5 can include one or more computers each containing a central processing unit capable of executing software instructions stored on computer readable media such as a hard drive, optical drive, or memory. Additionally, control system 5 can include electrical circuitry for executing the software instructions. Control system 5 can include a user interface for receiving user commands to control the operation of machine 1. Software stored on or provided to the computer can include programs that control the operation of components of machine 1, such as fluid pumps and vacuums, during specimen processing. For example, the software can include instructions for directing the machine 1 to apply various fixatives, stains, and rinses to the specimen, and to perform several agitation steps during specimen processing.

In addition, the software can include default settings, and the user interface may contain customization features for providing the user with the ability to change these defaults settings. For example, the user interface can contain customization features for allowing a user to customize the speed, frequency, or order of fixing, staining, and rinsing phases, as well as agitation parameters (further described below). Control system 5 can also communicate via a network protocol (such as Appletalk®, IPX, or TCP/IP). For example, the network protocol may use cables (such as twisted pair cables) and/or a wireless connection such as WiFi. The control system may be connected to a laboratory information system using the network protocol. The laboratory information system can contain a server and/or database for storing information relating to specimens processed on machine 1. For example, the database may contain a table that provides information about the person or source of the specimen (e.g., name, date of birth (DOB), address, time specimen was taken, gender, etc.), information relating to processing of specimen (processed on date ##/##/####, specimen number #, etc.), a copy of any images acquired of the specimen, and copies of any results obtained by analyzing the images.

FIG. 7 also shows that machine 1 can include supports 110A and 110B to secure the device to a location within a system or a laboratory workstation. Machine 1 also includes one or more substrate arms 10A and 10B, each connected at their base to an actuator 30A and 30B. The opposite ends of the substrate arms 10A and 10B include substrate grippers 20A and 20B for receiving and holding substrates during specimen processing. Each substrate gripper 20A and 20B receives and holds a substrate 2 while machine 1 completes all specimen processing steps (described below). The substrate may be or include a microscope slide, a cover slip, or other transparent material suitable for holding a specimen during specimen processing and microscopic examination after specimen processing. The embodiment of FIG. 7 depicts a glass microscope slide, substrate 2, which includes a specimen 3. Using suction ports, substrate grippers 20A, 20B can hold the substrate 2 to substrate arms 10A, 10B during specimen processing. A suction tube 23 provides suction to the substrate grippers 20A and 20B through suction ports 21A and 21B, and 22A and 22B (note that ports 21A and 22A are positioned behind the slide 2 in FIG. 7, and are shown in dashed lines).

The machine 1 embodiment shown in FIGS. 7-9 is a dual substrate machine, capable of holding and processing a substrate on each of substrate arms 10A and 10B. Other embodiments provide for processing a single substrate or three or more substrates, sequentially or simultaneously. Further, while the embodiments depicted in FIGS. 7-12 use suction to attach the substrates 2 to the substrate arms 10A and 10B, alternative embodiments use various types of clamps, fingers, or magnets (if the substrate is magnetized) to attach a substrate 2 to a substrate arm 10A during specimen processing.

Figure 11:
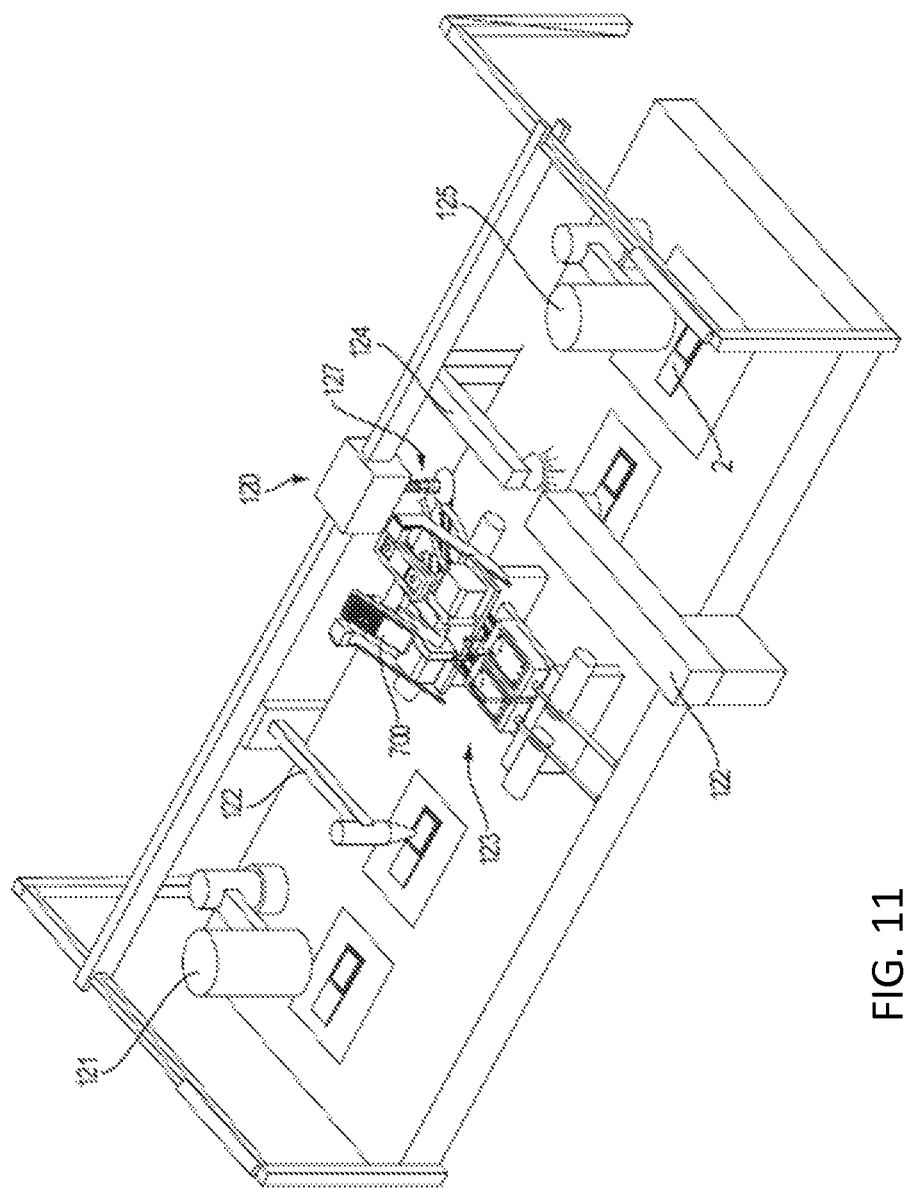
FIG. 11 is a perspective view of a specimen examination system that includes an automated substrate mover and an embodiment of a specimen preparation apparatus as described herein.
Figure 24A:
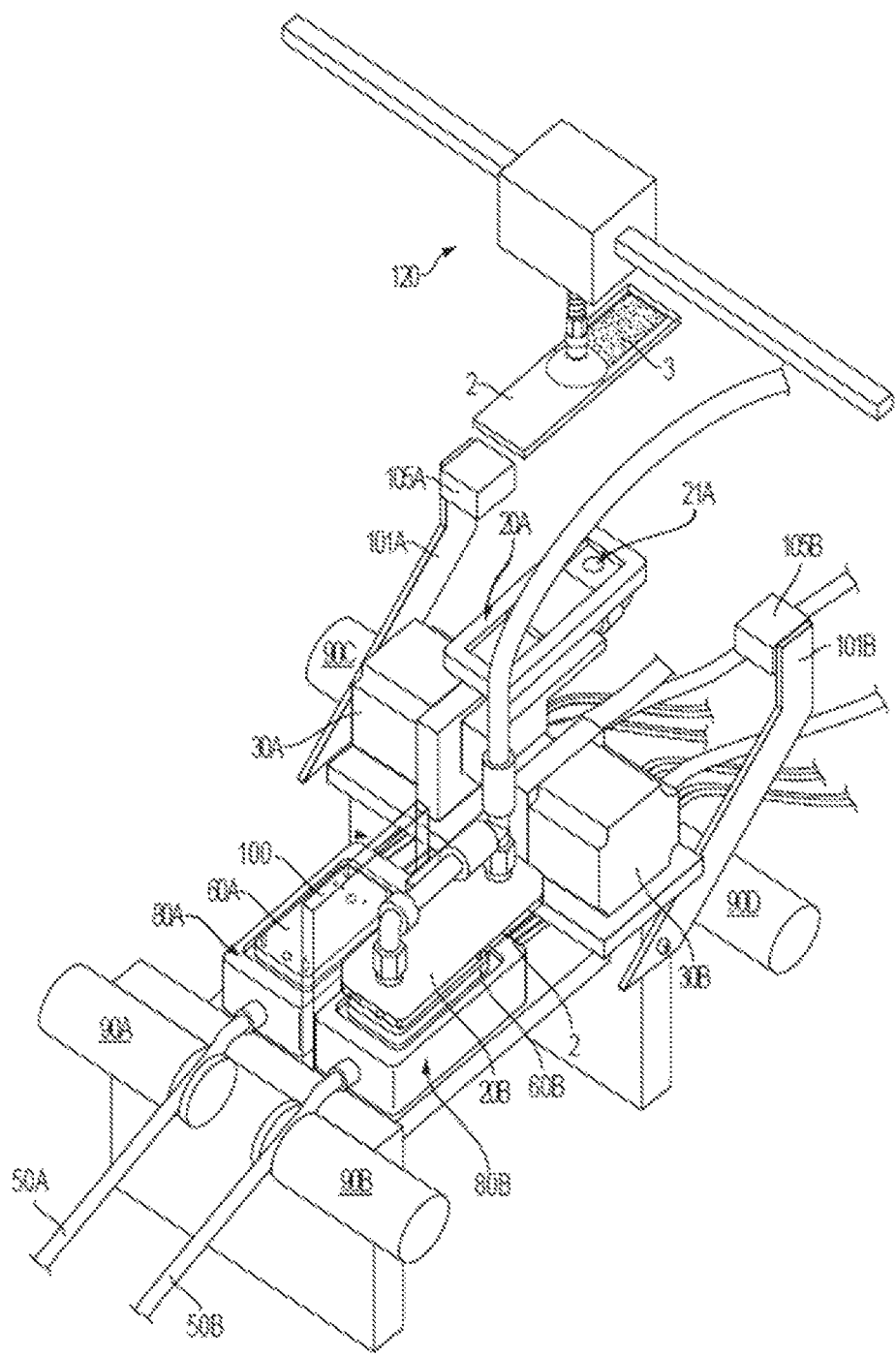
FIGS. 24A and 24B are perspective views of the apparatus of FIG. 7 that show placement of a substrate onto a substrate arm by an automated substrate mover.
Figure 24B:
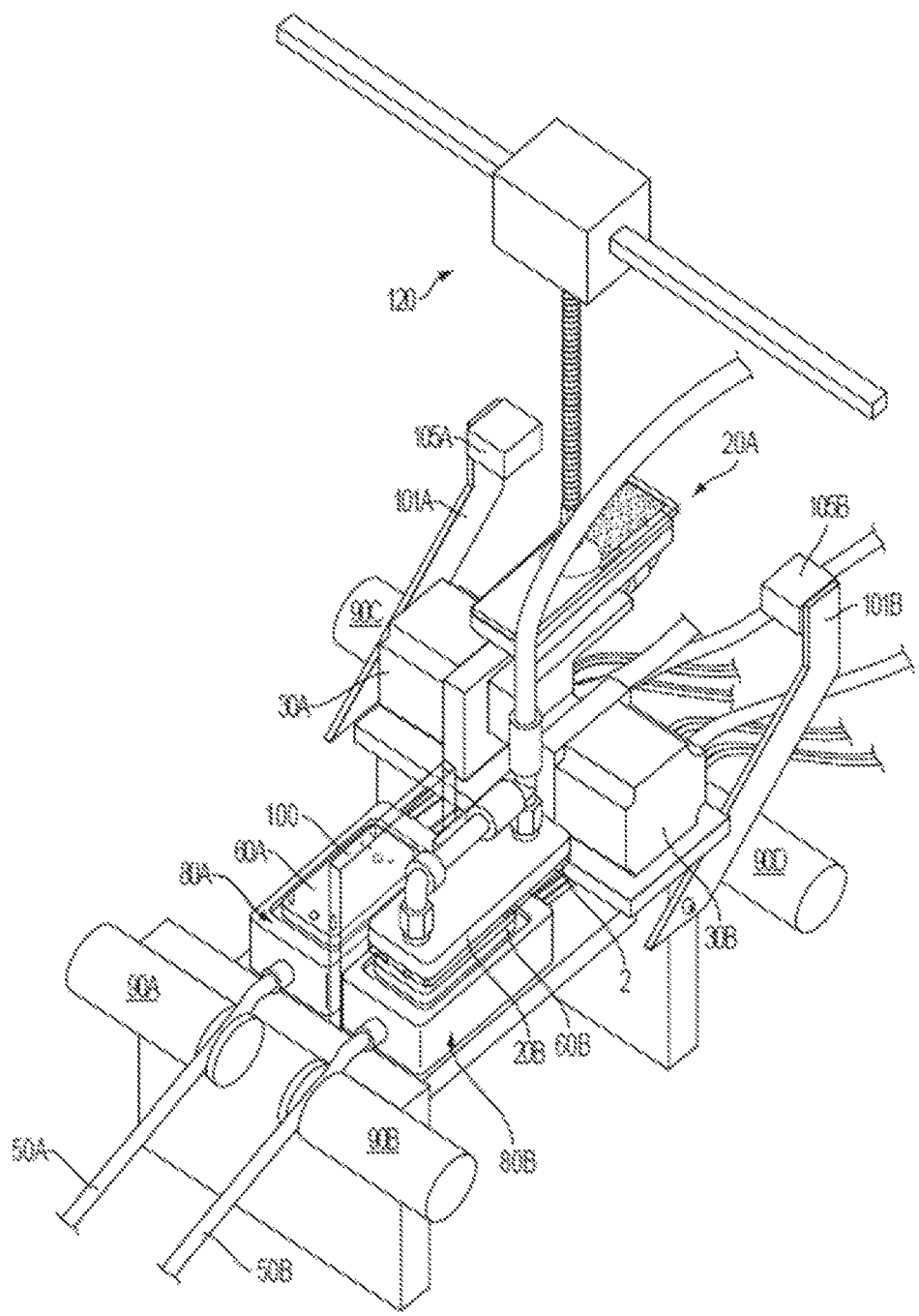

In the embodiments shown in FIGS. 11 and 24A-B, machine 1 receives a substrate 2 carrying a specimen 3 from an automated substrate mover 120 or manually from an individual. As an example, the substrate mover 120 can be a device that transports a substrate between stations (e.g., station 121 to station 122 to station 123, to station 124, and to station 125). FIG. 11 shows a system having a first label reader station 121, an applicator station 122, a staining station 123 that includes machine 1, a camera or imaging station 124, and a second label reader station 125. The first label reader station 121 is configured to read information from substrate 2 such as a bar code and/or "fingerprint" information that is used to identify the particular substrate 2 and specimen 3 thereon. The second label reader station 125 functions in the same manner, and the information it reads is used to verify that the specimen 3 that is imaged at station 124 is the same as the substrate that was processed.

Substrate mover 120 can include a gripper 127 for holding the substrate 2, and registration circuitry or software to enable the mover 120 to determine whether the substrate 2 is mounted in the mover 120. In one embodiment, substrate mover 120 can include a hydraulic cylinder for moving substrate 2 from a first station 121 to a second station 122. After specimen processing, the substrate mover 120 may remove the processed substrate from staining station 123 and transport the substrate 2 to another station for substrate examination, such as a microscope or station 124. Alternatively, an individual may manually remove a substrate from machine 1 after specimen processing.

The substrate arms 10A and 10B can rotate about an axis to enable the substrate to move from an open position for loading, to a specimen processing position, and back to the open position for unloading after specimen processing. FIG. 13A shows a flow chart 500 that includes a series of steps for moving substrate arms from an open position to a processing position. Flow chart 500 is further described below with reference to FIG. 13B, which shows a schematic diagram of machine 1.

Note that machine 1 in FIG. 7 is configured to accept and examine two substrates. In the following discussion and figures, reference may be made to only one set of components in machine 1 (e.g., substrate gripper 20A, actuator 30A, substrate arm 10A, etc.). However, it is to be understood that the same steps, features, and attributes that are disclosed in connection with one set of components can also apply to the other set of components in machine 1 (e.g., substrate gripper 20B, actuator 30B, substrate arm 10B, etc.). Thus, while the discussion herein focuses only on one set of components for clarity and brevity, it is understood that machines for specimen examination such as machine 1 can include two or even more than two sets of components, each set having some or all of the features discussed herein.

Returning to FIGS. 13A and 13B, in a first step 502 of flow chart 500, substrate mover 120 places a substrate 2 in contact with a substrate gripper 20A. In step 504, substrate 2 is positioned on the substrate gripper in a "specimen up" or "open" position. Next, in step 506, actuator 30A rotates substrate arm 10A by approximately 180° (see FIG. 13B) to position substrate 2 in a "specimen down" or "specimen processing" or "closed" position (step 508), directly above platform 60A, so that substrate 2 is in a processing position in step 510.

Then, in step 512, machine 1 stains specimen 3 positioned on substrate 2 by directing suitable fluids including stains, rinse fluids, and fixatives to be pumped from reservoirs 210A, 211A, 212A, and 213A into contact with specimen 3 through ports 42A, 43A, 44A, and 45A. Excess fluids are removed from specimen 3 by vacuum pumping through ports 40A and 41A, and are collected in waste collectors 230 and 231.

In step 514, following staining of specimen 3, actuator 30A rotates substrate arm 10 by approximately 180° (reversing the rotation of step 506) to return the substrate to the "specimen up" position. Finally, in step 516, substrate mover 120 removes the processed substrate from substrate gripper 20A. Other open or "specimen up" positions can also be used, provided that an operator or automated substrate mover can load and unload substrates from machine 1. For example, the specimen up position can be rotated 100° or more (e.g., 120° or more, 130° or more, 140° or more) from the specimen processing position. In some embodiments, the specimen up position can be rotated less than 100° (e.g., less than 90°, less than 80°, less than 70°) from the specimen processing position, provided that an operator or substrate mover can load and unload substrates from machine 1.

Actuators 30A and/or 30B may include an electric motor, pneumatics, magnetic systems, or other hardware (e.g., a worm gear) to move arm 10A and/or 10B. When substrate arms 10A and 10B are in an open position as depicted in FIG. 7, grippers 20A and 20B can each receive a substrate 2. Once loaded onto a substrate gripper 20A or 20B, actuators 30A and/or 30B then rotate arms 10A and/or 10B, and thus substrate 2, from the open ("specimen up") position to a processing position ("specimen down," as shown for arm 10B in FIG. 9) for application of fixative, stain, and rinse including agitation steps, and back to an open position for unloading after processing.

With reference to FIG. 9A, actuator 30B has rotated substrate arm 10B from the open position depicted in FIG. 1 to a "closed" or processing position. FIG. 9A shows that the substrate 2 on substrate arm 10B has been flipped over and rotated approximately 180° from its loading position shown in FIG. 7 to a downward-facing position where specimen 3 on substrate 2 is substantially parallel to the surface of platform 60B. As discussed in connection with FIG. 13A above, while substrate 2 is positioned proximal to platform 60B in the specimen processing position shown, machine 1 applies various fixatives, stains, and rinses to specimen 3 on substrate 2 through several processing phases, which will be described in greater detail below. To remove substrate 2 from the processing position, actuator 30B rotates substrate arm 10B back to the open position shown in FIG. 7 (both arms) and FIG. 9A (where only arm 10A is in the open position).

In certain embodiments, control system 5 can detect the position of the arms utilizing one or more sensors 105A and 105B to detect indicator arms 101A and 101B (as shown in FIGS. 7 and 9). Sensors 105A and 105B can be proximity sensors, e.g., photoelectric sensors, utilizing, e.g., infrared light or various other technologies (lasers, motion detectors, etc.) to detect the presence or absence of the arms. For example, proximity sensors 105A or 105B can have a detection field, and the sensors can determine whether or not a substrate arm (e.g., arm 10A and/or 10B) or a substrate gripper (e.g., gripper 20A and/or 20B) is within the detection field by detecting indicator arm 101A and/or 101B. Control system 5 can receive information from the sensors to determine the positions of substrate arms 10. For example, when substrate arm 10B (not shown in FIG. 9) is rotated to a processing position, proximity sensor 105B on the proximal end of indicator arm 101B senses target substrate gripper 20B, and notifies control system 5 that substrate arm 10B is rotated to a specimen processing position. In this position, proximity sensor 105B on the distal end of indicator arm 101B will not send a signal to control system 5, because the sensor does not detect any target (e.g., a substrate arm or substrate gripper).

When substrate arm 10B rotates to an open position (as shown in FIG. 7), proximity sensor 105B on the distal end of indicator arm 101B senses target substrate gripper 20B, and notifies control system 5 that substrate arm 10B is rotated to an open position. Stated differently, when substrate arm 10B has rotated away from the sensor 105B, the sensors send a "not present" signal to the control system 5. When arm 10B is rotated into the open position, arm 10B is closer to the sensor 105B, and the sensor can send a "present" signal to the control system 5. In alternate configurations, the sensor can be mounted on substrate 10B and can detect the presence of the indicator arm 101B. In some embodiments, control system 5 can be used to calibrate the position of actuators 30A and 30B to known open and specimen processing positions, and/or to actively monitor the movement and position of substrate arms 10A and 10B based on control signals and/or feedback received from actuators 30A and 30B.

Figure 14A:
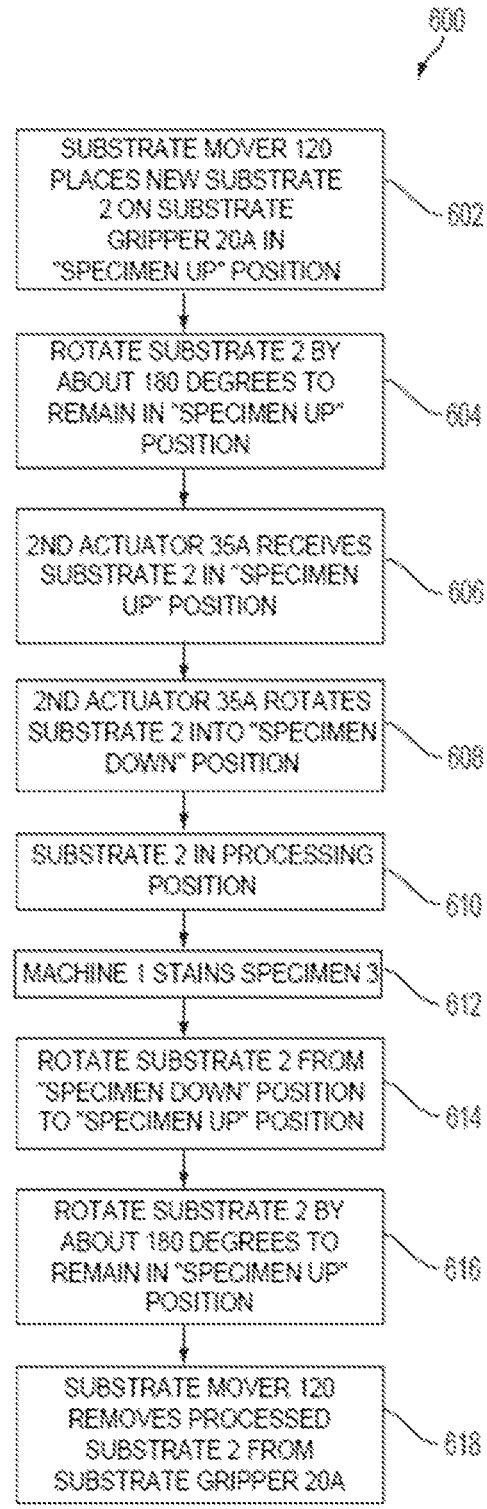
FIG. 14A is a flow chart showing an alternate series of steps for moving substrate arms from an open position to a specimen processing position.
Figure 14B:
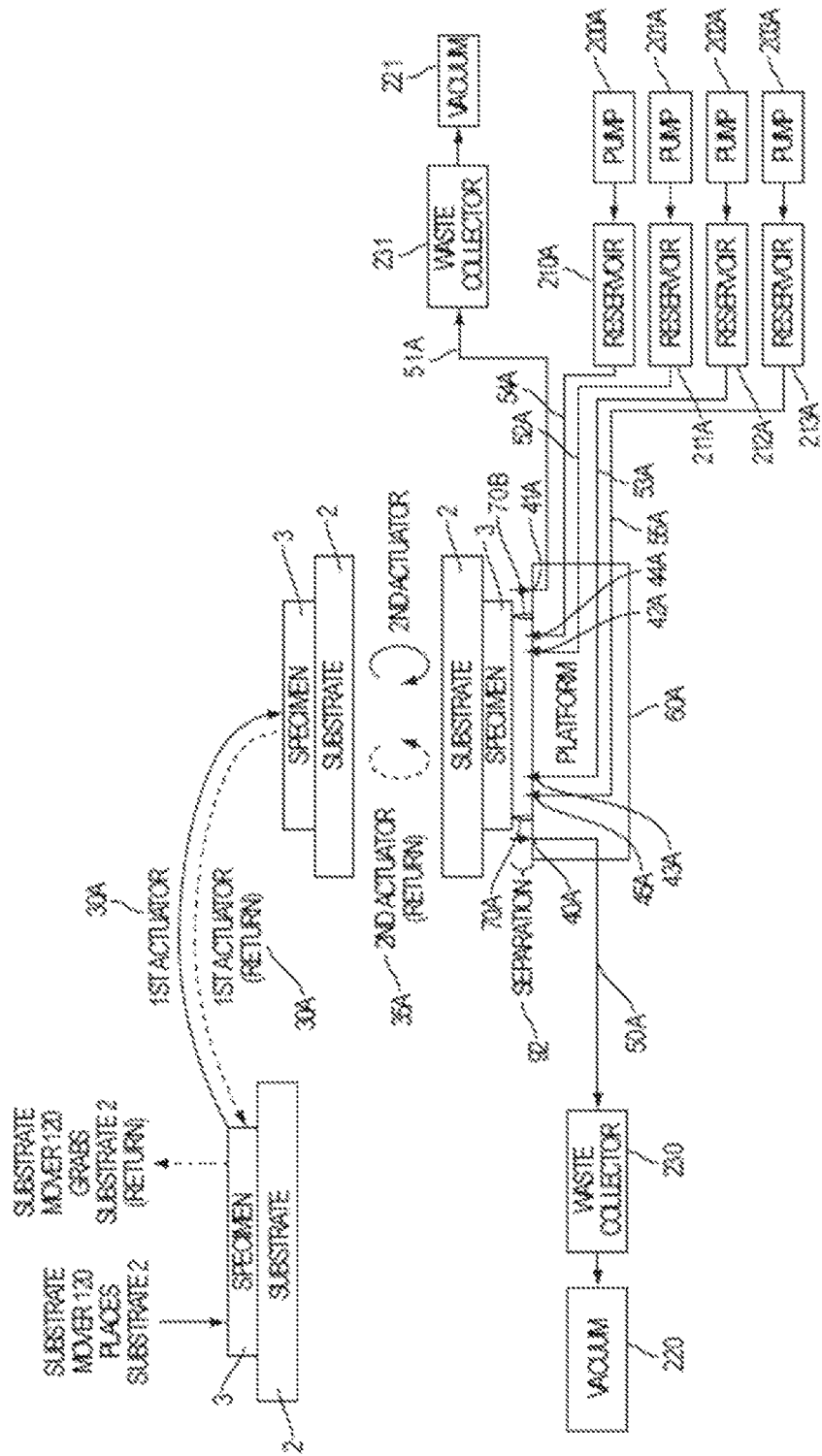
FIG. 14B is a schematic diagram of an apparatus for preparing specimens for examination that includes two actuators.

The structure and axis of rotation for substrate arms 10A and 10B in FIG. 7 may be varied in other embodiments of the invention. FIG. 14A shows a flow chart 600 that includes an alternate series of steps for moving substrate arms from an open position to a processing position. Flow chart 600 is further described below with reference to FIG. 14B, which shows a schematic diagram of machine 1.

In step 602 of flow chart 600, substrate mover 120 places substrate 2 on substrate gripper 20A in a "specimen up" orientation. Then, in step 604, a first actuator 30A rotates substrate 2 by approximately 180° in a plane perpendicular to the plane of FIG. 14B, so that substrate 2 remains oriented in a "specimen up" position above platform 60A. In step 606, a second actuator 35A receives substrate 2 oriented in the "specimen up" position. Then, in step 608, second actuator 35A (e.g., positioned between substrate arm 10A and substrate gripper 20A) rotates the substrate 2 into a "specimen down" orientation. Second actuator 35A can also move substrate 2 downward toward platform 60A so that substrate 2 contacts offsets 70A and 70B.

Next, with substrate 2 in the processing position in step 610, machine 1 stains specimen 3 on substrate 2 by applying stains, fixatives, and rinse solutions as discussed above in connection with step 512 of flow chart 500. After staining is complete, second actuator 35A rotates substrate 2 from a "specimen down" orientation to a "specimen up" orientation (step 614), and then first actuator 30A rotates substrate 2 by approximately 180° (e.g., in a plane perpendicular to the plane of FIG. 14B, reversing the rotation applied in step 606) so that the substrate remains oriented in a "specimen up" position. Finally, in step 618, substrate mover 120 removes the processed substrate from substrate gripper 20A.

Fixative Phases

Referring to FIG. 10, fluid tubes 52A-55A and 52B-55B can be positioned to deliver fixative to platforms 60A and 60B, separation 92, substrate 2, and specimen 3 during specimen processing. One or more fluid tubes 52-55A can be connected to a port inside platform 60A and a respective fixative reservoir 210A. The fluid tubes may also include a connection to a pump 200A and/or a valve capable of directing fixatives from the reservoir through the tube and a port located on the platform, and onto a substrate and specimen. As an example, pump 200A can direct a fixative solution through tube 54A, out of block 80A, through port 44A, onto platform 60A, into the separation 92 between the platform 60A and substrate 2, and onto substrate 2 containing specimen 3. After applying a specific quantity of the fixative solution to substrate 2, a vacuum or other suction source 220A and/or 221A can evacuate residual fixative solution from platform 60A, the separation 92, and substrate 2 into waste container 230A and/or 231A via one or more of ports 40A and/or 41A through waste tubes 50A and 51A.

Figure 15:
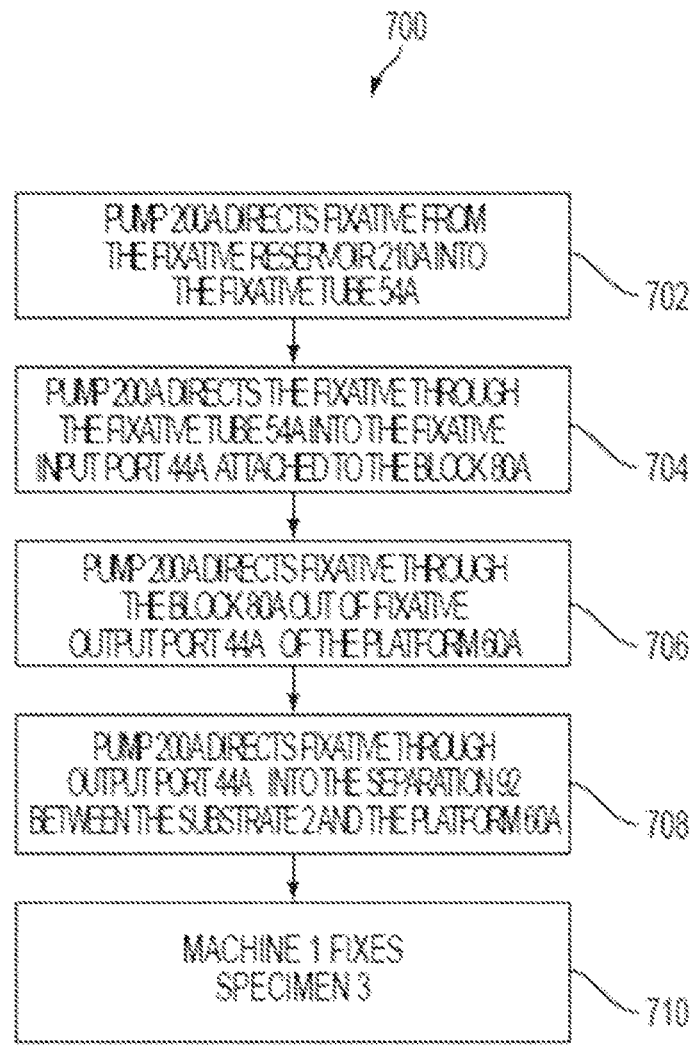
FIG. 15 is a flow chart showing a series of steps for applying fixative to a specimen.

FIG. 15 shows a flow chart 700 that includes a series of steps for applying a fixative solution to a specimen. In step 702, a pump (e.g., pump 200A) directs the fixative solution (e.g., methanol) from a reservoir (e.g., reservoir 210A) into a fixative solution tube (e.g., tube 54A). In step 704, the fixative solution is directed into port 44A attached to block 80A. Then, in step 706, the fixative solution is directed out of port 44A in platform 60A. In step 708, the fixative solution is directed out through port 44A and into separation 92 between substrate 2 and platform 60A. Finally, in step 710, specimen 3 on substrate 2 is fixed by the fixative solution.

In some embodiments, pump 200A directs the fixative solution through tube 54A and port 44A, onto platform 60A and into the separation 92 at a flow rate of about 50 µL or more (e.g., 75 µL or more, 100 µL or more, 150 µL or more, 200 µL or more, or 250 µL or more) and/or about 300 µL or less (e.g., 250 µL or less, 200 µL or less, 150 µL or less, 100 µL or less, or 75 µL or less) microliters per second for a period of about two (e.g., three, four, or five) seconds. For example, the flow rate can be about 115 µL/s (e.g., about 70 µL/s, about 100 µL/s, or about 150 µL/s) for a period of about two seconds (e.g., three seconds, or four seconds). A vacuum or other suction source 220A and/or 221A then removes residual fixative solution present in separation 92 and/or on the platform 60A and substrate 2 using ports 40A and/or 41A and waste tubes 50A and/or 51A (further described below). Next, the pump 200A can again direct the fixative solution through tube 54A and port 44A, and onto platform 60A at a flow rate of about 50 µL or more (e.g., 75 µL or more, 100 µL or more, 150 µL or more, 200 µL or more, or 250 µL or more) and/or about 300 µL or less (e.g., 250 µL or less, 200 µL or less, 150 µL or less, 100 µL or less, or 75 µL or less) microliters per second for a period of about two (e.g., three, four, or five) seconds. For example, the flow rate can be about 115 µL/s (e.g., about 70 µL/s, about 100 µL/s, or about 150 µL/s) for a period of about two seconds (e.g., three seconds, or four seconds). This process of fixing and evacuating can be repeated again, using the same or a different fixative, depending on the type of specimen requiring fixation. Further, machine 1 is capable of varying the frequency and flow rates for each fixing phase. Other flow rates sufficient to overcome any surface tension in the fluid located in separation 92 can also be used. By adjusting the frequency and/or flow rate of the fixing phases, machine 1 can achieve optimal fixation for various specimens using several different fixatives. Machine instructions for different types of specimens can be hardwired or preprogrammed in control unit 5 and selected by a system operator as needed.

In general, a wide variety of fixatives can be applied to specimens during fixative phases. For example, 85% methanol can be used as the fixative. For some stains, an ethyl alcohol or formaldehyde based fixative can be used. Embodiments of the fixative solutions disclosed herein can be used to prepare a specimen for examination.

Staining Phases

Machine 1 also includes tubes and ports configured to apply one or more dyes or stains to a specimen fixed to a substrate in one or more staining phases. Staining a specimen increases the contrast of the specimen when it is viewed or imaged under a microscope or other imaging device.

Figure 16:
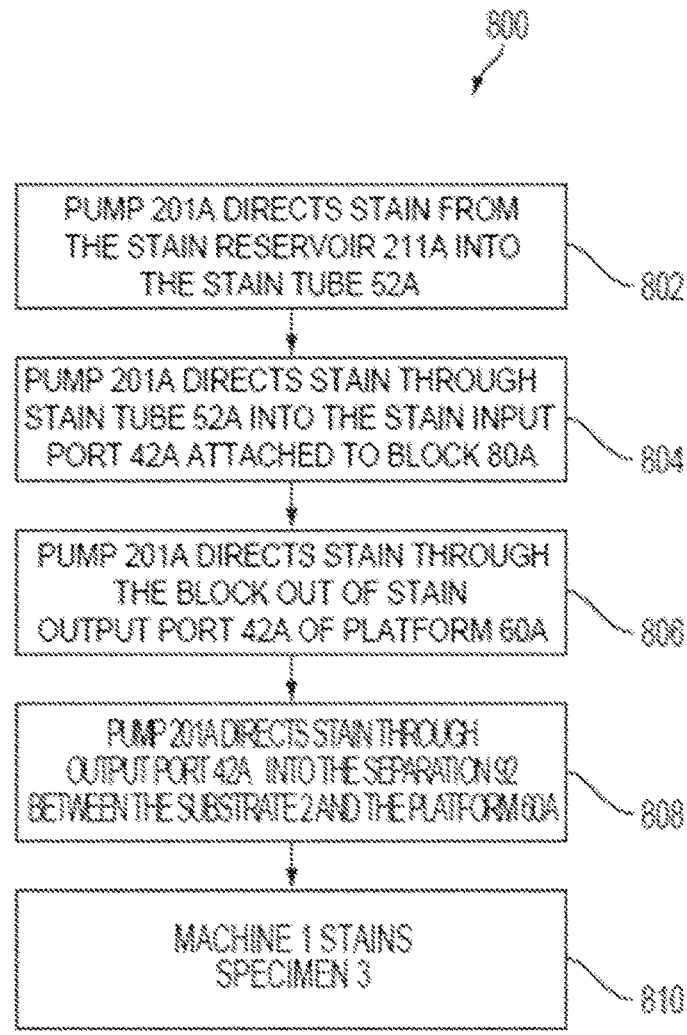
FIG. 16 is a flow chart showing a series of steps for applying stain to a specimen.

FIG. 16 is a flow chart 800 that includes a series of steps for applying stain to a specimen. In step 802, a pump (e.g., pump 201A) directs a stain solution from a reservoir (e.g., reservoir 211A) into a stain tube (e.g., tube 52A). In step 804, the stain solution is directed into a port (e.g., port 42A) attached to block 80A. Next, in step 806, the stain solution flows out of port 42A in platform 60A. In step 808, the stain solution flows into separation 92 between substrate 2 and platform 60A. Finally, in step 810, the stain is applied to specimen 3 on substrate 2.

In some embodiments, multiple tubes and ports can be used to apply stain to specimen 3. For example, a second pump (e.g., pump 202A) can direct a stain solution (e.g., the same stain or a different stain from that dispensed from reservoir 211A) from reservoir 212A through tube 53A and port 43A and onto platform 60A. In certain embodiments, two or more fluid tubes may connect to a shared stain reservoir or pump and/or valve used to direct stain through the ports and onto the platform. Referring back to FIG. 8, tube 52A may deliver red stain, such as eosin Y, to the platform, substrate 3, and specimen 2. Tube 53A may deliver blue stain, such as a thiazine dye (e.g., azure B, methylene blue). In FIGS. 7-12, the numbers, locations, and sizes of the ports on platform 60A are selected to optimize the application of stain to a specimen fixed to the substrate. If other stains are selected, a different number, locations, and sizes of ports may be preferable depending on the viscosity of the stain.

Each of ports 40A-45A (and 40B-45B) can include both an input channel for receiving fluid and an output channel for outputting fluid. In some embodiments, the output channels of the rinse 45A, fixative 44A, and staining ports 42A-43A are on the upper surface of platform 60A, and the input channels of vacuum ports 40A and 41A may be on opposite ends of the upper surface of platform 60A. The input channels of the rinse 45A, fixative 44A, and staining ports 42A-43A may be situated on the same lateral side of block 80A, and the output channels of the vacuum ports 40A and 41A can be positioned on opposite lateral sides of block 80A.

By way of example and with reference to FIGS. 8 and 16, control system 5 instructs a pump (e.g., pump 201A) in step 802 to direct a first stain solution (e.g., a stain comprising eosin Y) from a stain reservoir into fluid tube 52A. In step 804, the first stain solution enters port 42A from the fluid tube. Then, in step 806, the first stain solution leaves port 42A, and in step 808, the first stain solution is deposited into separation 92 between platform 60A and substrate 2 at a flow rate of about 50 µL or more (e.g., 75 µL or more, 100 µL or more, 150 µL or more, 200 µL or more, or 250 µL or more) and/or about 300 µL or less (e.g., 250 µL or less, 200 µL or less, 150 µL or less, 100 µL or less, or 75 µL or less) microliters per second for a period of about two (e.g., three, four, or five) seconds. For example, the flow rate can be about 115 µL/s (e.g., about 70 µL/s, about 100 µL/s, or about 150 µL/s) for a period of about two seconds (e.g., three seconds, or four seconds). In step 810, specimen 3 on substrate 2 is stained with the first stain solution. Following staining, a vacuum or other suction source (e.g., pumps 220 and/or 221) may then evacuate residual first stain solution present in separation 92, on platform 60A, and on substrate 3 using ports 40A-41A and waste tubes 50A-51A.

Machine 1 can be programmed to repeat these staining and evacuation phases after a delay (e.g., a delay of between 3 seconds and 10 seconds, such as a five second delay), following the first staining phase. A second pump 202A can be instructed by control system 5 to direct second stain solution (a solution comprising a thiazine dye) from a stain reservoir through fluid tube 53A, out port 43A at a flow rate of about 50 µL or more (e.g., 75 µL or more, 100 µL or more, 150 µL or more, 200 µL or more, or 250 µL or more) and/or about 300 µL or less (e.g., 250 µL or less, 200 µL or less, 150 µL or less, 100 µL or less, or 75 µL or less) microliters per second for a period of about two (e.g., three, four, or five) seconds onto platform 60A. For example, the flow rate can be about 115 µL/s (e.g., about 70 µL/s, about 100 µL/s, or about 150 µL/s) for a period of about two seconds (e.g., three seconds, or four seconds). A vacuum or other suction source (e.g., pump 220A and/or 221) may then evacuate residual second stain solution present in separation 92 and/or on platform 60A and/or on substrate 2 using ports 40A-41A and waste tubes 50A-51A. As with the fixing phases, machine 1 is capable of varying the frequency and flow rates for each staining phase. The flow rate may range, e.g., from 50 to 300 microliters per second, or may be smaller or greater than the outer limits of this range (e.g., 10 to 500 microliters per second) provided the flow rate is sufficient to overcome any surface tension present in the fluid located in separation 92.

Exemplary stains that can be applied to specimens include, but are not limited to: Wright-Giemsa stain, Giemsa stains, and Romanowsky stains, including embodiments of the first and second staining solutions disclosed herein. Other agents such immunocytochemical reagents or other markers of specific cell components can also be applied to specimens.

Waste Fluid Removal

As referenced above, a vacuum or other suction source 220 and/or 221 can evacuate residual fluid from substrate 2, separation 92, and platform 60A during or between fixing and staining phases. Referring to FIG. 7, one or more waste tubes can be connected to sides 82A and 84A of block 80A. Waste or vacuum tubes 50A and 51A are used to withdraw fluid and small particulate matter from platform 60A, separation 92, and substrate 2 into a waste container or other location separate from machine 1. With reference to FIG. 8, waste tubes 51A and 51B may be connected to separate vacuum sources 220 and 221, and waste containers 230 and 231, at the distal ends of the waste tubes. Alternatively, two or more waste tubes can be connected to a single vacuum source, and the same waste container, as shown in FIG. 10. Waste tubes 50A and 50B may extend through pinch valves 90A and 90B, respectively.

A vacuum or other source (e.g., vacuum pump 220 and/or 221) for applying suction may be connected to one or more of waste tubes 50A, 50B, 51A, and 51B to draw fluid from the platforms 60A and/or 60B, separation 92, and substrate 2 into waste containers 230 and 231. The vacuum force applied within the waste tubes may be equivalent to negative one to negative five pounds per square inch ("psi") to provide sufficient suction for removing fluids when the separation between the substrate 2 and the platform is between 100 to 200 microns. In general, as used herein, "negative" pressure refers to a pressure less than the ambient pressure within machine 1 or the environment surrounding machine 1. For example, in some embodiments, the environment surrounding machine 1 has an ambient air pressure of approximately one atmosphere. "Negative" pressures refer to pressures that are less than this ambient air pressure (e.g., a pressure of negative one psi applied to a fluid is a pressure of one psi less than the ambient air pressure exerted on the fluid). Other vacuums ranging from 0.1 psi to 14 psi, or greater, can be used provided such vacuums are sufficient to overcome any surface tension in the fluid present in the separation. In addition, immediately prior to applying vacuum to evacuate fluids from the separation, actuator 30A can raise the proximate edge of substrate 2 a distance of 15-35 microns from the specimen processing position. This increased separation between substrate 2 and platform 60 can improve evacuation of any residual fluids in separation 92 during a vacuum phase.

Figure 17A:
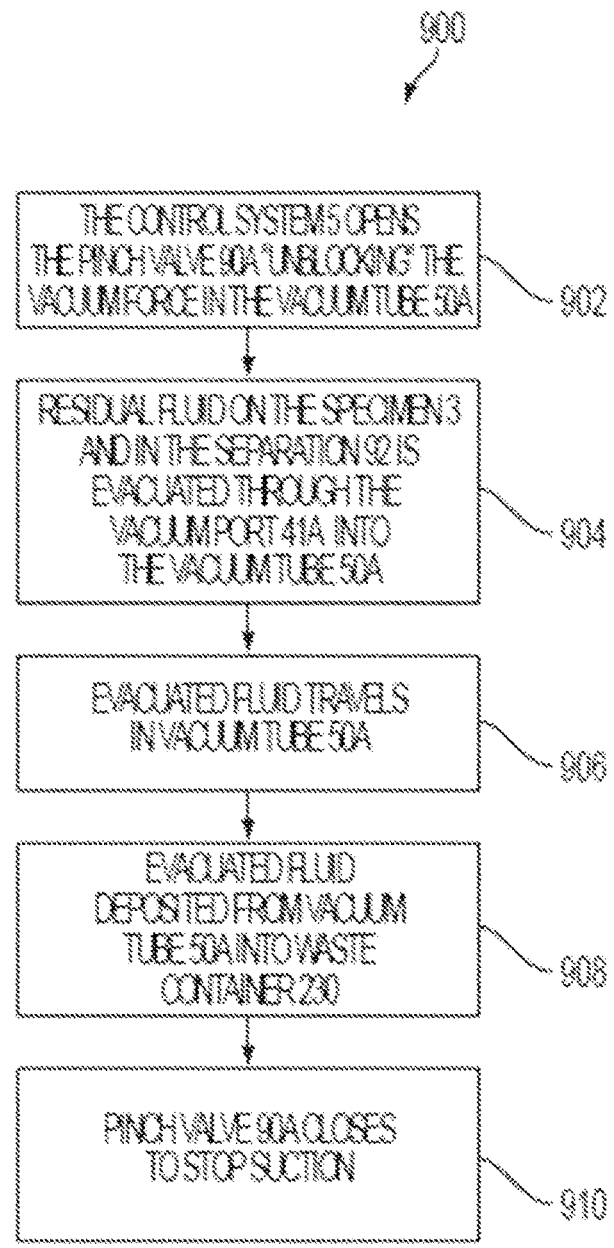
FIG. 17A is a flow chart showing a series of steps for removing excess fluid from a substrate.

In some embodiments, control system 5 is configured to vary the frequency and vacuum applied for fluid removal during specimen processing. FIG. 17A includes a flow chart 900 that features a series of steps for removing excess fluid from a substrate. Following a fixing phase, for example, control system 5 can open pinch valves 90A and/or 90C in step 902 and apply a vacuum of 5 psi in the waste tubes (e.g., waste tubes 50A and 51A) for a five second period. During this period, a fixative solution is removed (step 904) from the separation, substrate, and platform through ports 40A and 41A. The fluid travels through the waste tubes in step 906, and is deposited in into one or more waste containers (e.g., containers 230 and/or 231) in step 908. Once the evacuation period expires, control system 5 can instruct one or more of the pinch valves 90A, 90C to close off the waste tubes 50A and/or 51A in step 910, thereby preventing further evacuation by the vacuum 220-221. Control system 5 may direct machine 1 to repeat this fluid removal step after each fixing phase.

Figure 17B:
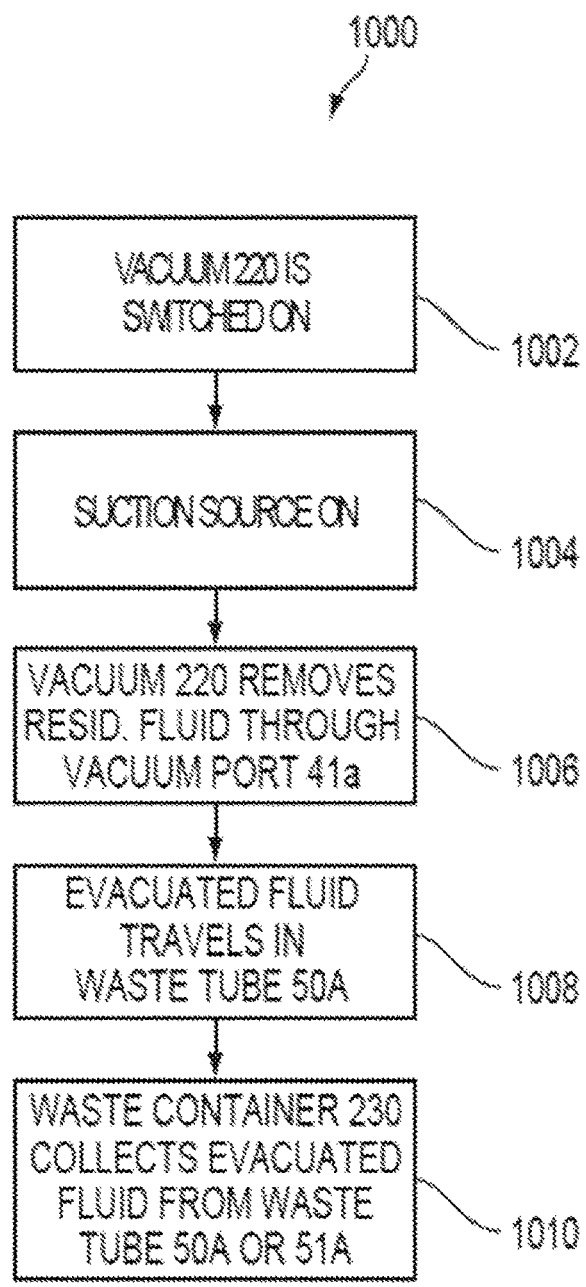
FIG. 17B is a flow chart showing an alternate series of steps for removing excess fluid from a substrate.

FIG. 17B includes a flow chart 1000 that features an alternate series of steps for removing excess fluid from a substrate. The method in flow chart 1000 does not use pinch valves to seal waste tubes. Instead, after a staining phase, suction source 220 and/or 221 are initialized in step 1002 and enter an active state in step 1004. The suction source applies a pressure of 3 psi in waste tubes 50A and/or 51A for a four second period to remove stain from separation 92, substrate 2, and platform 60A through ports 40A and 41A in step 1006. The evacuated fluid travels through waste tubes 50A and/or 51A in step 1008, and is deposited in one or more waste containers 230, 231 in step 1010. Machine 1 may repeat this fluid removal step after each staining phase. By varying the frequency and pressure applied during fluid removal steps, machine 1 may achieve optimal fixing and staining of specimens.

Pinch valves 90A, 90B, 90C, and 90D close off waste tubes 50A, 50B, 51A, and 51B, as shown in FIG. 7. The pinch valves 90A-90D may be mechanically, electrically, hydraulically, or pneumatically actuated through actuators contained within or external to the valves. Pinch valves 90A-90D operate to prohibit fluid flow through waste tubes 50A, 50B, 51A, and 51B. For example, when changing or emptying a full waste container 230 from machine 1, it may be desirable to close the pinch valves (90A-90D) to prevent leakage of residual fluids present in the waste tubes. Different valve types or other mechanisms such as clamps or stoppers may be used with embodiments of machine 1 to close the waste tubes 50A, 50B, 51A, and 51B.

Rinsing Phases

Rinse solutions can be applied during specimen processing with machine 1 in one or more rinse phases. For example, it may be desirable to cleanse the substrate 2, separation 92, and platforms 60A and/or 60B between fixing phases, between staining phases, and/or between fixing and staining phases.

Figure 18:
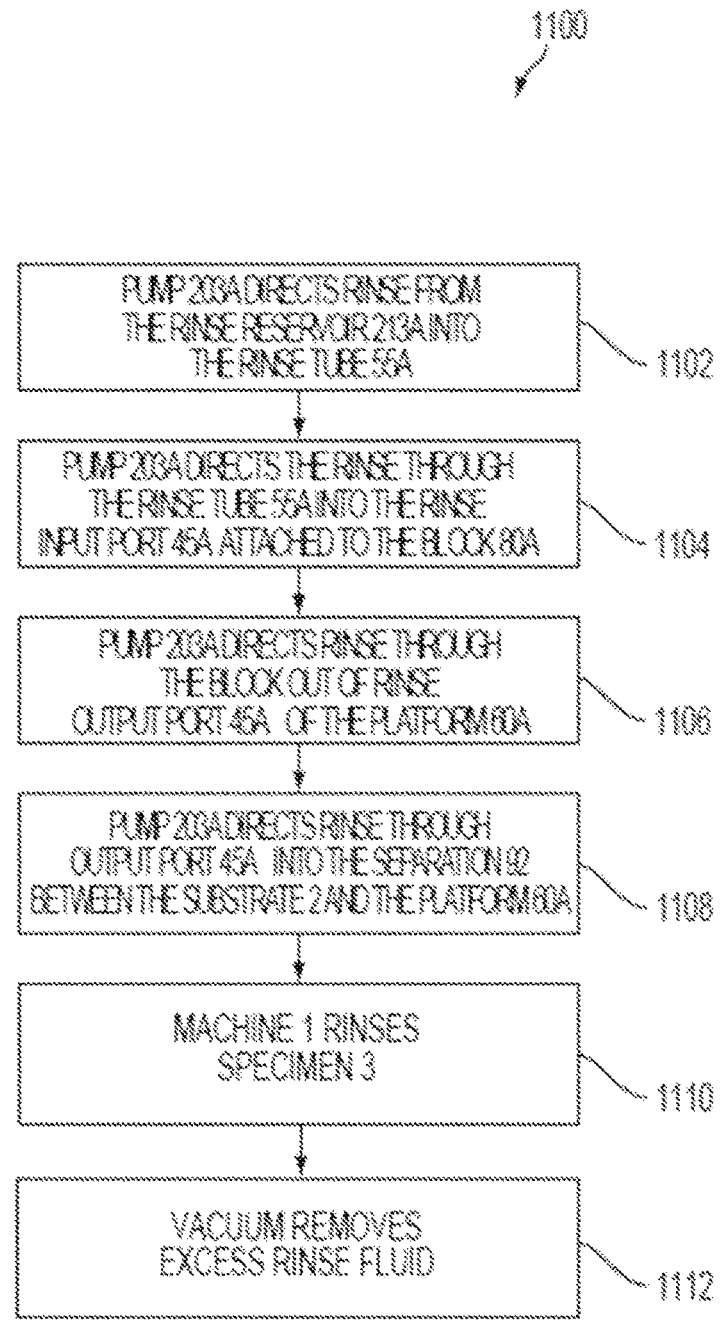
FIG. 18 is a flow chart showing a series of steps for rinsing a specimen.

FIG. 18 includes a flow chart 1100 featuring a series of steps for rinsing a specimen. In step 1102, a pump (e.g., pump 203A) directs rinse solution (e.g., comprising distilled water) from a reservoir (e.g., reservoir 213A) into a rinse tube (e.g., rinse tube 55A). In step 1104, the rinse solution enters port 45A connected to block 80A. In step 1106, the rinse solution flows onto platform 60A through the output channel of port 45A, and in step 1108, the rinse solution enters separation 92 between substrate 2 and platform 60A. In step 1110, rinsing of specimen 3 is performed. Finally, in step 1112, a vacuum source 220, 221 applies suction to one or more of waste tubes 50A and 51A to remove rinse solution from separation 92 and substrate 2; the rinse solution is transported to waste container 230 and/or 231. In some embodiments, the foregoing steps are repeated in a second rinse phase.

In some embodiments, control system 5 may direct pump 203A to apply the rinse solution at a flow rate of about 50 µL or more (e.g., 75 µL or more, 100 µL or more, 150 µL or more, 200 µL or more, or 250 µL or more) and/or about 300 µL or less (e.g., 250 µL or less, 200 µL or less, 150 µL or less, 100 µL or less, or 75 µL or less) microliters per second for a period of about two (e.g., three, four, or five) seconds. For example, the flow rate can be about 115 µL/s (e.g., about 70 µL/s, about 100 µL/s, or about 150 µL/s) for a period of about two seconds (e.g., three seconds, or four seconds). As with fixing phases, control system 5 may vary the duration and flow rate of each rinse phase and the number of rinse phases. In addition, control system 5 may adjust the placement of one or more rinse phases during specimen processing. Control system 5 may, for example, direct that a rinse phase occur once, after completion of all fixing phases, and that a second rinse phase occur once, after completion of all staining phases. Alternatively, rinse phases may be interspersed between two or more fixing phases or between two or more staining phases.

In some embodiments, a staining procedure can include (1) a fixing phase, (2) a second fixing phase, (3) a first staining phase using the first staining solution, (4) a second staining phase using the second staining solution, (5) a rinsing phase, and (6) a second rinsing phase. In some embodiments, the various (e.g., first and second) staining phases and/or solutions can be used in any order and/or repeated in any order. For example, the first and second staining phases and/or solutions can be interchanged. Each phase can include a deposition flow rate of about 50 μL or more (e.g., 75 μL or more, 100 μL or more, 150 μL or more, 200 μL or more, or 250 μL or more) and/or about 300 μL or less (e.g., 250 μL or less, 200 μL or less, 150 μL or less, 100 μL or less, or 75 μL or less) microliters per second for a period of about two (e.g., three, four, or five) seconds. For example, the flow rate can be about 115 μL/s (e.g., about 70 μL/s, about 100 μL/s, or about 150 μL/s) for a period of about two seconds (e.g., three seconds, or four seconds).

Agitation Phases

Figure 19:
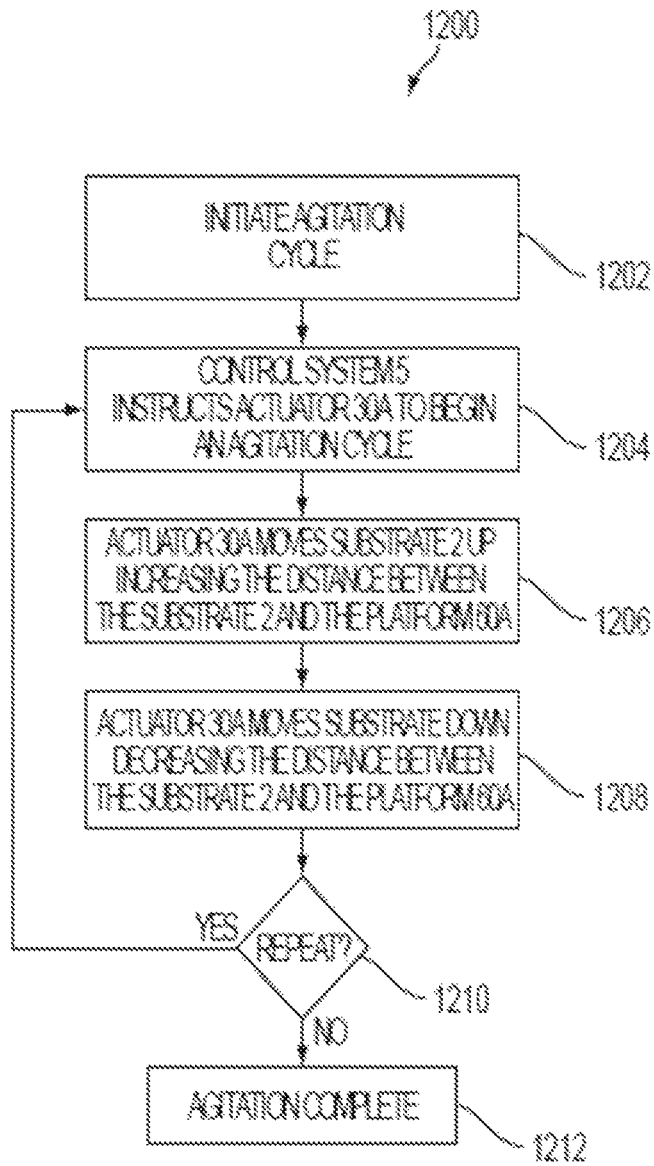
FIG. 19 is a flow chart showing a series of steps for agitating a specimen.

Specimen processing in certain embodiments may include one or more agitation phases to disperse a fixative solution, stain solution, and/or rinse solutions throughout separation 92, substrate 2, and platforms 60A and/or 60B during the fixing, staining, and/or rinsing phases. FIG. 19 includes flow chart 1200 that features a series of steps for agitating a specimen. Actuator 30A and/or 30B, shown in FIG. 9, can provide fine movement adjustment for changing the position of substrate 2 relative to platform 60A and/or 60B.

Control system 5 can include software and/or hardware for instructing the actuator 30A and/or 30B to initiate an agitation phase. Actuator 30A and/or 30B can be configured to move substrate arm 20A and/or 20B up and down upon an agitation initiation command from the control system. The agitation phase may repeat for a predetermined number of cycles. The term "cycle," as used herein, refers to motion from a starting position in an upward direction, followed by movement in a downward direction opposite to the upward direction. In some embodiments, one or more agitation cycles return substrate 2 to the starting position at the conclusion of each cycle, or at least at the conclusion of some cycles. In certain embodiments, substrate 2 does not return to the starting position at the conclusion of some or all of the agitation cycles, but each cycle still includes an upward motion followed by a downward motion. Actuator 30A and/or 30B typically continues moving substrate 2 in one or more agitation cycles until a stop command is sent to the actuator from the control system 5. An agitation phase may temporarily increase the separation size (separation distance) between substrate 2 and the surface of platform 60A and/or 60B, and then return the substrate to the specimen processing position. In addition, an agitation phase may include a series of movements that shift substrate 2 between an angular position relative to the surface of platform 60A and/or 60B and the specimen processing position. Surface tension in the fluids dispensed into the separation between the platform and substrate 2 causes a redistribution of fluid molecules on the substrate when the substrate moves from the specimen processing position during the agitation phase and can advantageously improve fluid distribution across the specimen.

Other methods can also be used to move substrate 2 relative to the platforms during agitation phases. For example, in some embodiments, the positions of one or more of offsets 70A-D and/or 71A-D (e.g., the amount by which the offsets extend above the surfaces of platforms 60A and/or 60B) can be rapidly adjusted to agitate specimen 3. In certain embodiments, the positions of platforms 60A and/or 60B can be adjusted to cause agitation of specimen 3. For example, platforms 60A and/or 60B can be moved alternately up and down (e.g., corresponding to the direction of movement of substrate 2 described above) to cause agitation of specimen 3.

In some embodiments, agitation of specimen 3 can be effected by varying the extent to which actuator 30A and/or 30B drives substrate 2 towards offsets 70A-D and/or 71A-D when the substrate arms are made of a material that flexes, as discussed below. Strain gauges can be used to measure and adjust the frequency of the agitation applied to substrate 2 by detecting the variation in strain in the substrate arms as a function of time.

Referring to FIG. 19, in a first step 1202, an agitation phase is initiated. In step 1204, control system 5 instructs actuator 30A to begin an agitation cycle. In response to this instruction, actuator 30A rotates substrate 2 upward in step 1206, increasing the distance between substrate 2 and platform 60A. Then, in step 1208, actuator 30A rotates substrate 2 downward toward platform 60A, reducing the distance between the substrate and platform 60A. In decision step 1210, if the agitation phase is to continue, control returns to step 1204 and the rotation of substrate 2 by actuator 30A occurs again in another agitation cycle. If the agitation phase is to terminate, then control passes from step 1210 to step 1212, where substrate 2 is returned to its initial position with agitation complete.

The agitation phase can include one or more agitation cycles applied through actuator 30A and/or 30B. Further, agitation phases can occur once or multiple times during each of the fixative solution, stain solutions, and/or rinse phases and in varying frequencies between each of the fixing, staining, and/or rinsing phases. For example, and referring to FIG. 9, actuator 30A and/or 30B may raise the proximate edge of substrate 2 vertically a distance of 35 microns from the specimen processing position and subsequently return substrate 2 to the specimen processing position three times, once after each fixing, staining, and rinse phase. Actuator 30A and/or 30B may complete each agitation cycle in two seconds (e.g., one second to raise the proximate edge of substrate 2 vertically a distance of 35 microns from the specimen processing position and one second to return the substrate to the specimen processing position). Machine 1 is capable of carrying out instructions to vary the agitation frequency and distance for each agitation cycle and/or phase. For example, an agitation phase may include actuator 30A and/or 30B raising the proximate edge of substrate 2 vertically a distance of 5 microns from the specimen processing position and then returning the substrate to the specimen processing position, 10 to 20 times per second.

Alternative combinations of agitation distances and frequencies can also be used. For example, in some embodiments, the agitation distance is 25 microns or more (e.g., 50 microns or more, 100 microns or more, 150 microns or more, 200 microns or more, 250 microns or more, 300 microns or more, 500 microns or more, 700 microns or more, 1 mm or more. For example, in certain embodiments, the agitation distance is between 35 microns and 350 microns.

In some embodiments, the agitation cycle frequency is one cycle per second or more (e.g., two cycles per second or more, three cycles per second or more, four cycles per second or more, five cycles per second or more, seven cycles per second or more, ten cycles per second or more).

Additional agitation techniques can also be used. For example, in some embodiments, substrate gripper 20A and/or 20B may include an actuator that rotates the substrate about an axis perpendicular to the rotational axis of actuator 30A and/or 30B depicted in FIGS. 7 and 9.

Alternatively, platform 60A and/or 60B may be equipped with an offset adjuster for raising or lowering the one or more offsets 70A-D and/or 71A-D during fixing, staining, and rinsing phases. To implement the offset adjuster, platform 60A and/or 60B can include offsets that are attached to an internal plate in the platform. The height of the plate may be varied using an internal actuator, thus varying the height of the offsets. Alternatively, the position of the offsets 70A-D and 71A-D relative to substrate 2 can be changed by instructing the actuator to move platform 60A and/or 60B, or block 80A and/or 80B, thereby changing the separation distance during the agitation phase. Control system 5 can adjust the frequency of fluid cycles, flow rate, offset height, separation distance, and agitation parameters and frequency to process specimens more efficiently, using significantly less fluid volumes during the specimen preparation process as compared to conventional staining and preparing techniques.

In some embodiments, substrate arms may be made of a material that flexes such that if a substrate in the specimen processing position rests against only two offsets extending from the platform, an actuator or other motive force element may rotate the slide further towards the platform surface until the slide rests against all four offsets. Varying the position of the substrate between these two positions may accomplish sufficient agitation during specimen processing. Substrate arms may include strain gauges to monitor the strain in the substrate arm, and may be used to inform control system 5 of the position of the substrate relative to the platform offsets. In addition, the control system may include information corresponding to the thickness imperfections of the substrate, which the control systems may account for when placing the substrate in the specimen processing position or during agitation phases.

Drying Phases

Figure 20:
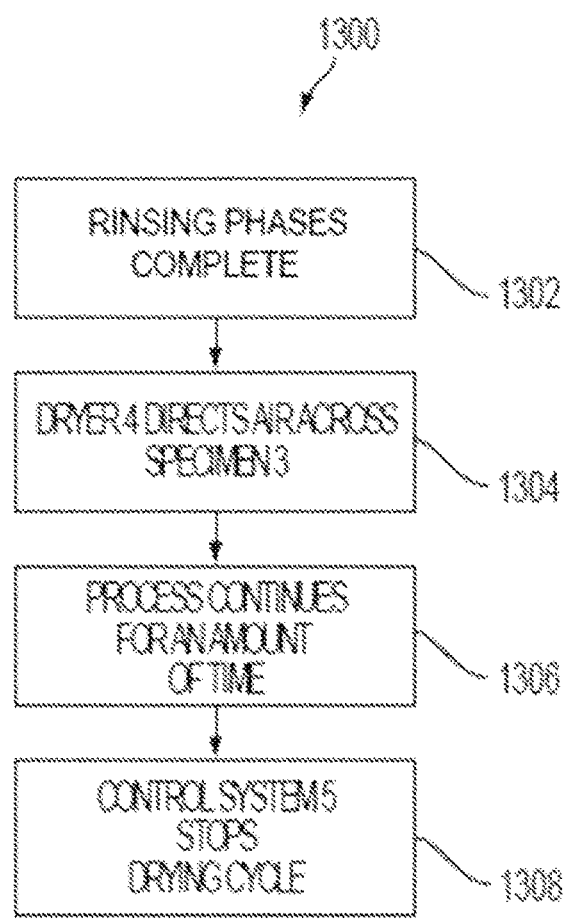
FIG. 20 is a flow chart showing a series of steps for drying a specimen.

In certain embodiments, the control system 5 can dry the specimen using a dryer 4 attached to machine 1. FIG. 20 includes a flow chart 1300 that features a series of steps for drying a specimen. Following the initial step 1302 in which the completion of the staining and other phases (e.g., one or more rinsing phases) is verified, in step 1304 the dryer 4 directs a flow of air across the specimen. The drying process continues in step 1306, until a signal is received from the control unit to stop the drying. When the signal is received, the dryer stops the flow of air across the specimen and the drying phase terminates at step 1308.

In general, machine 1 can be controlled to vary the temperature of the air, the flow rate, the duration of the applied air flow, and the phase(s) during specimen processing for drying the specimen 3. For example, after completing a staining phase, dryer 4 can direct a flow of air at approximately 120° F. at a rate of 10 liters per minute for a period of 7 seconds across the specimen. Other air temperatures (e.g., from ambient temperature up to 300° F.), air flow rates (e.g., one liter per minute to 100 liters per minute), and air flow periods (e.g., from a few seconds to several minutes) can also be used.

Specimen Examination Systems

Figure 21:
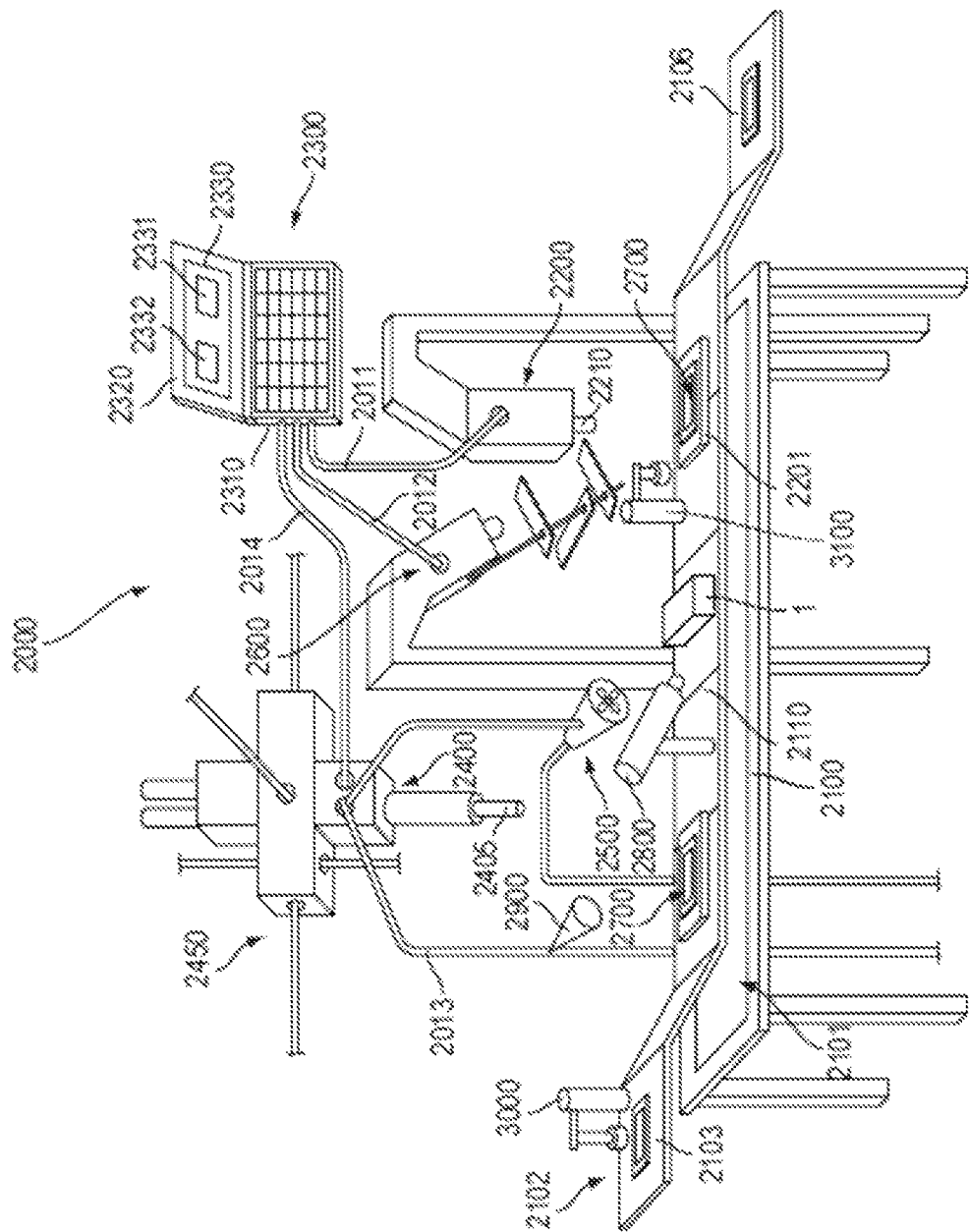
FIG. 21 is a perspective view of a specimen preparation apparatus as used in a larger specimen examination system.

The automated specimen preparation machines and apparatus disclosed herein, including machine 1, can generally be used with, and/or incorporated into, larger specimen examination systems, such as those described in U.S. application Ser. Nos. 12/430,885 and 13/293,050, the entire contents of which are incorporated herein by reference. For example, FIG. 21 shows a schematic diagram that illustrates one possible embodiment of a specimen examination system 2000. System 2000 includes a platform 2100, a light receiving device 2200, a computer 2300, an applicator 2400, a gas circulation device 2500, a light source 2600, a dispenser 2800, a discharge device 2900, a slide labeler 3000, and slide label reader 3100. An advancer 2110 may be configured to receive one or more slides or other substrates 2700. The advancer 2110 may be attached to a surface, such as the top surface 2101, of the platform. The advancer 2110 may take the form of a belt, and the system may use a mechanical arm, gravity, magnetism, hydraulics, gears, or other locomotion techniques to move substrate-mounted specimens along the surface 2101 of the platform.

The platform 2100 may also include a feeder 2102 and a collector 2106 for respectively feeding and collecting substrates 2700 (e.g., slides) from or to a stack or rack. Feeder 2102 may be equipped with a feeder propulsion mechanism 2103 (such as rubberized wheels) for pushing the specimens onto advancer 2110. Alternatively, a mechanical arm could be used to grab substrates 2700 and place the substrates on the advancer directly. Alternate mechanisms to propel the substrates out of feeder 2102 may be used such as magnets or hydraulics. The feeder may include a sensor for determining how many slides are present. The sensor could measure the weight of substrates 2700 for example to determine how many substrates are present. Collector 2106 can also include a sensor for determining how many substrates are present. The sensor can be configured to inform the computer 2300 when a preset number of specimens have been analyzed, and/or can inform the computer of the receipt of a specimen mounted on a substrate on an ongoing basis.

Light receiving device 2200 can be a microscope (such as brightfield microscope), a video camera, a still camera, or other optical device that receives light. Embodiments that include a standard brightfield microscope can also include an automated stage (e.g., a substrate mover 2201) and an automated focus. In some embodiments, a microscope can be attached to a motorized stage and a focus motor attachment. The microscope can have a motorized nosepiece for allowing different magnification lenses to be selected under the control of computer 2300. A filter wheel can be used to enable the computer 2300 to automatically select narrow band color filters in the light path. LED illumination can be substituted for the filters, and the use of LEDs can reduce the image acquisition time as compared to the time required for filter wheel rotation. For example, a 1600×1200 pixel FireWire® (IEEE1394 High Performance Serial Bus) camera can be used to acquire the narrow band images.

In some embodiments, light receiving device 2200 receives light reflected from substrate 2700 and stores one or more images formed by the reflected light. Alternatively, or in addition, in some embodiments, fluorescent emission from the specimen on the substrate can be detected by light receiving device 2200.

In certain embodiments, light receiving device 2200 is configured to obtain transmission images of specimens on substrates. For example, light emission source 2600 can be positioned below the platform and may direct light so that it passes through platform 2100 and substrate 2700 into light receiving device 2200.

Light receiving device 2200 and any of the other components shown in FIG. 21 can be interfaced with the computer 2300 through links (2011-2014), which can provide energy to the component, provide instructions from computer 2300 to the component, and/or allow the component to send information to computer 2300. Links 2011-2014 can be wired links or wireless links.

Light receiving device 2200 may be capable of X, Y, and Z axial movement (in other embodiments, a motorized stage or substrate mover 2201 may provide X, Y, and Z movement). Light receiving device 2200 can include pan, tilt, and/or locomotive actuators to enable computer 2300 to position light receiving device 2200 in an appropriate position. Light receiving device 2200 can include a lens 2210 that focuses incoming light.

Light receiving device 2200 can be selected to capture black and white and/or color images. In some embodiments, two or more light receiving devices can be used to divide the processing time associated with capturing the images. For example, a low magnification imaging station can be followed by a high magnification imaging station. Similarly, in some embodiments, system 2000, platform 2100, computer 2300, and/or light receiving device 2200 can direct substrate mover 2201 to move substrate 2700 to ensure the capture and storage of one or more images of all, or most, of the cells on the substrate or on a specific portion of the substrate.

Computer 2300 can be a laptop, a server, a workstation, or any other type of computing device. The computer can include a processor, a display 2320, an interface 2310, and internal memory and/or a disk drive. Computer 2300 can also include software stored in the memory or on computer readable, tangible media such as an optical drive. The software may include instructions for causing the computer to operate light receiving device 2200, applicator 2400, gas circulation device 2500, platform 2100, advancer 2110, light source 2600, dispensers 2450 and/or 2800, specimen preparation machine 1, or any component within or connected to one of these components. Similarly, the computer is arranged to receive information from any of these components.

For example, the software may control the rate of dispersal of substrates from the feeder 2102, and feeder 2102 may inform the computer about the number of substrates present. In addition, computer 2300 can also be responsible for performing the analysis of the images captured by light receiving device 2200. Through the analysis process, the computer can be arranged and controlled to calculate the number of a specific type of cell in a particular volume of blood, for example for blood, red cell, white cell, and platelet counts and other measured and derived components of the complete blood count such as: hemoglobin content, red blood cell morphology, or white blood cell count differential could be calculated. The image analysis software can analyze each individual field and sum the total red and white cell counts. To calculate the total counts per microliter in a patient blood sample, the number counted on the slide can be multiplied by the dilution ratio and volume of the sub-sample. Results of the counts, morphologic measurements, and images of red blood cells and white blood cells from the slide may be shown on the display 2320.

In some embodiments, computer 2300 is configured to display numerical data, cell population histograms, scatter plots, and direct assessments of cellular morphology using images of blood cells displayed on the monitor. The ability to display cellular morphology provides users of system 2000 the ability to quickly establish the presence or absence of abnormalities in cell morphology that may warrant preparing an additional slide for manual review by an experienced technician or other professional. The software can also provide the computer with instructions to display images 2331 received from the light receiving device or may cause display 2330 to show the results 2332 (in perhaps a chart or graph, for example) of an analysis of the images. Similarly, computer 2300 can be controlled to enumerate the number of cells of a specific type in a particular blood volume or enumerate the number of damaged cells, cancerous cells, or lysed cells in a particular volume of blood. The software enables the computer to perform the analysis process. The computer can use one or more magnifications during the analysis.

Although shown as one component, computer 2300 can include multiple computers; a first computer can be used for controlling the components of system 2000, and a second computer can be used for processing the images from light receiving device 2200. The various computers can be linked together to allow the computers to share information. Computer 2300 can also be connected to a network or laboratory information system to allow the computer to send and receive information to other computers.

In certain embodiments, applicator 2400 can include a syringe, a manual or motor driven pipettor, or a motor-controlled pump attached through a tube to a pipette tip. Applicator 2400 applies a specimen to substrate 2700 in controlled fashion. Exemplary features, attributes, and methods of using applicator 2400 are disclosed, for example, in U.S. Patent Application Publication No. US 2009/0269799. The specimen can include one or more blood components, cells, tissue, or other biological components.

Once the specimen has been applied to substrate 2700, the applied specimen is processed using machine 1. Machine 1 functions as described herein to apply one or more stain solutions, fixative solutions, and/or other solutions to the specimen on the substrate.

In some embodiments, system 2000 can be configured to achieve minimal overlapping between cells deposited on substrate 2700 by laying down non-touching rows of cells from the tip of applicator 2400. Increasing viscosity of the diluted fluid or the type or amount of diluent may affect the width of the final settlement positions of specimen flows from the applicator. By selecting a distance between rows to allow for the typical variation in blood samples, all cells can be counted in all samples.

Gas movement device 2500, which can be a separate device as shown in FIG. 21, or can be incorporated into machine 1 as discussed previously, can include a fan and/or may include other gas movement devices such as a compressor or a bellows for example. Gas movement device 2500 may be connected directly to the computer 2300 or may be connected through another component such as platform 2100 or applicator 2400. The gas movement device pushes gas (in some cases atmospheric air) across the substrate to control the rate at which substances on the substrate dry. Moving too much air too quickly (i.e., too high of a fan speed) across the substrate can cause cells in the specimen to burst due to rapid drying, and too little air too slowly (i.e., too low of a fan speed) across the substrate can cause the cells to dry too slowly and appear to shrink.

Computer 2300 can select and control the amount of air that moves across the substrate in a period of time (i.e., the cubic feet or cubic centimeters of air per second) based upon the distance the gas movement device is from the substrate, the type of fluid being analyzed, the width of the flows, the temperature of the gas (e.g., air), and the average thickness of the flows. Gas movement device 2500 can be positioned so that the device directs gas so that the gas strikes the substrate at an angle of 30°-60° (e.g., 45°) for a period of about 15 to 20 seconds. In some embodiments, computer 2300 can control humidity and temperature settings in the vicinity of the system to allow the drying process to occur without the use of a gas movement device 2500.

Light emission device 2600, and the various components thereof, are described by way of example in U.S. Patent Application Publication No. US 2009/0269799. Various wavelengths of light can be generated by light emission device 2600 and detected by light receiving device 2200. For example, wavelengths such as 415 nm are useful for obtaining a hemoglobin-only image for assessing RBC morphology and hemoglobin content. Light emitted at 600 nm may be useful to provide high contrast images for platelets and nuclei. Other wavelengths may be chosen in order to best discriminate the colors of basophils, monocytes, lymphocytes (all shades of blue), eosinophils (red), and neutrophils (neutral color).

EXAMPLES

The disclosure is further described by the following examples, which are not intended to limit the scope of the invention recited in the claims.

Example 1

Figure 22:
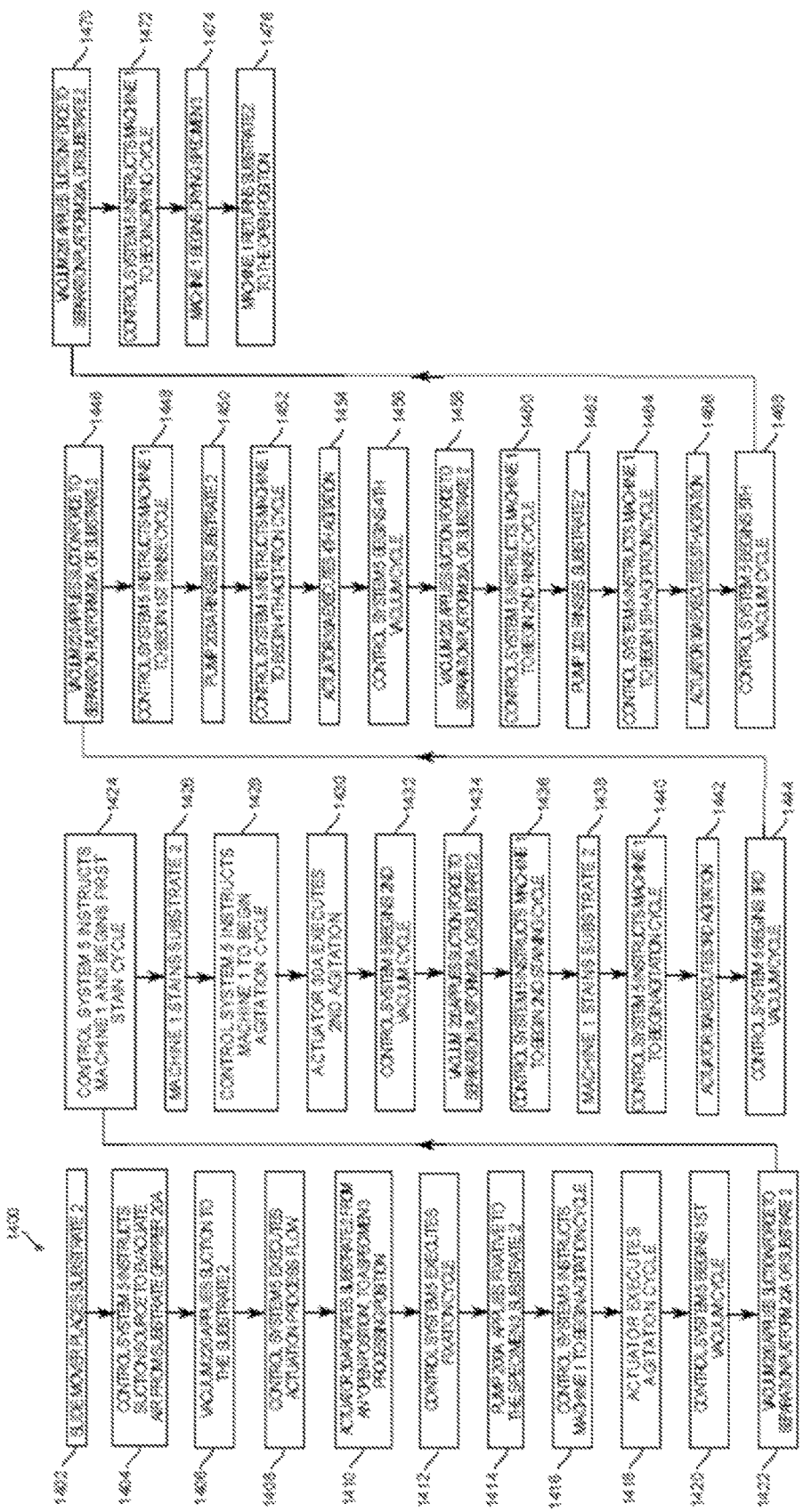
FIG. 22 is a flow chart showing a series of steps for processing a specimen mounted on a substrate.

FIG. 22 is a flow chart 1400 showing a series of exemplary steps for processing a specimen mounted on a substrate. The steps in flow chart 1400 can be used to prepare a specimen for examination. Although the description of this process at times refers to specific steps having specific ranges or discloses steps occurring in a specific sequence, this description is intended to illustrate only one example process. With reference to FIG. 22, machine 1 is connected to a control system 5 for commanding the operation of various machine components during the processing steps. In a specimen initiation step, a specimen 3 that includes red blood cells, white blood cells, and platelets from an aliquot of blood is applied to a substrate 2 consisting of a glass microscope slide. This can be performed using a different station such as one or more of the stations described in co-pending U.S. Patent Application Publication No. 2008/0102006. In a positioning step 1402, substrate 2 containing specimen 3 is loaded onto substrate gripper 20A of substrate arm 10A as shown in FIG. 7. Control system 5 instructs suction source 222 (step 1404) to evacuate air from the substrate gripper 20A. Suction applied through suction ports 21 and 22 (step 1406) adheres the substrate 2 to the substrate gripper 20A during specimen processing. Control system 5 instructs (step 1408) the actuator 30A to rotate the substrate 3 from an open position shown in FIG. 7 to a specimen processing position shown in FIG. 9A. In the specimen processing position, specimen 3 faces the surface of platform 60A while substrate 2 rests against offsets 70A-D shown in FIG. 8. The offsets prevent the substrate 2 from making contact with the surface of platform 60A. In this exemplary process, the separation 92 between the specimen-containing surface of substrate 2 and the surface of platform 60A is approximately 100 microns or 200 microns (e.g., 200 microns).

During a first fixation phase (step 1412, see also FIG. 15), a pump applies a fixative solution to the specimen 3 in step 1414. Pump 200A connected to fluid tube 54A shown in FIG. 8 propels a fixative solution comprising methanol from a fixative reservoir 210 through tube 54A, out port 44A, onto platform 60A, onto substrate 2, and into the separation 92 between platform 60A and substrate 2. Pump 200A propels the fixative solution from port 44A at a flow rate of 115 microliters per second for a two second period T1, thereby directing a total of 230 microliters of the fixative solution, V1, onto substrate 2.

Figure 23:
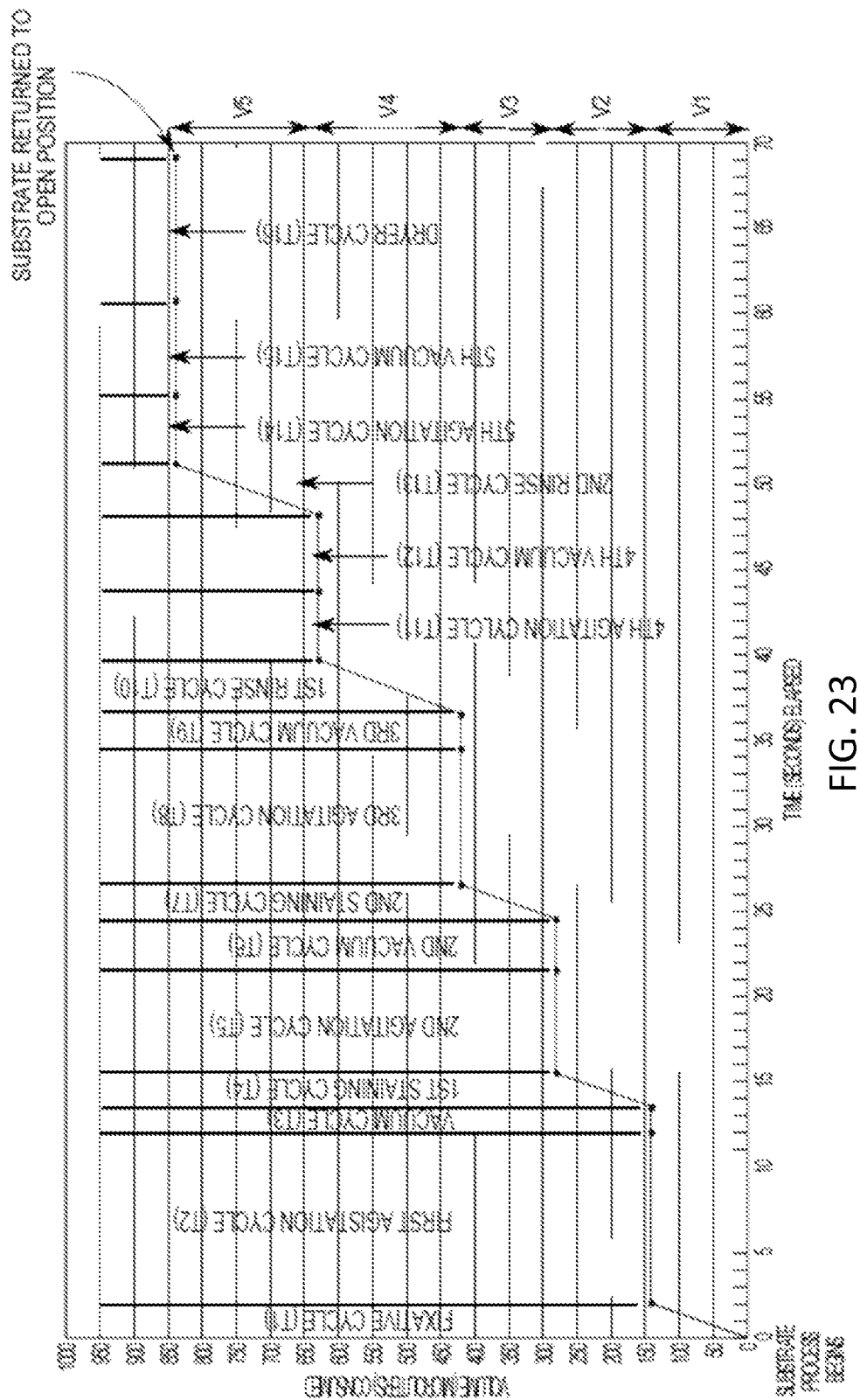
FIG. 23 is a graph showing volume of fluid consumed as a function of time in the flow chart of FIG. 22.

Next, in a first agitation step 1416, control system 5 agitates the substrate by directing actuator 30A (step 1418) to raise the proximate edge of substrate 2 vertically a distance of 35 microns from the specimen processing position and returning the specimen to its specimen processing position. Machine 1 repeats this agitation step four more times. The machine 1 completes the five agitation movements in approximately ten seconds, T2, as shown in FIG. 23. After agitation, the control system initiates a vacuum step 1420. A vacuum force of −0.10 psi is applied for one and a half seconds, T3, evacuating any residual fixative solution (step 1422) present in the separation, on the platform, or on the substrate via ports 40A and 41A, and waste tubes 50A and 51A. The evacuated fixative solution is collected in a waste container 230 and/or 231.

Thereafter, in a second fixation phase including a second agitation step, the foregoing steps of the first fixation phase and first agitation step are repeated.

Following the fixing phase, control system 5 initiates (step 1424) a first staining phase. In doing so, control system 5 directs the machine 1 to stain the specimen (step 1426). Referring to FIG. 8 and the flowchart of FIG. 16, pump 201 connected to fluid tube 52A propels a first stain solution comprising eosin Y from a stain reservoir 211A out port 42A, onto platform 60A, onto substrate 2, and into the separation 92 between the platform 60A and substrate 2. Pump 201 dispenses the first stain solution through port 42A at a flow rate of 115 microliters per second for a two second period, T4, thereby directing 230 microliters of the first stain solution, V2, onto the substrate.

After applying a first stain solution to specimen 3, machine 1 performs a second agitation step 1428 by directing actuator 30A to raise, in step 1430, the proximate edge of substrate 2 vertically a distance of 35 microns from the specimen processing position and then return the specimen to its specimen processing position. Control system 5 causes the machine 1 to repeat this agitation step two more times and complete the three agitations over a period of approximately six seconds, T5, as shown in FIG. 23.

Next a second vacuum phase is initiated in step 1432. A vacuum of five psi applied for three seconds, T6, in step 1434 to evacuate any residual first stain solution present in the separation 92 or on the platform and substrate via ports 40A and/or 41A, and waste tubes 50A and 51A. The evacuated first stain solution is collected in a waste container 230A and/or 231 A.

After staining the specimen with the first stain solution including eosin Y, machine 1 initiates a second staining phase in step 1436 using a second stain solution including azure B and methylene blue. Pump 202 connected to fluid tube 53A propels the second stain solution from a stain reservoir through port 43A, onto platform 60A, onto substrate 2, and into the separation 92 between platform 60A and substrate 2 (step 1438). Machine 1 dispenses the second stain solution through port 43A at a flow rate of 115 microliters per second for a two second period, T7, thereby directing a total of 230 microliters of the second stain solution, V3, onto the substrate.

After applying stain to specimen 3, machine 1 initiates a third agitation phase in step 1440 by directing actuator 30A to raise the proximate edge of substrate 2 (step 1442) a distance of 35 microns from the specimen processing position and then return the specimen 3 to its specimen processing position. Machine 1 repeats this agitation step three more times. The machine completes the four agitation movements over a period of approximately eight seconds, T8.

A third vacuum step 1444 is then initiated. A vacuum of five psi is applied for two seconds, T9, to evacuate residual second stain solution in step 1446 present in the separation or on the platform 60A and substrate 2 via ports 40A and/or 41A, and waste tubes 50A and/or 51A, after agitation. The evacuated second stain solution is collected in a waste container 230A and/or 231A.

Machine 1 then performs two rinse-agitation-vacuum phase sequences. The first sequence of phases is initiated at step 1448 when control system 5 instructs machine 1 to initiate a first rinse phase. A reservoir 213A containing a rinse solution is connected to a pump 203 and fluid tube 55A. Pump 203 directs the rinse solution through wash tube 55A that feeds into port 45A, into the separation 92, and onto platform 60A and substrate 2 to rinse specimen 3 in step 1450. Alternatively, in some embodiments, rinse solution is directed through two or more of fluid ports 42A to 45A. Pump 203 directs the rinse solution out of ports 45A at a flow rate of 115 microliters per second for two seconds, T10, thereby directing a total of 230 microliters, V4, of water onto the substrate. Next, control system 5 initiates a fourth agitation phase in step 1452, directing actuator 30A (step 1454) to raise the proximate edge of substrate 2 vertically a distance of five microns from the specimen processing position and returning the specimen to its specimen processing position. Control system 5 may direct the machine 1 to repeat this agitation phase, and complete the two agitations in approximately four seconds, T11.

Then, a vacuum phase is initiated in step 1456. A vacuum of five psi applied for five and a half seconds, T12, in step 1458, evacuates residual rinse solution present in the separation 92 or on the platform 60A and substrate 2 via ports 40A and/or 41A, and waste tubes 50A and/or 51A after agitation.

Thereafter, in step 1460, control system 5 directs machine 1 to begin the second rinse-agitation-vacuum phase sequence by initiating a second rinse phase. A second rinse phase (steps 1460, 1462), a fifth agitation phase (steps 1464, 1466), and a fifth vacuum phase (steps 1468, 1470) are performed in the same manner as disclosed above for the first rinse-agitation-vacuum phase. During the second rinse-agitation-vacuum phase, the amount of rinse solution, V5, and the processing times T13, T14, and T15 are generally the same as in the first rinse-agitation-vacuum phase sequence.

After the specimen has been fixed, stained with a first stain solution including eosin Y and a second staining solution including azure B and methylene blue, and rinsed, machine 1 initiates a drying phase in step 1472. Dryer 4 directs an air flow of approximately 120° at a 10 liter-per-minute flow rate (step 1474) for an eight second period, T16, across the specimen.

Following completion of these steps, substrate 2 is returned to its original position in step 1476. In this step, actuator 30A rotates substrate 2 from the specimen processing position to the open position as depicted in FIG. 7. Substrate 2 may then be removed by a substrate mover, and a new substrate may be loaded for processing a new specimen.

As illustrated in the exemplary specimen processing steps described above and shown in FIG. 23, the systems and methods disclosed herein provide for more efficient specimen processing by consuming fewer reagents as compared to conventional specimen processing methods including automated and manual specimen preparation techniques.

Referring to FIG. 23, for example, machine 1 consumed less than one and a half milliliters of reagents for fixing, staining, and rinsing the specimen during the exemplary processing steps (e.g., 460 microliters of fixative solution+230 microliters of first stain solution+230 microliters of second stain solution+460 microliters of rinse solution=1380 microliters of reagents). In some embodiments, more or less than 1380 microliters of fluids can be used during specimen processing. For example, the amount of fluid used in processing a specimen can be approximately 1150 microliters (e.g., by eliminating one of the rinse phases).

The above-described fluid volumes relate generally to a spacing of approximately 100 microns between the substrate and platform. When the spacing between the substrate and platform is larger, greater volumes of fluid are generally consumed during specimen processing. For example, when the spacing is approximately 200 microns, the total volume of fluids consumed would have to be more than 1380 microliters.

More generally, the total volume of fluids consumed can be 500 microliters or more (e.g., 520 microliters or more, 540 microliters or more, 560 microliters or more, 580 microliters or more, 600 microliters or more, 650 microliters or more, 700 microliters or more, 750 microliters or more) and/or 2 mL or less (e.g., 1.5 mL or less, 1.4 mL or less, 1.3 mL or less, 1.2 mL or less, 1.1 mL or less, 1.0 mL or less, 900 microliters or less).

Referring again to FIG. 23, the specimen preparation process is completed in slightly more than one minute (e.g., 13.5 seconds elapsed during each of the fixing phases for a total of 27 seconds for fixing+11 seconds elapsed during the first staining phase+12 seconds elapsed during the second staining phase+23 seconds elapsed during the rinse phases+8 seconds elapsed during the drying phase=81 seconds total elapsed time). In certain embodiments, specimen preparation can be completed in more or less than 81 seconds. For example, specimen processing can be completed in 180 seconds or less (e.g., 150 seconds or less, 120 seconds or less, 90 seconds or less, 80 seconds or less, 70 seconds or less, 60 seconds or less, 50 seconds or less, or 40 seconds or less).

Further, while the foregoing exemplary process describes processing time for a single specimen, systems and methods for processing multiple substrates (e.g., machine 1 in FIG. 7, configured to process two substrates, and/or systems configured to process three or more substrates) are capable of processing more than 100 specimens per hour (e.g., between 60 specimens and 120 specimens per hour). Use of the systems and methods disclosed herein in laboratory settings can result in faster throughput on a per specimen basis, while consumption of fluids (e.g., fixative, stain, and rinse fluids) is reduced compared to conventional automated systems and manual specimen preparation techniques.

Example 2

The processing steps described above for Example 1 may be adjusted in other embodiments of the invention as follows. In addition, fixative, stains, and rinse solution formulations described herein can be used in the following example processing steps.

During a first fixation phase (step 1412, see also FIG. 22), a pump applies a fixative solution to the specimen 3 in step 1414. Pump 200A connected to fluid tube 54A shown in FIG. 8 propels a fixative solution comprising methanol from a fixative reservoir 210 through tube 54A, out port 44A, onto platform 60A, onto substrate 2, and into the separation 92 between platform 60A and substrate 2. Pump 200A propels the fixative solution from port 44A at a flow rate of 115 microliters per second for a two second period T1, thereby directing a total of 230 microliters of the fixative solution, V1, onto substrate 2.

Next, in a first agitation step 1416, control system 5 agitates the substrate by directing actuator 30A (step 1418) to raise the proximate edge of substrate 2 vertically a distance of 35 microns from the specimen processing position and returning the specimen to its specimen processing position. Machine 1 repeats this agitation step five more times. The machine 1 completes the six agitation movements in approximately 12 seconds. After agitation, the control system initiates a vacuum step 1420. A vacuum force of negative six psi is applied for one and a half seconds, T3, evacuating any residual fixative solution (step 1422) present in the separation, on the platform, or on the substrate via ports 40A and 41A, and waste tubes 50A and 51A. The evacuated fixative solution is collected in a waste container 230 and/or 231.

Thereafter, in a second fixation phase including a second agitation step, the foregoing steps of the first fixation phase and first agitation step are repeated.

Following the fixing phases, control system 5 initiates (step 1424) a first staining phase. In doing so, control system 5 directs the machine 1 to stain the specimen (step 1426). Referring to FIG. 8 and the flowchart of FIG. 16, pump 201 connected to fluid tube 52A propels a first stain solution comprising eosin Y from a stain reservoir 211A out port 42A, onto platform 60A, onto substrate 2 including specimen 3, and into the separation 92 between the platform 60A and substrate 2. Pump 201 dispenses the first stain solution through port 42A at a flow rate of 115 microliters per second for a two second period, T4, thereby directing 230 microliters of the first stain solution, V2, onto the substrate.

After applying a first stain solution to specimen 3, machine 1 performs a second agitation step 1428 by directing actuator 30A to raise, in step 1430, the proximate edge of substrate 2 vertically a distance of 35 microns from the specimen processing position and then return the specimen to its specimen processing position. Control system 5 causes the machine 1 to repeat this agitation step two more times and complete the three agitations over a period of approximately six seconds, T5, as shown in FIG. 23.

Next a second vacuum phase is initiated in step 1432. A vacuum of negative five psi applied for three seconds, T6, in step 1434 to evacuate any residual first stain solution present in the separation 92 or on the platform and substrate via ports 40A and/or 41A, and waste tubes 50A and 51A. The evacuated first stain solution is collected in a waste container 230A and/or 231 A.

After staining the specimen with the first stain solution including eosin Y, machine 1 initiates a second staining phase in step 1436 using a second stain solution including azure B and methylene blue. Pump 202 connected to fluid tube 53A propels the second stain solution from a stain reservoir through port 43A, onto platform 60A, onto substrate 2, and into the separation 92 between platform 60A and substrate 2 (step 1438). Machine 1 dispenses the second stain solution through port 43A at a flow rate of 115 microliters per second for a two second period, T7, thereby directing a total of 230 microliters of the second stain solution, V3, onto the substrate.

After applying stain to specimen 3, machine 1 initiates a third agitation phase in step 1440 by directing actuator 30A to raise the proximate edge of substrate 2 (step 1442) a distance of 35 microns from the specimen processing position and then return the specimen 3 to its specimen processing position. Machine 1 repeats this agitation step two more times. The machine completes the three agitation movements over a period of approximately six seconds, T8.

A third vacuum step 1444 is then initiated. A vacuum of negative six psi is applied for two seconds, T9, to evacuate residual second stain solution in step 1446 present in the separation or on the platform 60A and substrate 2 via ports 40A and/or 41A, and waste tubes 50A and/or 51A, after agitation. The evacuated second stain solution is collected in a waste container 230A and/or 231A.

Machine 1 then performs two rinse-agitation-vacuum phase sequences. The first sequence of phases is initiated at step 1448 when control system 5 instructs machine 1 to initiate a first rinse phase. A reservoir 213A containing a rinse solution is connected to a pump 203 and fluid tube 55A. Pump 203 directs the rinse solution through wash tube 55A that feeds into port 45A, into the separation 92, and onto platform 60A and substrate 2 to rinse specimen 3 in step 1450. Alternatively, in some embodiments, rinse solution is directed through two or more of fluid ports 42A to 45A. Pump 203 directs the rinse solution out of ports 45A at a flow rate of 115 microliters per second for two seconds, T10, thereby directing a total of 230 microliters, V4, of water onto the substrate.

Next, control system 5 initiates a fourth agitation phase in step 1452, directing actuator 30A (step 1454) to raise the proximate edge of substrate 2 vertically a distance of 35 microns from the specimen processing position and returning the specimen to its specimen processing position. Control system 5 then directs the machine 1 to repeat this agitation phase three more times, and complete the four agitations in approximately eight seconds, T11.

Then, a vacuum phase is initiated in step 1456. A vacuum of five psi applied for five and a half seconds, T12, in step 1458, evacuates residual rinse solution present in the separation 92 or on the platform 60A and substrate 2 via ports 40A and/or 41A, and waste tubes 50A and/or 51A after agitation.

Thereafter, in step 1460, control system 5 directs machine 1 to begin the second rinse-agitation-vacuum phase sequence by initiating a second rinse phase. A second rinse phase (steps 1460, 1462), a fifth agitation phase comprising six agitations completed in approximately 12 seconds, and a fifth vacuum phase (steps 1468, 1470) are performed in the same manner as disclosed above for the first rinse-agitation-vacuum phase. During the second rinse-agitation-vacuum phase, the amount of rinse solution, V5, and the processing times T13, T14, and T15 are generally the same as in the first rinse-agitation-vacuum phase sequence. In addition, immediately prior to the vacuum phase, actuator 30A raises the proximate edge of substrate 2 a distance of 15-35 microns from the specimen processing position. This increased separation between substrate 2 and platform 60 improves evacuation of any residual fluids in separation 92 during the final vacuum phase.

After the specimen has been fixed, stained with a first stain solution containing eosin Y and a second staining solution containing azure B and methylene blue, and rinsed, machine 1 initiates a drying phase in step 1472. Dryer 4 directs an air flow of approximately 120° at a 10 liter-per-minute flow rate (step 1474) for an eight second period, T16, across the specimen.

Following completion of these steps, substrate 2 is returned to its original position in step 1476. In this step, actuator 30A rotates substrate 2 from the specimen processing position to the open position as depicted in FIG. 7.

Substrate 2 may then be removed by a substrate mover, and a new substrate may be loaded for processing a new specimen.

As illustrated in the example specimen processing steps described above, the systems and methods disclosed herein provide for more efficient specimen processing by consuming fewer reagents as compared to conventional specimen processing methods including automated and manual specimen preparation techniques. Referring to Example 2, machine 1 consumed less than one and a half milliliters of reagents for fixing, staining, and rinsing the specimen during the exemplary processing steps (e.g., 460 microliters of fixative solution+230 microliters of first stain solution+230 microliters of second stain solution+460 microliters of rinse solution=1380 microliters of reagents). In some embodiments, more or less than 1380 microliters of fluids can be used during specimen processing. For example, the amount of fluid used in processing a specimen can be approximately 1150 microliters (e.g., by eliminating one of the rinse phases) or less than 1,000 microliters (e.g., by further eliminating one of the fixative phases).

With respect to FIG. 23, for Example 1, machine 1 consumed less than one milliliter of reagents for fixing, staining, and rinsing the specimen during the exemplary processing steps (e.g., 140 microliters of methanol fixative+140 microliters of fluorescein dye+140 microliters of thiazin dye+280 microliters of rinse solution=700 microliters of reagents). In some embodiments, more or less than 700 microliters of fluids can be used during specimen processing. For example, the amount of fluid used in processing a specimen can be approximately 560 microliters (e.g., by eliminating one of the rinse phases).

In general, the total volume of fluids consumed can be 500 microliters or more (e.g., 520 microliters or more, 540 microliters or more, 560 microliters or more, 580 microliters or more, 600 microliters or more, 650 microliters or more, 700 microliters or more, 750 microliters or more) and/or 2 mL or less (e.g., 1.5 mL or less, 1.4 mL or less, 1.3 mL or less, 1.2 mL or less, 1.1 mL or less, 1.0 mL or less, 900 microliters or less).

Referring to FIG. 23 and Example 1, the specimen preparation process is completed in slightly more than one minute (e.g., 13.5 seconds elapsed during the fixing phase+11 seconds elapsed during the fluorescein dye phase+12 seconds elapsed during the thiazin dye phase+23 seconds elapsed during the rinse phases+8 seconds elapsed during the drying phase=67.5 seconds total elapsed time). In certain embodiments, specimen preparation can be completed in more, as in Example 2, or less than 67.5 seconds. For example, specimen processing can be completed in 180 seconds or less (e.g., 150 seconds or less, 120 seconds or less, 90 seconds or less, 80 seconds or less, 70 seconds or less, 60 seconds or less, 50 seconds or less, or 40 seconds or less).

Further, while the foregoing exemplary process describes processing time for a single specimen, systems and methods for processing multiple substrates (e.g., machine 1 in FIG. 7, configured to process two substrates, and/or systems configured to process three or more substrates) are capable of processing more than 100 specimens per hour (e.g., between 60 specimens and 120 specimens per hour). Use of the systems and methods disclosed herein in laboratory settings can result in faster throughput on a per specimen basis, while consumption of fluids (e.g., fixative, stain, and rinse fluids) is reduced compared to conventional automated systems and manual specimen preparation techniques.

Example 3

For each of the series of experiments in Table 1, blood samples were prepared using the sample preparation technique as described, for example, in U.S. Publication No. US20090269799. The samples were then processed by fixing, staining, and rinsing generally according to Example 1, and the flow rate was 115 µL/s for two seconds for each of the fixative solution, stain solutions, and rinse solutions. For each set of experiments listed below, substrates (e.g., microscope slides) were prepared from at least five blood samples. Next, the processed samples were manually evaluated and the quality of the sample staining and preparation (e.g., overall uniformity of staining, color, differentiation of cellular features, presence/absence of debris in background, etc.) was assessed under a microscope, using at least 10× magnification. Manual evaluation was performed to compare the stain and sample preparation quality of the sample specimen versus the stain and sample prep quality of a control specimen. A "rolling control condition" was typically employed, where a previous formulation that provided optimal staining and sample preparation was used as the control for comparing new adjustments to the various formulations. Thus (unless otherwise specified below), any given row in Table 1 typically represents the control condition for the series of experiments summarized in the following row. For a limited number of samples and after manual review, the samples were processed on an imager as described in US20090269799 to test how, if at all, the formulations impacted the imager's ability to classify the five types of WBCs present in the sample. These results are reported in Table 2.

TABLE 1

Formulation assessment experiments.

| Experiment, in chronological order | Formulation | Property Tested | Range/parameter tested | Observations/Results |
|---|---|---|---|---|
| 2A | Fixative | Dye addition | Azure B | Prior to this series of experiments, less-than-optimal staining of basophils was observed (e.g., insufficient differentiation between nucleus and cytoplasmic granules). Adding dye to the fixative composition showed significant improvement in basophil staining (e.g., observed orange-reddish cytoplasmic granule staining). This fixative formulation remained constant until experiment 2L. |

TABLE 1-continued

Formulation assessment experiments.

| Experiment, in chronological order | Formulation | Property Tested | Range/ parameter tested | Observations/Results |
|---|---|---|---|---|
| 2B | Rinse | MeOH Conc | 0%, 5% | The 5% MeOH in rinse solution showed slightly improved evacuation of rinse solution from the platen as compared to a rinse solution without MeOH. |
| 2-1 | | | | See Classification Results, Table 2. |
| 2C | Blue Stain | pH | 5.85-7.86 | Selected pH 6.5 for Blue Stain solution (containing Azure B, but not Methylene Blue) as a result of this series of experiments. Higher pH values provided less than optimal staining (e.g., cytoplasm stained too dark, neutrophils stained too blue). HEPES buffer was used to achieve desired pH. |
| 2-2 | | | | See Classification Results, Table 2. |
| 2D | Blue Stain | Tween 20 Conc | 0.01%-0.1% | 0.1% Tween 20 was ultimately selected. The blue and red stain formulations had an improved ability to uniformly stain the sample, as well as decreased risk of precipitation and non-specific binding of stain. |
| 2E | Red Stain | Tween 20 Conc | 0.01%-0.5% | 0.1% Tween 20 was selected in the first and second stain formulations. The formulations had an improved ability to uniformly stain the sample, as well as decreased risk of precipitation and non-specific binding of stain. |
| 2F | 50/50 Blue | Antimicrobial | ProClin 300 ® | |
| 2G | Red Stain | Antimicrobial | ProClin 300 ® | |
| 2H | Rinse | Antimicrobial | Benzalkonium chloride, ProClin 300 ® | ProClin 300 ® was selected as the antimicrobial agent for the rinse solution (as well as red and blue stains as noted in previous two rows) over benzalkonium chloride due to benzalkonium chloride's tendency to cause precipitation in the rinse solution. |
| 2I | Red Stain | Eosin Conc | 0.75 g/L-1.25 g/L | Experiments were performed to evaluate staining WBC cytoplasms, particularly in immature granulocytes. Previous formulations, before an eosin concentration of 0.75 g/L was selected, caused excessive redness in cytoplasms. |
| 2J | Blue Stain | Methylene blue Conc | 0%-70% | Various relative proportions of Azure B and Methylene Blue were tested in a blue staining solution. A 50/50 formulation showed improved staining in lymphocyte and monocyte cytoplasms, and was found to be a significant contributor to solving the excessively red cytoplasm staining issue described in the preceding row. Azure B was also generating a red component to cytoplasmic staining, particularly lymphocytes and monocytes, which ultimately led to selection of 50% methylene blue. |
| 2K | 50/50 Blue | pH | 6.5-7.0 | Using a 50/50 azure B/methylene blue stain formulation as the control, the pH of the blue stain solution was varied. At pH 7.0 for the blue stain, slight improvement (i.e., darker) on platelet staining was observed. The 50/50 Blue stain formulation remained constant until experiment 2W. |
| 2L | Fixative | Tween 20 Conc | 0%-0.5% | 0.1% Tween 20 was used in fixative solution. Using various points within the range, 0.1% Tween 20 showed better stain consistency throughout the sample deposited on the slide. Without the detergent, the stain would not flow evenly across staining platen, often leaving an unstained spot in the middle of the sample. |
| 2M | Fixative | pH | 5.0-8.0 | A series of experiments was conducted to verify that pH 7 was optimal for the |

TABLE 1-continued

Formulation assessment experiments.

| Experiment, in chronological order | Formulation | Property Tested | Range/ parameter tested | Observations/Results |
|---|---|---|---|---|
| | | | | fixative. A pH of 6.5 or less showed poor overall staining appearance. |
| 2N | Rinse | pH | 4.0-8.0 | The pH of the rinse was varied to evaluate impact on staining quality and ultimately a pH of 6.8 was selected. Higher pH caused bluer RBCs. Lower pH caused excessively red RBCs. |
| 2-3 | | | | See Classification Results, Table 2. |
| 2O | Rinse | Tween 20 Conc | 0.01%-0.1% | 0.1% Tween 20 concentration for the rinse solution was re-evaluated and re-confirmed. |
| 2P | Red Stain | pH | 5.7-7.7 | The pH of the red stain was varied to determine an optimal pH for cytoplasmic staining. pH 6 was selected. |
| 2Q | Red Stain | MeOH Conc | 70% | 70% MeOH in a red stain formulation at pH 6 and pH 3.9 were evaluated to determine whether the formulation could increase processing speed and improve overall appearance and color of prepared samples. 70% MeOH at pH 6 showed poor overall staining. 70% MeOH at pH 3.9 showed marginal overall staining and saturated RBCs. |
| 2R | 50/50 Blue | Dye Conc | 0.5 g/L-1.0 g/L | Concentrations of about 0.5 g/L for both Azure B and Methylene B concentrations in blue stain were reconfirmed. |
| 2S | Red Stain | Buffer | phosphate buffers, BisTris | As a result of this series of experiments, BisTris buffer was selected over phosphate buffers for the red stain formulation. Without wishing to be bound by any theory, it is believed that in some embodiments, the phosphate buffers can act as growth media for microorganisms. |
| 2T | Red Stain w/BisTris | pH | 5.5-6.0 | A pH of 6.0 was reconfirmed for the red stain formulation. |
| 2U | Red Stain w/BisTris, NaCl | pH | 5.0-6.0 | A pH of 6.0 was reconfirmed for the red stain formulation. |
| 2V | Red Stain w/BisTris | NaCl Conc | 0%-0.6% | Various concentrations of NaCl were tested and 0.4% NaCl was selected for the red stain formulation. NaCl can decrease hemolysis and debris in a specimen's background. In addition, NaCl can minimize non-specific binding of stain. Without wishing to be bound by any theory, it is believed that a change from a phosphate to BisTris buffer may have contributed to debris present in the specimen's background. |
| 2W | 50/50 Blue | NaCl Conc | 0%-0.2% | Various concentrations of NaCl were tested and 0.2% NaCl was selected for the blue stain formulation. Without wishing to be bound by any theory, it is believed that NaCl can decrease hemolysis and debris in a specimen's background. In addition, NaCl can minimize non-specific binding of stain. |
| 2X | 50/50 Blue | Glycol | 1% propylene, ethylene, PE glycol | With respect to experiments described in this row and next two rows, 1.0% ethylene glycol was used in fixative and red stain solutions, as too little chromatin texture was observed in blast cells when observed through manual review. Ethylene glycol was not added to the blue stain solution because it produced no discernible effect on blast cells or otherwise. |
| 2Y | Fixative | Glycol | 1% propylene, ethylene, PE glycol | |
| 2Z | Red Stain | Glycol | 1% propylene, | |

TABLE 1-continued

Formulation assessment experiments.

| Experiment, in chronological order | Formulation | Property Tested | Range/ parameter tested | Observations/Results |
|---|---|---|---|---|
| 2AA | 50/50 Blue | Buffer | ethylene, PE glycol HEPES Sodium Salt, BisTris | Different buffers were tested in a blue stain formulation. BisTris was selected as a buffer, as it showed improved compatibility (i.e., less reactions) with red stain solution. |
| 2BB | Rinse | Buffer | MES, HEPES Sodium Salt/Acid, BisTris | |
| 2CC | Rinse | PEG Conc | 0%-1% | 0.5% polyethylene glycol was selected for the rinse solution, based on general overall appearance of sample and its ability to fix prepared samples. 0.5% formulation reduced the amount of residue left on the slide after evacuating the rinse solution as compared to rinse solution containing 1% polyethylene glycol. |
| 2DD | Fixative | Ethylene Glycol Conc | 0%-5% | 1% ethylene glycol in the fixative solution was confirmed by looking at samples treated with 1, 2 and 5% ethylene glycol fixative solutions. Confirmed by manual review. |
| 2EE | Red Stain | Ethylene Glycol Conc | 0%-5% | 1% ethylene glycol in the red stain solution was confirmed by looking at samples treated with 1, 2 and 5% ethylene glycol red stain solutions. Confirmed by manual review. |
| 2FF | Rinse | All components | 100%, 20% | Evaluated overall sample appearance and staining uniformity through a series of experiments by comparing samples prepared with previous rinse formulation and samples prepared with a 20% rinse formulation (i.e., reducing all components to one-fifth of previous formulation). 20% rinse formulation showed significant improvement over previous formulation by (i) reducing the extent of dried rinse film and reside left on sample, (ii) correcting tendency for sample to appear redder and diluting blue stain, (iii) diminishing stain spotting on sample and areas containing excessively red nuclei, and (iv) refining overall sample appearance and staining uniformity. |

The WBC classifier results listed in Table 2 compare the automated machine WBC classification results as described in U.S. Publication No. US20090269799, herein incorporated in its entirety, against a manual classification of WBCs in the sample. The percentages reflect an automated machine classifier accuracy compared to manual review and classification of WBCs in the sample. For each of the three experiments (2-1, 2-2, and 2-3), a minimum of ten samples prepared using then-current fixative and staining solutions were processed on the system and compared to a manual review of WBCs in each sample. Each manual review consisted of a WBC differential performed on at least 100 WBCs in the sample.

TABLE 2

White blood cell ("WBC") classification results.

| WBC Cell Type | 2-1 | 2-2 | 2-3 |
|---|---|---|---|
| Lymph | 60.3% | 93.7% | 97.2% |
| Mono | 83.3% | 88.2% | 94.3% |
| Neut | 89.2% | 97.6% | 99.1% |
| Baso | NA | NA | 100.0% |
| Eo | 83.7% | 94.9% | 99.0% |

Example 4

Dozens of commercially available hematology fixative and staining products were tested in the systems described herein; such products were generally unsuitable for use with the cell identifying, counting, and classification systems described herein. For example, the staining darkness achieved with these products was compared with that achieved with the formulations described herein. In general, the products tested did not produce the optimal sample preparation results (e.g., did not stain samples as darkly or as uniformly) as the formulations described herein. The commercially available products, for example, produced lightly stained nuclei and cytoplasms when compared with the formulations described herein.

OTHER EMBODIMENTS

It is to be understood that while the invention has been described in conjunction with the detailed description, the foregoing description is intended to illustrate and not limit the scope of the disclosure, which is defined by the scope of the appended claims. Other aspects, advantages, and modifications are within the scope of the following claims.

All references, such as patent applications, publications, and patents, referred to herein are incorporated by reference in their entirety.

What is claimed is:

1. A cytological fixative solution consisting of
    a single thiazine dye;
    a surfactant;
    a buffering agent;
    methanol; and
    an agent selected from the group consisting of ethylene glycol, propylene glycol, polyethylene glycol, and any combination thereof.

2. The cytological fixative solution of claim 1, wherein the thiazine dye is Azure B.

3. The cytological fixative solution of claim 1, wherein the thiazine dye is present in an amount of from about 0.5 to about five g/L.

4. The cytological fixative solution of claim 1, wherein the surfactant is present in an amount of from about 0.05% to about 0.5% by volume.

5. The cytological fixative solution of claim 1, wherein the surfactant is present in an amount of from about 0.05% to about 0.3% by volume.

6. The cytological fixative solution of claim 1, wherein the surfactant is selected from the group consisting of non-ionic, cationic, anionic, and zwitterionic surfactants.

7. The cytological fixative solution of claim 6, wherein the non-ionic surfactant is polysorbate 20.

8. The cytological fixative solution of claim 7, wherein polysorbate 20 is present in an amount of from about 0.5 mL/L to about 5.0 mL/L.

9. The cytological fixative solution of claim 1, wherein the buffering agent is selected from the group consisting of bis-tris, phosphate, HEPES, MES, Tris, and any combination thereof.

10. The cytological fixative solution of claim 9, wherein a 1:10 dilution of the solution in water has a pH of from 6 to 8 and HEPES is present in an amount of from about 0.5 mM to about 10 mM.

11. The cytological fixative solution of claim 9, wherein a 1:10 dilution of the solution in water has a pH of from 6.7 to 7.3 and HEPES is present in an amount of from about 0.5 mM to about 10 mM.

12. The cytological fixative solution of claim 1, wherein the agent is ethylene glycol.

13. The cytological fixative solution of claim 1, wherein the agent is present in an amount of from about 0.5 to about 5% by volume.

14. The cytological fixative solution of claim 1, wherein a 1:1000 dilution of the fixative solution in water has a UV absorbance of from about 0.1 to about one at a peak wavelength of from about 640 to about 650 nm.

15. The cytological fixative solution of claim 1, wherein the surfactant is non-ionic.

16. A cytological fixative solution consisting of
    a single thiazine dye in an amount of from about 0.5 g/L to about 5.0 g/L;
    about 0.5 mL/L to about 5.0 mL/L polysorbate 20;
    about 5 mL/L to about 50 mL/L ethylene glycol;
    about 0.10 g/L to about 10 g/L HEPES sodium salt; and
    methanol.

* * * * *